US009279817B2

(12) United States Patent
Diwu et al.

(10) Patent No.: US 9,279,817 B2
(45) Date of Patent: Mar. 8, 2016

(54) CARBOFLUORESCEIN LACTONE ION INDICATORS AND THEIR APPLICATIONS

(71) Applicant: AAT Bioquest, Inc., Sunnyvale, CA (US)

(72) Inventors: Zhenjun Diwu, Sunnyvale, CA (US); Haitao Guo, Sunnyvale, CA (US); Ruogu Peng, Sunnyvale, CA (US); Qin Zhao, Sunnyvale, CA (US); Jixiang Liu, Santa Clara, CA (US); Jinfang Liao, Foster City, CA (US)

(73) Assignee: AAT Bioquest, Inc., Sunnyvale, CA (US)

( * ) Notice: Subject to any disclaimer, the term of this patent is extended or adjusted under 35 U.S.C. 154(b) by 0 days.

(21) Appl. No.: 14/450,658

(22) Filed: Aug. 4, 2014

(65) Prior Publication Data
US 2014/0378344 A1 Dec. 25, 2014

Related U.S. Application Data

(60) Continuation-in-part of application No. 13/374,967, filed on Jan. 25, 2012, now Pat. No. 9,097,730, which is a continuation-in-part of application No. 12/932,683, filed on Mar. 2, 2011, now Pat. No. 8,779,165, which is a division of application No. 12/040,753, filed on Feb. 29, 2008, now abandoned.

(60) Provisional application No. 60/923,452, filed on Apr. 13, 2007.

(51) Int. Cl.
*C07C 229/60* (2006.01)
*C07C 247/02* (2006.01)
*G01N 33/84* (2006.01)
*C09B 5/00* (2006.01)
*G01N 33/50* (2006.01)
*C07D 311/90* (2006.01)
*C07D 219/06* (2006.01)
*C07D 493/10* (2006.01)
*G01N 33/533* (2006.01)
*C07D 307/94* (2006.01)
*C07C 247/04* (2006.01)

(52) U.S. Cl.
CPC .............. *G01N 33/84* (2013.01); *C07C 229/60* (2013.01); *C07C 247/04* (2013.01); *C07D 219/06* (2013.01); *C07D 307/94* (2013.01); *C07D 311/90* (2013.01); *C07D 493/10* (2013.01); *C09B 5/00* (2013.01); *G01N 33/5041* (2013.01); *G01N 33/533* (2013.01); *C07C 2103/24* (2013.01)

(58) Field of Classification Search
CPC .................... C07D 307/94; C09B 5/00
See application file for complete search history.

(56) References Cited

U.S. PATENT DOCUMENTS

| | | |
|---|---|---|
| 4,603,209 A | 7/1986 | Tsien et al. |
| 4,849,362 A | 7/1989 | DeMarinis et al. |
| 4,945,171 A | 7/1990 | Haugland et al. |
| 5,049,673 A | 9/1991 | Tsien et al. |
| 5,134,232 A | 7/1992 | Tsien et al. |
| 5,227,487 A | 7/1993 | Haugland et al. |
| 5,380,836 A | 1/1995 | Rogart |
| 5,405,975 A | 4/1995 | Kuhn et al. |
| 5,436,128 A | 7/1995 | Harpold et al. |
| 5,439,828 A | 8/1995 | Masilamani et al. |
| 5,453,517 A | 9/1995 | Kuhn et al. |
| 5,459,276 A | 10/1995 | Kuhn et al. |
| 5,501,980 A | 3/1996 | Katerinopoulos et al. |
| 5,516,911 A | 5/1996 | London et al. |
| 5,773,227 A | 6/1998 | Kuhn et al. |
| 6,057,114 A | 5/2000 | Akong et al. |
| 6,162,931 A | 12/2000 | Gee et al. |
| 6,420,183 B1 | 7/2002 | Krahn et al. |
| 9,097,730 B2 * | 8/2015 | Diwu ................. C07D 219/06 |
| 2001/0006820 A1 | 7/2001 | Knapp et al. |
| 2002/0164616 A1 | 11/2002 | Martin et al. |
| 2012/0183986 A1 * | 7/2012 | Diwu ................. C07D 219/06 435/29 |

OTHER PUBLICATIONS

Grimm et al, ACS Chemical Biology, Carbofluoresceins and Carborhodamines as Scaffolds for High-Contrast Fluorogenic Probes, 2013, 8, pp. 1303-1310.*
Adams et al., "Permeability in Atherosclerosis", Atherosclerosis, 27(1977), 353-359.
Bacci et al., "Efficient Two-Step Synthesis of 9-Aryl-6-hydroxy-3H-xanthen-3-one Fluorophores", J Org Chem (2005), 70:9051-9053.
Chun et al., "D1-D2 Dopamine Receptor Synergy Promotes Calcium Signaling via Multiple Mechanisms", Mol Pharmacol (2013), 84:190-200.
Davis et al., "Fluoresence of Trypan Blue in Frozen-Dried Embryos of the Rat", Histochemistry (1977), 54(3):177-189.
Eidelman et al., "Continuous monitoring of transport by fluorescence on cells and vesicles", Biochim Biophys Acta (1989), 988(3):319-34.
Gee et al., "Detection and imaging of zinc secretion from pancreatic beta-cells using a new fluorescent zinc indicator", J Am Chem Soc (2002), 124(5)776-8.
Hathaway et al., "The acridine orange viability test applied to bone marrow cells. II. Correlation with an in vivo irradiated mouse assay", Cryobiology (1965), 2(3):143-146.
Kurogi et al., "Green Tea Polyphenol Epigallocatechin Gallate Activates TRPA1 in an Intestinal Enteroendocrine Cell Line, STC-1", Chem. Senses (2012), 37:167-177.
Lakowitz, "Topics in Fluorescence Spectroscopy", vol. 4: Probe Design and Chemical Sensing; Plenum Press, New York & London (1994).
Martin et al., "Fluorescent sodium ion indicators based on the 1,7-diaza-15-crown-5 system", Bioorg Med Chem Lett (2004), 14(21):5313-6.

(Continued)

*Primary Examiner* — Paul A Zucker
(74) *Attorney, Agent, or Firm* — Glenn J. Foulds; Bret E. Field; Bozicevic, Field & Francis LLP

(57) ABSTRACT

Fluorescent dyes useful for preparing fluorescent metal ion indicators, the fluorescent indicators themselves, and the use of the fluorescent indicators for the detection, discrimination and quantification of metal cations are provided.

7 Claims, 12 Drawing Sheets

(56) References Cited

OTHER PUBLICATIONS

Parham et al., "Aromatic organolithium reagents bearing electrophilic groups. Preparation by halogen-lithium exchange", Acc. Chem. Res. (1982), 15(10):300-305.

Podust et al., "Extension of in vivo half-life of biologically active peptides via chemical conjugation to XTEN protein polymer", Protein Engineering, Design & Selection (2013), 26(11):743-753.

Senbagavalli et al., "Immune Complexes Isolated from Patients with Pulmonary Tuberculosis Modulate the Activation and Function of Normal Granulocytes", Clinical and Vaccine Immunology (2012), 19(12):1965-1971.

Vicini, "Study of calcium signalling by fluorescent imaging", Studienwoche Schweizer Jugend forscht, Universite De Geneve, (2011).

"Human CRAC (STIM1/ORAI1) Ion Channel Cell Line", Technical Data Sheet, PhotoScreen Ion Channel Cell Line, PerkinElmer, Inc., pp. 1-9, (2009).

Molecular Probes Inc., Handbook of Fluorescent Probes and Research Chemicals, 7th edition, Chapter 1, Eugene, Oregon (1996-2007).

Online "http://www.interchim.fr/cat/CalciumAssays.pdf" Mar 31, 2004—Fluo-8 AM. "[PDF] Calcium Assays—Interchim" accessed Sep. 16, 2013.

Online "http://www.teflabs.com/Portals/44052/docs/Fluo-2-MA-Info-Packet1.pdf" accessed Sep. 17, 2013.

Yang et al., "Functional analysis of G-protein coupled receptors using a new fluorescein lactone-based intracellular calcium indicator", Anal Methods (2010), 2:295-298.

Hodder et al., Miniaturization of intracellular calcium functional assays to 1536-well plate format using a fluorometric imaging plate reader, J Biomol Screen (2004), 9(5):417-426.

* cited by examiner

Fluo-3

Fluo-3 AM

Fluo-4

Fluo-4 AM

US 9,279,817 B2

CARBOFLUORESCEIN LACTONE ION INDICATORS AND THEIR APPLICATIONS

CROSS-REFERENCE TO RELATED APPLICATIONS

This application is a continuation-in-part of U.S. patent application Ser. No. 13/374,967, filed Jan. 25, 2012, which is a continuation-in-part of U.S. patent application Ser. No. 12/932,683, filed Mar. 2, 2011, which is a divisional of U.S. patent application Ser. No. 12/040,753, filed Feb. 29, 2008, which claims priority under 35 U.S.C. §119(e) to U.S. provisional patent application Ser. No. 60/923,452, filed Apr. 13, 2007, each of which is hereby incorporated by reference.

BACKGROUND

Metal ions play important roles in many biological systems. Cells utilize metal ions for a wide variety of functions, such as regulating enzyme activities, protein structures, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. Ion chelators can be used as optical indicators of ions when bound to a fluorophore, and may be useful in the analysis of cellular microenvironments or dynamic properties of proteins, membranes and nucleic acids. For example, $Ca^{2+}$ ions play an important role in many biological events, and so the determination of intracellular $Ca^{2+}$ is an important biological application.

Fluorescent indicators utilizing a BAPTA chelator have been predominantly used for intracellular calcium detections (see U.S. Pat. No. 4,603,209; U.S. Pat. No. 5,049,673; U.S. Pat. No. 4,849,362; U.S. Pat. No. 5,453,517; U.S. Pat. No. 5,501,980; U.S. Pat. No. 5,459,276; U.S. Pat. No. 5,501,980; U.S. Pat. No. 5,459,276; and U.S. Pat. No. 5,516,911; each of which is hereby incorporated by reference). Fluorescein-based fluorescent calcium indicators (such as Fluo-3 and Fluo-4) are the most common fluorescent indicators used in biological assays. However, these existing xanthene-based calcium indicators typically have either small cell-induced excitation and fluorescence wavelength change, and/or low calcium-induced fluorescence enhancement, resulting in low detection sensitivity and high assay background. In addition, the existing xanthene-based calcium indicators have short emission wavelength, which often interferes with the fluorescence of some agonists and/or antagonists to be screened. Another drawback is resulted from the spontaneous hydrolysis of monoalkylated fluorescein-based indicators in cell medium, generating significant assay background.

In view of the existing drawbacks for currently used fluorescein-based fluorescent calcium indicators, what is needed are improved compositions and methods that offer sensitive detection of small variations in calcium and other ion concentrations, with a rapid response and a strong fluorescence signal. Also needed are fluorescent indicators that can be readily loaded into live cells with large spectral shift and fluorescence enhancement. Another preferable property is that the indicators have emission at longer wavelength to reduce the interference from the fluorescence of agonists and antagonist that often have fluorescence at short wavelength. In addition, compositions and methods that are less susceptible to the effects of external changes (such as temperature) are preferred for high throughput screening and high content analysis.

The present application is directed to a family of fluorescent dyes that are useful for preparing fluorescent metal ion indicators. The indicators include a carbofluorescein lactone fluorophore that is incorporated with an ionophore, and are useful for the detection, discrimination and quantification of metal cations. The fluorescent indicators of this invention demonstrate unexpected larger spectral shift upon cell-induced hydrolysis, unexpected emission shift to the longer wavelength, better stability in the presence of cells and better cellular retention compared to the existing fluorescein ion indicators.

DEFINITIONS

Figure 1:
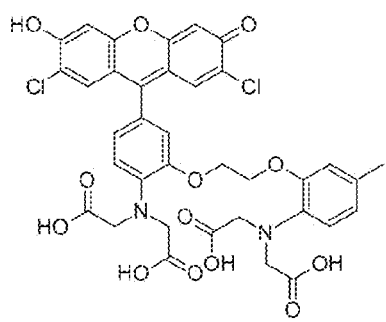
FIG. 1. The chemical structures of Fluo-3, Fluo-3 AM, Fluo-4 and Fluo-4 AM.
Figure 1:
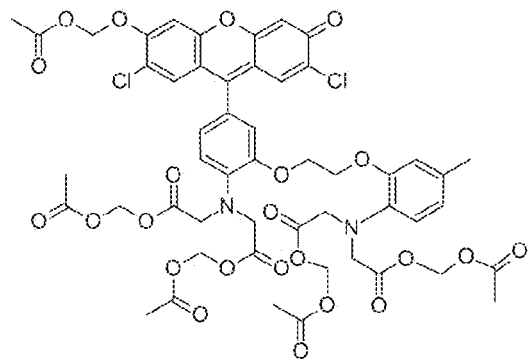
Figure 1:
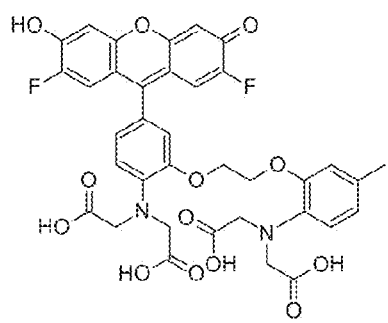
Figure 1:
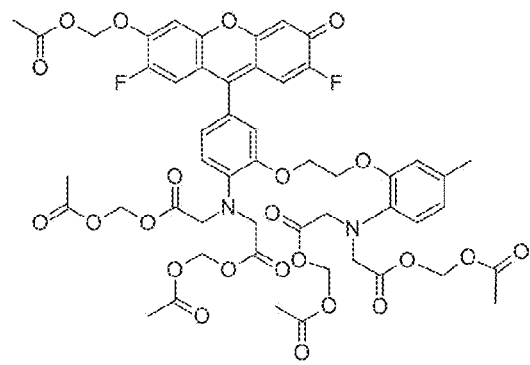

The following definitions are set forth to illustrate and define the meaning and scope of the various terms used to describe the invention herein.

The term "organic substituent", as used herein, refers to a carbon-containing organic radical that incorporates straight, branched chain or cyclic radicals having up to 50 carbons, unless the chain length or ring size is limited thereto. The organic substituent may include one or more elements of unsaturation, such as carbon-carbon double or triple bonds. Organic substituents may include alkyl, alkylene, alkenyl, alkenylene and alkynyl moieties, among others.

The term "alkyl," as used herein, by itself or as part of another group, refers to straight, branched chain or cyclic radicals having up to 50 carbons, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others.

The term "alkylene," as employed herein, by itself or as part of another group, refers to straight, branched chain or cyclic divalent radicals having up to 50 carbons, unless the chain length or ring size is limited thereto. Typical examples include methylene (—$CH_2$—), ethylene (—$CH_2CH_2$—), propylene, butylene, pentylene, hexylene, heptylene, octylene, nonylene, and decylene, among others.

The term "alkenyl," as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene," as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH═CH—), propenylene (—CH═$CHCH_2$— and —$CH_2$CH═CH—), n-butenylene, and 3-methyl-2-pentenylene, hexenylene, heptenylene, octenylene, nonenylene, and decenylene, among others.

The term "alkynyl," as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—), propynylene (—C≡$CCH_2$— and —$CH_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—$OCH_2CH_2O$—) or alkyl moieties that contain more than one oxygen atom.

The term "aryl," as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl.

The term "heteroaryl," as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "AM ester" or "AM" as employed herein, by itself or as part of another group, refers to an acetoxymethyl ester of a carboxylic acid or a phenol.

The terms "amino" or "amine" include $NH_2$, "monoalkylamine" or "monoalkylamino," and "dialkylamine" or "dialkylamino" The terms "monoalkylamine" and "monoalkylamino," "dialkylamine" and "dialkylamino as employed herein, by itself or as part of another group, refers to the group $NH_2$ where one hydrogen has been replaced by an alkyl group, as defined above.

The terms "dialkylamine" and "dialkylamino" as employed herein, by itself or as part of another group, refers to the group $NH_2$ where both hydrogens have been replaced by alkyl groups, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

The term "chelator", "chelate", "chelating group", "ionophore", or "ionophoric moiety" as used herein, by itself or as part of another group, refers to a chemical moiety that binds to, or complexes with, one or more metal ions, such as lithium, calcium, sodium, magnesium, zinc, potassium, and/or other biologically important metal ions. The binding affinity of a chelator for a particular metal ion can be determined by measuring the dissociation constant between that chelator and that ion. Chelators may include one or more chemical moieties that bind to, or complex with, a cation or anion. Examples of suitable chelators include 1,2-bis(2-aminophenoxy)ethane-N,N,N',N'-tetraacetic acid (BAPTA), bipyridyl (bipy); terpyridyl (terpy); ethylenediaminetetraacetic acid (EDTA); crown ethers; aza-crown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; glyme; diglyme; bis(acetylacetonate)ethylenediamine (acacen); 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTA), 1,4,8,11-tetraazacyclotetra-decanetetraacetic acid (TETA), DOTA-N-(2-aminoethyl) amide; DOTA-N-(2-aminophenethyl)amide; and 1,4,8,11-tetraazacyclotetradecane, among others.

The term "BAPTA" or "1,2-bis(2-aminophenoxy)ethane-N,N,N'N'-tetraacetic acid" as used herein, by itself or as part of another group, refers to the following ring structure or its derivatives, such as esters, amides, carbamates and so on:

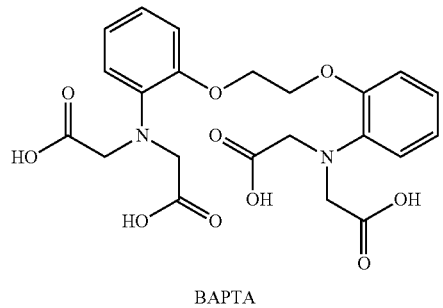 [SMILES: O=C(O)CN(CC(=O)O)c1ccccc1OCCOc1ccccc1N(CC(=O)O)CC(=O)O]

BAPTA

The term "fluorophore or fluorophore moiety" as used herein, by itself or as part of another group, means a molecule or a portion of a molecule which exhibits fluorescence. By fluorescence is meant that the molecule or portion of a molecule can absorb excitation energy having a given wavelength and emit energy at a different wavelength. The intensity and wavelength of the emitted energy depend on the fluorophore, the chemical environment of the fluorophore, and the specific excitation energy used. Exemplary fluorophores include, but are not limited to, fluoresceins, rhodamines, coumarins, oxazines, cyanines, pyrenes, and other polycyclic aromatic molecules.

The term "xanthene", or "xanthene derivative", as used herein, by itself or as part of another group, means any compounds or substituents that contain one or more of the following fused ring structures or its derivatives:

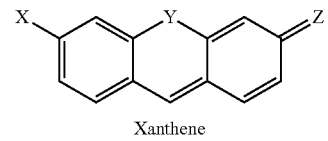

Xanthene
(X, Z = O, S or Se or N; Y = O, S, Se, N, C or Si)

The term "fluorescein" as used herein, by itself or as part of another group, means any compounds or substituents that contain one or more of the following fused ring structures or its derivatives:

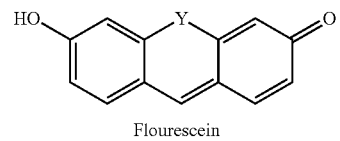

Flourescein
(Y = O, S, Se, N, C or Si)

The term "carbofluorescein" as used herein, by itself or as part of another group, means any compounds or substituents that contain one or more of the following fused ring structures or its derivatives:

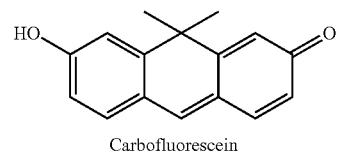

Carbofluorescein

The term "carbofluorescein lactone" as used herein, by itself or as part of another group, means any compounds or substituents that contain one or more of the following fused ring structures or its derivatives:

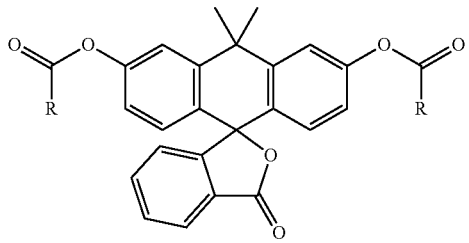

Carbofluorescein Lactone

The term "substituted," as used herein, refers to the formal replacement of a hydrogen on a chemical moiety or functional group with an alternative radical. Where a compound, chemical moiety or functional group is described as substituted, the alternative radical substituent moiety is generally selected from the group consisting of hydroxy, oxo, nitro, trifluoromethyl, halogen, alkoxy, alkylenedioxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, dialkylaminoalkoxymono(carboxyalkyl)amino, bis(carboxy-alkyl)amino, alkoxycarbonyl, alkynylcarbonyl, alkylsulfonyl, alkenylsulfonyl, alkynylsulfonyl, arylsulfonyl, alkylsulfinyl, alkylsulfonamido, arylsulfonamido, carboxyalkoxy, carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl.

The term "indicator compound" refers to the compounds of the invention, specifically to those compounds having utility as fluorescent metal ion indicators, as well as their acylated or otherwise protected precursor compounds, such as the acetoxymethyl ester derivatives suitable for adding to samples containing biological cells.

The term "screening" refers to the testing and/or evaluation of a multiplicity of molecules or compounds for a selected property or therapeutic utility. Screening is typically a repetitive, or iterative process. A multiplicity of candidate molecules may be screened for their ability to bind to a target molecule which is capable of denaturing and/or unfolding. For example, a multiplicity of candidate molecules may be evaluated for their ability to bind to a target molecule (e.g., a protein receptor) in a thermal shift assay. If none of a selected subset of molecules from the multiplicity of candidate molecules (for example, a combinatorial library) binds to the target molecule, then a different subset may be tested for binding in the thermal shift assay.

The term "high-throughput", as used herein, encompasses screening activity in which human intervention is minimized, and automation is maximized. For example, high-throughput screening may include any of a variety of automated processes, including for example the automation of pipetting, mixing, and/or heating, the software-controlled generation of thermal unfolding information, and the software-controlled comparisons of thermal unfolding information. Alternatively, a high-throughput method is one in which hundreds of compounds can be screened per 24 hour period by a single individual operating a single suitable apparatus.

DESCRIPTION OF THE PREFERRED EMBODIMENTS

The present application is directed to fluorescent dyes useful for preparing fluorescent metal ion indicators, the fluorescent indicators themselves, and the use of the fluorescent indicators for the detection, discrimination and quantification of metal cations.

In one aspect of the invention, the compounds of the invention may be described by Formula 1:

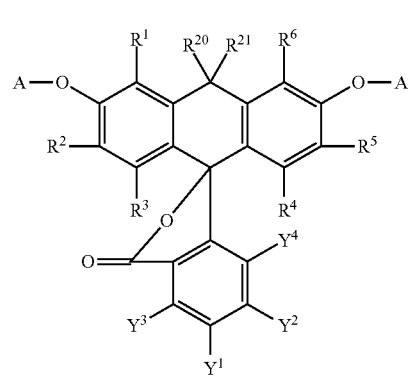

Formula 1

In this embodiment, A is acyl or acyloxymethyl; $R^1$-$R^7$ are independently H, alkyl, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $Y^1$ and $Y^2$, $Y^1$ and $Y^3$ or $Y^2$ and $Y^4$ form a metal ion chelator in combination with C, H, N, O or S atoms provided that at least one of $Y^1$ $Y^2$, and $Y^3$ is NH, N-alkyl or N(CH$_2$)$_n$COOCH$_2$OAc wherein n is 1-10.

In another aspect, A is acetyl; $R^1$-$R^7$ are independently H, alkyl, halogen, carboxy, aryl or heteroaryl; $R^{20}$ and $R^{21}$ are independently alkyl, aryl or heteroaryl; $Y^1$ and $Y^2$ or $Y^1$ and $Y^3$ combine to form a cell-permeable metal ion-chelating moiety.

In another aspect, A is acetyl or acetoxymethyl; $R^1$-$R^7$ are independently H, alkyl, halogen, carboxy, aryl or heteroaryl; $R^{20}$ and $R^{21}$ are independently alkyl, aryl or heteroaryl; $Y^1$ and $Y^2$ or $Y^1$ and $Y^3$ combine to form a cell-permeable metal ion-chelating crown ether moiety.

In another aspect, A is acetyl; $R^1$-$R^7$ are independently H, alkyl, halogen, aryl or heteroaryl; $R^{20}$ and $R^{21}$ are independently alkyl, aryl or heteroaryl; $Y^1$ and $Y^2$ or $Y^1$ and $Y^3$ combine to form a cell-permeable metal ion-chelating azacrown ether moiety.

In another aspect, A is acetyl; $R^1$-$R^7$ are independently H, alkyl, halogen, carboxy, aryl or heteroaryl; $R^{20}$ and $R^{21}$ are independently alkyl, aryl or heteroaryl; $Y^1$ and $Y^2$ or $Y^1$ and $Y^3$ combine to form a cell-permeable metal ion-chelating cryptand moiety.

In another aspect of the invention, the compounds of the invention may be described by Formula 2:

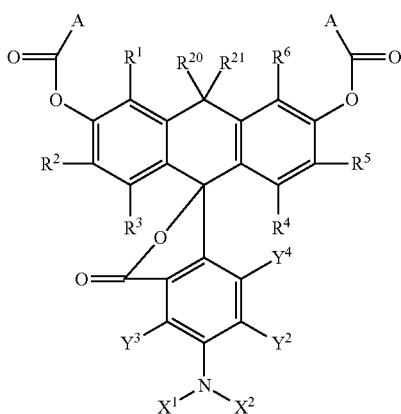

Formula 2

In this embodiment, substituents $R^1$-$R^6$ and $Y^4$ are independently H, alkyl, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $X^1$, $X^2$ and $Y^2$, or $X^1$, $X^2$ and $Y^3$ combine to form a metal ion-chelating moiety; A is an alkyl having 1-10 carbons. In certain embodiments, A is methyl.

In another aspect of the invention, A is methyl; $R^1$-$R^6$ and $Y^4$ are independently H, alkyl, halogen, carboxy, aryl or heteroaryl; $R^{20}$ and $R^{21}$ are independently alkyl, aryl or heteroaryl; $X^1$, $X^2$ and $Y^2$ or $X^1$, $X^2$ and $Y^3$ combine to form a metal ion-chelating moiety.

In another aspect of the invention, A is methyl; $R^1$-$R^6$ and $Y^4$ are independently H, alkyl, fluoro or chloro; $R^{20}$ and $R^{21}$ are methyl; $X^1$, $X^2$ and $Y^2$, or $X^1$, $X^2$ and $Y^3$ combine to form a metal ion-chelating moiety.

In another aspect of the invention, the compounds of the invention may be described by Formula 3:

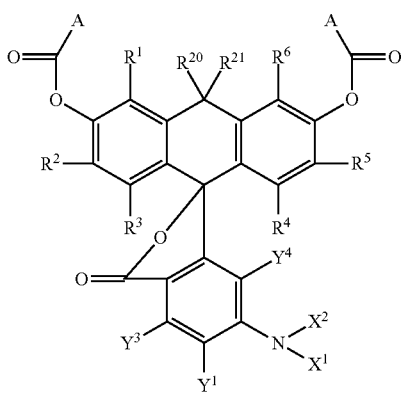

Formula 3

In this embodiment, substituents $R^1$-$R^6$ and $Y^3$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $X^1$, $X^2$ and $Y^1$ or $X^1$, $X^2$ and $Y^4$ combine to form a metal ion-chelating moiety; A is an alkyl having 1-10 carbons. In certain embodiments, A is methyl.

In another aspect of the invention, A is methyl; $R^1$-$R^6$ and $Y^3$ are independently H, alkyl, halogen, carboxy, aryl or heteroaryl; $R^{20}$ and $R^{21}$ are independently alkyl, aryl or heteroaryl; $X^1$, $X^2$ and $Y^1$ combine to form a metal ion-chelating moiety.

In another aspect of the invention, A is methyl; $R^1$-$R^6$ and $Y^3$ are independently H, alkyl, fluoro or chloro; $R^{20}$ and $R^{21}$ are methyl; $X^1$, $X^2$ and $Y^1$ or $X^1$, $X^2$ and $Y^4$ combine to form a metal ion-chelating moiety.

In another aspect of the invention, the compounds of the invention may be described by Formula 4:

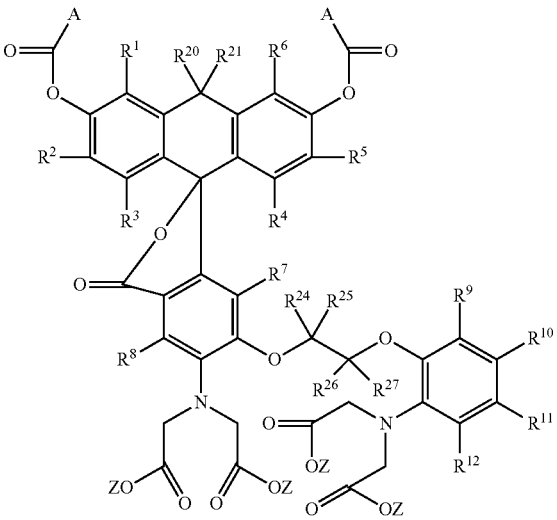

Formula 4

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{24}$-$R^{27}$ are independently hydrogen, alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl; Z is an acyloxymethyl having 3-10 carbons.

In another aspect of the invention, A is alkyl; $R^1$-$R^{12}$ are independently H, alkyl, aryl or halogen; $R^{20}$ and $R^{21}$ are independently alkyl, aryl or heteroaryl; $R^{24}$-$R^{27}$ are independently hydrogen, alkyl or aryl; Z is an acyloxymethyl having 3-10 carbons.

In another aspect of the invention, A is methyl; $R^1$-$R^{12}$ are independently H, alkyl, fluoro or chloro; $R^{20}$ and $R^{21}$ are methyl; $R^{24}$-$R^{27}$ are independently hydrogen or alkyl; Z is acetoxymethyl.

In another aspect of the invention, the compounds of the invention may be described by Formula 5:

Formula 5

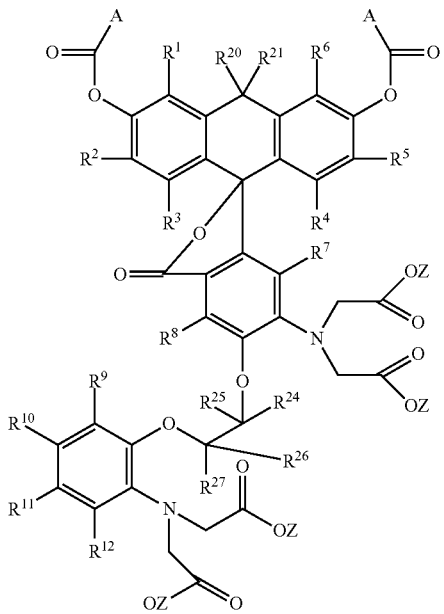

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$-$R^{27}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl; Z is an acyloxymethyl having 3-10 carbons.

In another aspect of the invention, A is alkyl; $R^1$-$R^{12}$ are independently H, alkyl, aryl or halogen; $R^{20}$ and $R^{21}$ are independently alkyl, aryl or heteroaryl; $R^{24}$-$R^{27}$ are independently hydrogen, alkyl or aryl; Z is an acyloxymethyl having 3-10 carbons.

In another aspect of the invention, A is methyl; $R^1$-$R^{12}$ are independently H, alkyl, fluoro or chloro; $R^{20}$ and $R^{21}$ are methyl; $R^{24}$-$R^{27}$ are independently hydrogen or alkyl; Z is acetoxymethyl.

In another aspect of the invention, the compounds of the invention may be described by Formula 6:

Formula 6

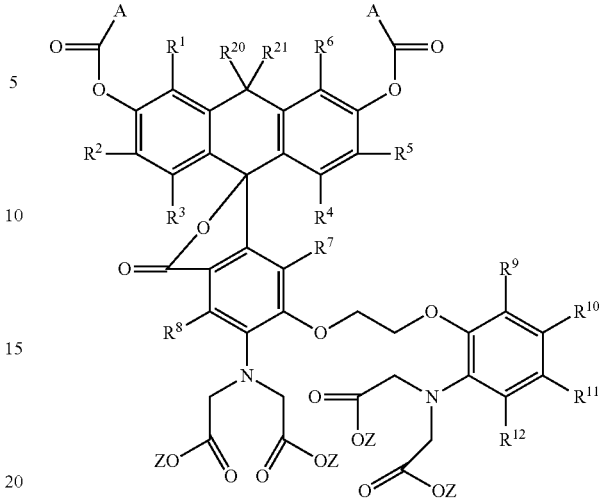

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl; Z is an acyloxymethyl having 3-10 carbons. In certain embodiments, Z is acetoxymethyl.

In another aspect of the invention, A is alkyl; $R^1$-$R^{12}$ are independently H, alkyl, aryl or halogen; $R^{20}$ and $R^{21}$ are independently alkyl, aryl or heteroaryl; A is methyl; Z is acetoxymethyl.

In another aspect of the invention, A is methyl; $R^1$-$R^{12}$ are independently H, alkyl, fluoro or chloro; $R^{20}$ and $R^{21}$ are methyl; Z is acetoxymethyl.

In some embodiments, the compound is described by Formula 17:

Formula 17

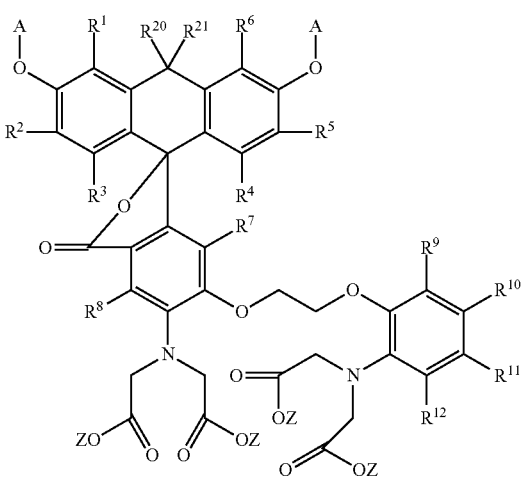

wherein $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an acyl or an acyloxymethyl having 1-10 carbons; and Z is an acyloxymethyl having 3-10 carbons.

In some embodiments of Formula 17, A is acetyl or acetoxymethyl. In certain embodiments of Formula 17, A is acetyl and Z is an acyloxymethyl having 3-10 carbons. In certain embodiments of Formula 17, Z is acetoxymethyl.

In some embodiments of Formula 17, A is acetyl. In some embodiments of Formula 17, $R^1$-$R^{12}$ are independently H, alkyl, aryl or halogen; $R^{20}$ and $R^{21}$ are independently alkyl, aryl or heteroaryl; and Z is acetoxymethyl.

In some embodiments of Formula 17, A is acetyl; $R^1$-$R^{12}$ are independently H, alkyl, fluoro or chloro; $R^{20}$ and $R^{21}$ are methyl; and Z is acetoxymethyl.

In some embodiments, the compound is described by Formula 18:

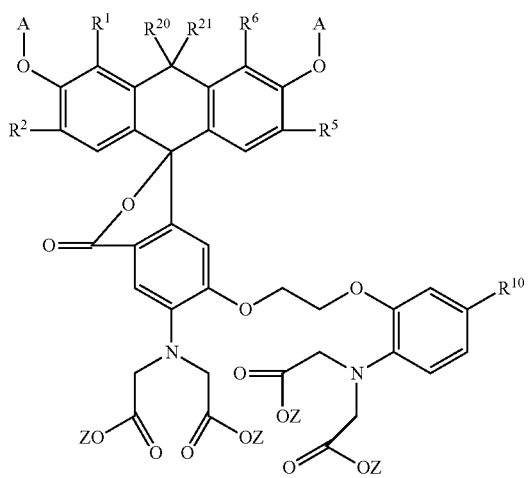

Formula 18 wherein $R^1$, $R^2$, $R^5$, $R^6$ and $R^{10}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an acyl or an acyloxymethyl having 1-10 carbons; and Z is an acyloxymethyl having 3-10 carbons.

In some embodiments of Formula 18, A is acetyl or acetoxymethyl. In certain embodiments of Formula 18, A is acetyl and Z is an acyloxymethyl having 3-10 carbons. In certain embodiments of Formula 18, Z is acetoxymethyl.

In some embodiments of Formula 18, A is acetyl. In some embodiments of Formula 18, $R^1$, $R^2$, $R^5$, $R^6$ and $R^{10}$ are independently H, alkyl, aryl or halogen; $R^{20}$ and $R^{21}$ are independently alkyl, aryl or heteroaryl; and Z is acetoxymethyl.

In some embodiments of Formula 18, A is acetyl; $R^1$, $R^2$, $R^5$, $R^6$ and $R^{10}$ are independently H, alkyl, fluoro or chloro; $R^{20}$ and $R^{21}$ are methyl; and Z is acetoxymethyl.

In some embodiments, the compound is described by Formula 19:

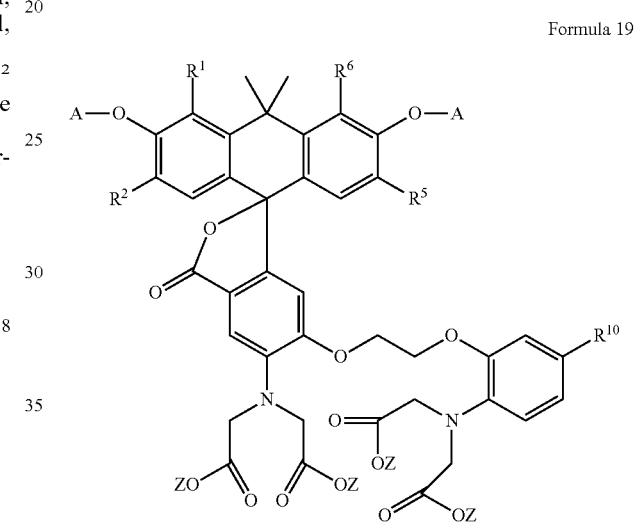

Formula 19 wherein $R^1$, $R^2$, $R^5$, $R^6$ and $R^{10}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an acyl or an acyloxymethyl having 1-10 carbons; and Z is an acyloxymethyl having 3-10 carbons.

In some embodiments of Formula 19, A is acetyl or acetoxymethyl. In certain embodiments of Formula 19, A is acetyl and Z is an acyloxymethyl having 3-10 carbons. In certain embodiments of Formula 19, Z is acetoxymethyl.

In some embodiments of Formula 19, A is acetyl. In some embodiments of Formula 19, $R^1$, $R^2$, $R^5$, $R^6$ and $R^{10}$ are independently H, alkyl, aryl or halogen; and Z is acetoxymethyl.

In some embodiments of Formula 19, A is acetyl; $R^1$, $R^2$, $R^5$, $R^6$ and $R^{10}$ are independently H, alkyl, fluoro or chloro; and Z is acetoxymethyl. In some embodiments of Formula 19, A is acetoxymethyl; $R^1$, $R^2$, $R^5$, $R^6$ and $R^{10}$ are independently H, alkyl, fluoro or chloro; and Z is acetoxymethyl.

In some embodiments, the compound is described by Formula 20:

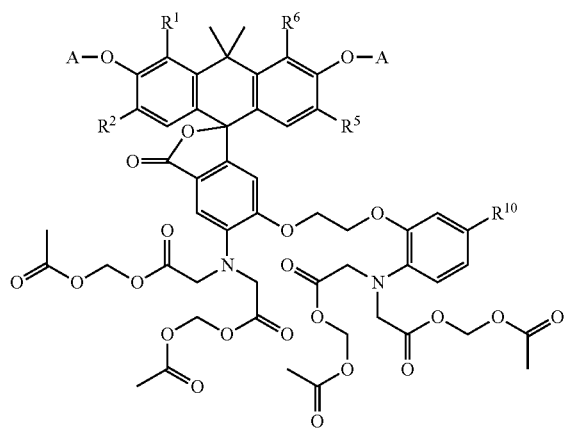

Formula 20 wherein A is acetyl or acetoxymethyl; $R^1$, $R^2$, $R^5$ and $R^6$ are independently hydrogen, chloro or fluoro; and $R^{10}$ is hydrogen, chloro, fluoro, nitro, methyl, ethyl, propyl, butyl, pentyl or hexyl.

In some embodiments of Formula 20, A is acetyl or acetoxymethyl. In certain embodiments of Formula 20, A is acetyl. In certain embodiments of Formula 20, A is acetoxymethyl.

In some embodiments of Formula 20, $R^2$ and $R^5$ are chloro. In some embodiments of Formula 20, $R^1$ and $R^6$ are chloro. In certain embodiments of Formula 20, $R^1$, $R^2$, $R^5$ and $R^6$ are each chloro. In some embodiments of Formula 20, $R^2$ and $R^5$ are fluoro. In some embodiments of Formula 20, $R^1$ and $R^6$ are fluoro. In certain embodiments of Formula 20, $R^1$, $R^2$, $R^5$ and $R^6$ are each fluoro.

In some embodiments of Formula 20, $R^{10}$ is hydrogen. In certain embodiments of Formula 20, $R^{10}$ is methyl.

In certain embodiments of Formula 20, A is acetyl, $R^2$ and $R^5$ are chloro, $R^1$ and $R^6$ are hydrogen, and $R^{10}$ is methyl.

In certain embodiments of Formula 20, A is acetyl, $R^2$ and $R^5$ are fluoro, $R^1$ and $R^6$ are hydrogen, and $R^{10}$ is methyl.

In certain embodiments of Formula 20, A is acetyl, $R^2$ and $R^5$ are chloro, $R^1$ and $R^6$ are chloro, and $R^{10}$ is hydrogen.

In certain embodiments of Formula 20, A is acetoxymethyl, $R^2$ and $R^5$ are chloro, $R^1$ and $R^6$ are hydrogen, and $R^{10}$ is methyl.

In another aspect of the invention, the compounds of the invention may be described by Formula 7:

Formula 7

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl; Z is an acyloxymethyl having 3-10 carbons. In certain embodiments, Z is acetoxymethyl.

In another aspect of the invention, A is alkyl; $R^1$-$R^{12}$ are independently H, alkyl, aryl or halogen; $R^{20}$ and $R^{21}$ are independently alkyl, aryl or heteroaryl; Z is acetoxymethyl.

In another aspect of the invention, A is methyl; $R^1$-$R^{12}$ are independently H, alkyl, fluoro or chloro; $R^{20}$ and $R^{21}$ are methyl; Z is acetoxymethyl.

In another aspect of the invention, the compounds of the invention may be described by Formula 8:

Formula 8

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{24}$-$R^{29}$ are independently hydrogen, alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl; Z is an acyloxymethyl having 3-10 carbons.

In another aspect of the invention, A is alkyl; $R^1$-$R^{12}$ are independently H, alkyl, aryl or halogen; $R^{20}$ and $R^{21}$ are independently alkyl, aryl or heteroaryl; $R^{24}$-$R^{29}$ are independently hydrogen, alkyl or aryl; Z is an acyloxymethyl having 3-10 carbons.

In another aspect of the invention, A is methyl; $R^1$-$R^{12}$ are independently H, alkyl, fluoro or chloro; $R^{20}$ and $R^{21}$ are methyl; $R^{24}$-$R^{29}$ are independently hydrogen or alkyl; Z is acetoxymethyl.

In another aspect of the invention, the compounds of the invention may be described by Formula 9:

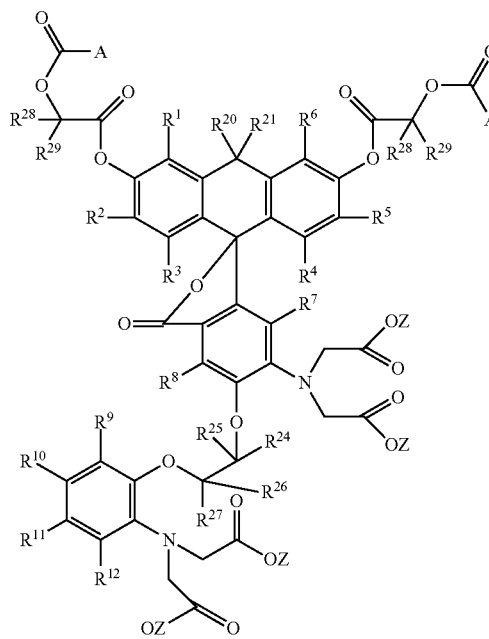

Formula 9

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$-$R^{29}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl; Z is an acyloxymethyl having 3-10 carbons.

In another aspect of the invention, A is alkyl; $R^1$-$R^{12}$ are independently H, alkyl, aryl or halogen; $R^{20}$ and $R^{21}$ are independently alkyl, aryl or heteroaryl; $R^{24}$-$R^{29}$ are independently hydrogen, alkyl or aryl; Z is an acyloxymethyl having 3-10 carbons.

In another aspect of the invention, A is methyl; $R^1$-$R^{12}$ are independently H, alkyl, fluoro or chloro; $R^{20}$ and $R^{21}$ are methyl; $R^{24}$-$R^{29}$ are independently hydrogen or alkyl; Z is acetoxymethyl.

In another aspect of the invention, the compounds of the invention may be described by Formula 10:

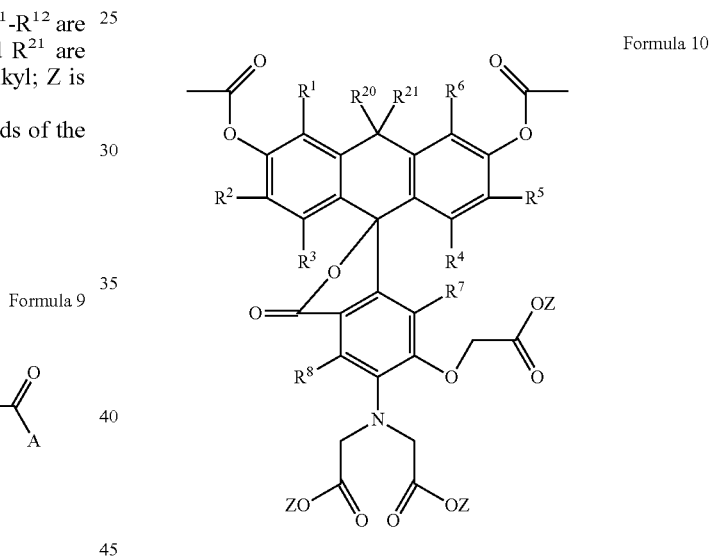

Formula 10

In this embodiment, substituents $R^1$-$R^8$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; Z is an acyloxymethyl having 3-10 carbons.

In another aspect of the invention, A is alkyl; $R^1$-$R^8$ are independently H, alkyl, aryl or halogen; $R^{20}$ and $R^{21}$ are independently alkyl, aryl or heteroaryl; Z is an acyloxymethyl having 3-10 carbons.

In another aspect of the invention, A is methyl; $R^1$-$R^8$ are independently H, alkyl, fluoro or chloro; $R^{20}$ and $R^{21}$ are methyl; Z is acetoxymethyl.

In another aspect of the invention, the compounds of the invention may be described by Formula 11:

Formula 11

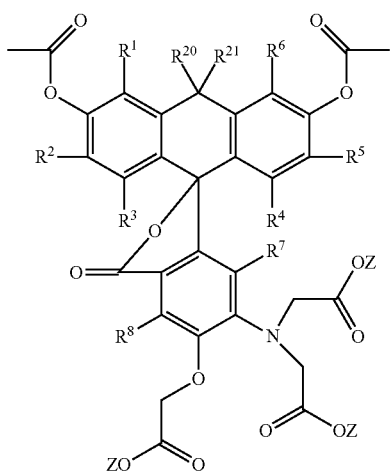

In this embodiment, substituents $R^1$-$R^8$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl; Z is an acyloxymethyl having 3-10 carbons.

In another aspect of the invention, A is alkyl; $R^1$-$R^8$ are independently H, alkyl, aryl or halogen; $R^{20}$ and $R^{21}$ are independently alkyl, aryl or heteroaryl; Z is an acyloxymethyl having 3-10 carbons.

In another aspect of the invention, A is methyl; $R^1$-$R^8$ are independently H, alkyl, fluoro or chloro; $R^{20}$ and $R^{21}$ are methyl; Z is acetoxymethyl.

In another aspect of the invention, the compounds of the invention may be described by Formula 12:

Formula 12

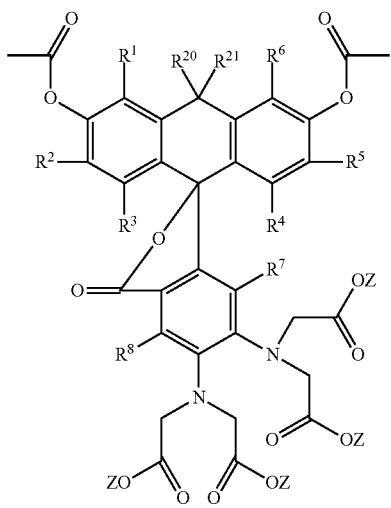

In this embodiment, substituents $R^1$-$R^8$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; Z is an acyloxymethyl having 3-10 carbons.

In another aspect of the invention, A is alkyl; $R^1$-$R^8$ are independently H, alkyl, aryl or halogen; $R^{20}$ and $R^{21}$ are independently alkyl, aryl or heteroaryl; Z is an acyloxymethyl having 3-10 carbons.

In another aspect of the invention, A is methyl; $R^1$-$R^8$ are independently H, alkyl, fluoro or chloro; $R^{20}$ and $R^{21}$ are methyl; Z is acetoxymethyl.

In another aspect of the invention, the compounds of the invention may be described by Formula 13:

Formula 13

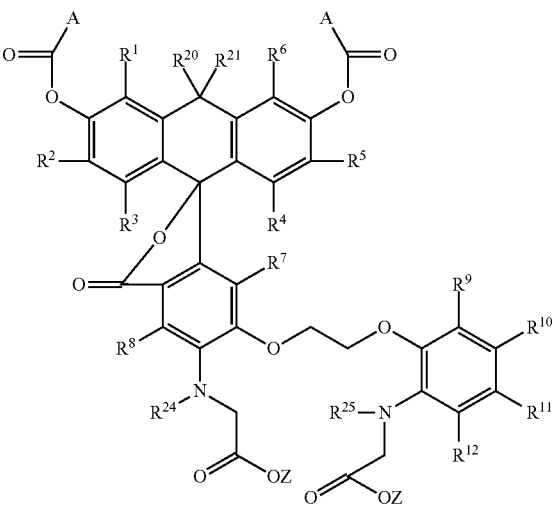

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{24}$ and $R^{25}$ are independently hydrogen, alkyl, carboxymethyl or acetoxymethoxylenecarbonylmethyl; A is an alkyl having 1-10 carbons. In certain embodiments, A is methyl; Z is an acyloxymethyl having 3-10 carbons. In certain embodiments, Z is acetoxymethyl.

In another aspect of the invention, A is alkyl; $R^1$-$R^{12}$ are independently H, alkyl, aryl or halogen; $R^{20}$ and $R^{21}$ are independently alkyl, aryl or heteroaryl; $R^{24}$ and $R^{25}$ are independently hydrogen, alkyl or acetoxymethoxylenecarbonylmethyl; A is methyl; Z is acetoxymethyl.

In another aspect of the invention, A is methyl; $R^1$-$R^{12}$ are independently H, alkyl, fluoro or chloro; $R^{20}$ and $R^{21}$ are methyl; $R^{24}$ and $R^{25}$ are independently hydrogen, or acetoxymethoxylenecarbonylmethyl; $R^{24}$ and $R^{25}$ are a acetoxymethoxylenecarbonylmethyl; Z is acetoxymethyl.

In another aspect of the invention, the compounds of the invention may be described by Formula 14:

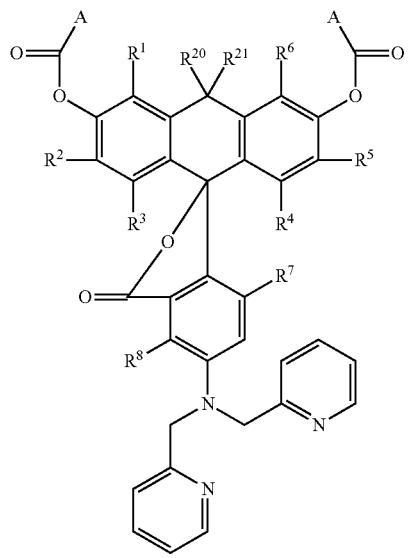

Formula 14

In this embodiment, substituents $R^1$-$R^8$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl.

In another aspect of the invention, A is alkyl; $R^1$-$R^8$ are independently H, alkyl, aryl or halogen; $R^{20}$ and $R^{21}$ are independently alkyl, aryl or heteroaryl.

In another aspect of the invention, A is methyl; $R^1$-$R^8$ are independently H, alkyl, fluoro or chloro; $R^{20}$ and $R^{21}$ are methyl.

In another aspect of the invention, the compounds of the invention may be described by Formula 15:

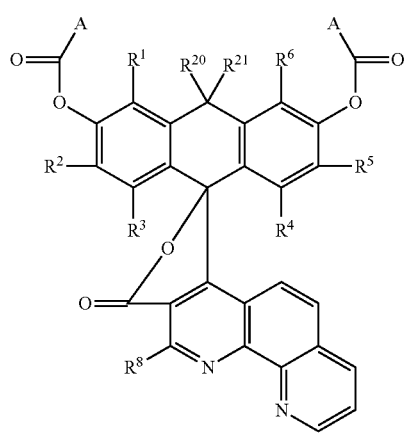

Formula 15

In this embodiment, substituents $R^1$-$R^8$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons. In certain embodiments, A is methyl.

In another aspect of the invention, the compounds of the invention may be described by Formula 15:

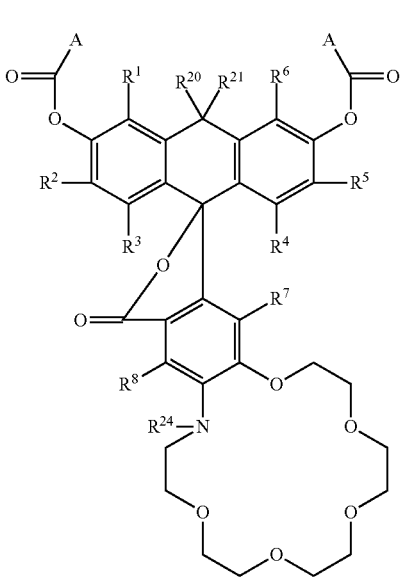

Formula 15

In this embodiment, substituents $R^1$-$R^8$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{24}$ is hydrogen, alkyl, carboxymethyl or acetoxymethoxylenecarbonylmethyl; A is an alkyl having 1-10 carbons.

In another aspect of the invention, A is methyl; $R^1$-$R^8$ are independently H, alkyl, aryl or halogen; $R^{20}$ and $R^{21}$ are independently alkyl, aryl or heteroaryl; $R^{24}$ is hydrogen, alkyl, carboxymethyl or acetoxymethoxylenecarbonylmethyl.

In another aspect of the invention, A is methyl; $R^1$-$R^8$ are independently H, alkyl, fluoro or chloro; $R^{20}$ and $R^{21}$ are methyl; $R^{24}$ is acetoxymethoxylenecarbonylmethyl.

In another aspect of the invention, the compounds of the invention may be described by Formula 16:

Formula 16

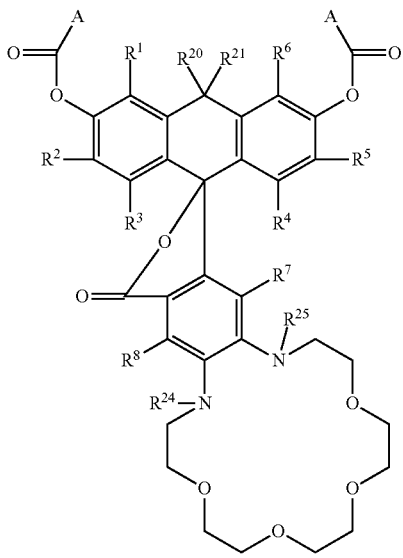

In this embodiment, substituents $R^1$-$R^8$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; $R^{20}$ and $R^{21}$ are independently alkyl, carboxyalkyl, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons; $R^{24}$ and $R^{25}$ are independently hydrogen, alkyl, carboxymethyl or acetoxymethoxylenecarbonylmethyl.

In another aspect of the invention, A is methyl; $R^1$-$R^8$ are independently H, alkyl, aryl or halogen; $R^{20}$ and $R^{21}$ are independently alkyl, aryl or heteroaryl; $R^{24}$ and $R^{25}$ are independently hydrogen, alkyl, carboxymethyl or acetoxymethoxylenecarbonylmethyl.

In another aspect of the invention, A is methyl; $R^1$-$R^8$ are independently H, alkyl, fluoro or chloro; $R^{20}$ and $R^{21}$ are methyl; $R^{24}$ and $R^{25}$ are acetoxymethoxylenecarbonylmethyl.

The fluorophore moiety can be any compound described by any of Formulas 1-16 that exhibits an absorption maximum beyond 500 nm upon esterase-induced hydrolysis, that is fused to a chelator, as described in greater detail below.

In one aspect of the invention, the fluorophore moiety has an absorption maximum beyond 500 nm. The fluorophore moiety is typically selected to confer its fluorescence properties on the indicator compound it is incorporated into. That is, the resulting indicator compound exhibits a detectable optical response when excited by energy having a wavelength at which that fluorophore absorbs as used herein, a detectable optical response means a change in, or occurrence of, an optical property that is detectable either by observation or instrumentally, such a change in absorption (excitation) wavelength, fluorescence emission wavelength, fluorescence emission intensity, fluorescence polarization, or fluorescence lifetime, among others.

In addition, the compounds of the invention preferably exhibit a detectable change in the optical response upon binding a target metal ion. Where the detectable response is a fluorescence response, the detectable change is typically a change in fluorescence, such as a change in the intensity, excitation or emission wavelength distribution of fluorescence, fluorescence lifetime, fluorescence polarization, or a combination thereof. In certain embodiments, the change in optical response upon binding the target metal ion is a change in fluorescence intensity that is greater than approximately 50-fold, more preferably greater than 100-fold.

Synthesis

The compounds of the invention may be prepared using any suitable synthetic schemes. The methodology used to prepare the compounds of the invention may involve a few components. The first component may involve the formation of the chelator, while the second may involve the modification of the chelator by forming a reactive functional group, covalently attaching a conjugate, or covalently attaching a fluorophore moiety to form the desired indicator compound. Although these synthetic components are typically performed in the order given, they may be carried out in any other suitable sequence. For example, a portion of the chelator may be derivatized with a fluorescent dye prior to formation of the complete chelator ring. The representative synthetic methods are summarized below. The other appropriate methods may also be adaped to synthesize the desired compounds of the invention.

As the metal binding ability of the resulting chelators may be significantly influenced by the nature of the amine substituents, careful selection of the alkylating agent may be necessary to prepare a reporter for a particular target ion. BAPTA chelators are typically selective for calcium ion. Where the chelator nitrogens are alkylated by methyl bromoacetate, the resulting bis-aza-crown ether is typically selective for sodium ions. If the alkylating agent is 2-picolyl chloride, the resulting crown ether is typically selective for zinc ions. EDTA derivatives are typically used for transitional metal ions. Selection of an alkylating agent that incorporates a precursor to a reactive functional group is useful for producing chemically reactive compounds of the invention, as well as acting as a useful intermediate for preparing conjugates, as described above.

The syntheses of chelating groups selective for different metal ions has been well described in the literature (U.S. Pat. No. 4,603,209; U.S. Pat. No. 5,049,673; U.S. Pat. No. 4,849,362; U.S. Pat. No. 5,453,517; U.S. Pat. No. 5,501,980; U.S. Pat. No. 5,459,276; U.S. Pat. No. 5,501,980; U.S. Pat. No. 5,459,276; U.S. Pat. No. 5,516,911; U.S. Application No. 2002/0164616; each of which is incorporated by reference). These methods can be readily adapted to prepare chelator intermediates useful for the synthesis of the compounds of the invention.

Synthesis of carbofluorescein dyes typically involves the condensation of properly substituted bisphenol with a carbonyl-containing moiety such as a phthalic acid derivative or benzaldehyde derivatives. In the synthesis of the carbofluorescein indicators of the invention, the desired bisphenol is condensed with a chelator intermediate that contains a carboxylic acid, anhydride or acyl halide bound directly to the chelating moiety. This synthetic method is illustrated in Scheme 1.

Scheme 1 (For clarity all the substitutes are not shown)

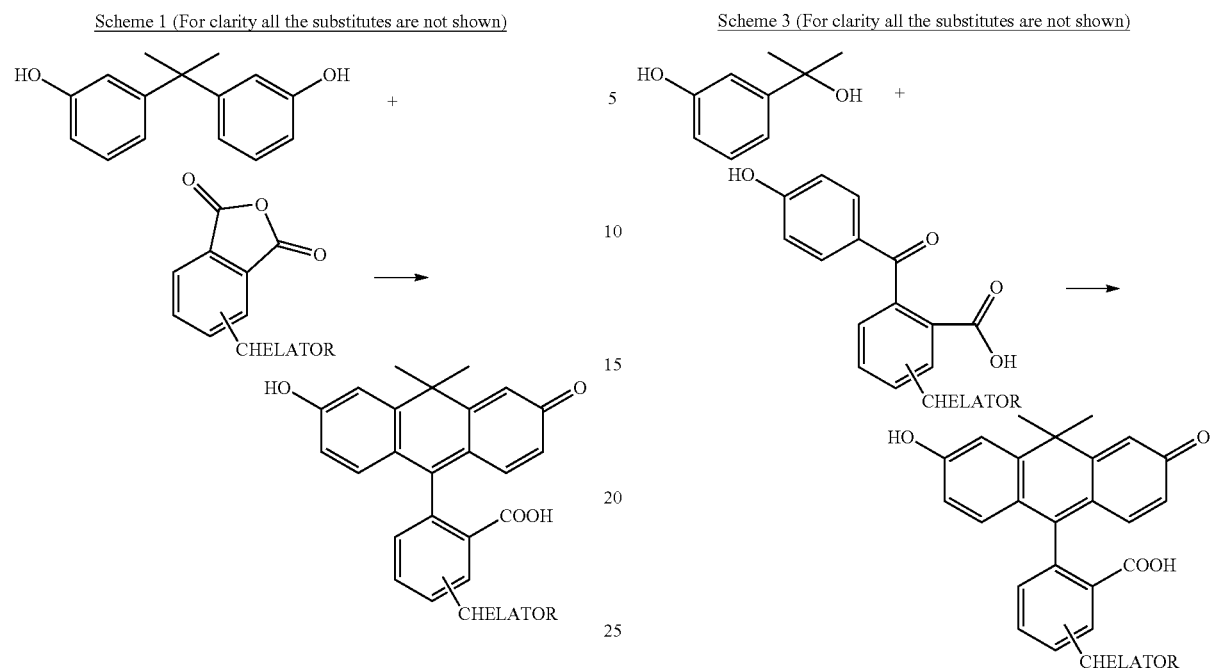

Under acidic conditions, the synthesis of carbofluorescein dyes might also be achieved from the condensation of properly substituted bisphenol with a 2-carboxybenaldehyde-containing moiety followed by air oxidation. In the synthesis of the carbofluorescein indicators of the invention, the desired bisphenol is condensed with a chelator intermediate that contains a 2-carboxybenaldehyde bound directly to the chelating moiety. This synthetic method is illustrated in Scheme 2.

Scheme 2 (For clarity all the substitutes are not shown)

The condensation of a properly substituted benzophenone with a desired 3-hydroxymethyphenol derivative can also provide a good access to carbofluorescein dyes. In this synthesis 3-hydroxyphenylstyryl can be a good alternative to the synthon of 3-hydroxymethyphenol derivative. This synthetic method is illustrated in Schemes 3 and 4.

Scheme 3 (For clarity all the substitutes are not shown)

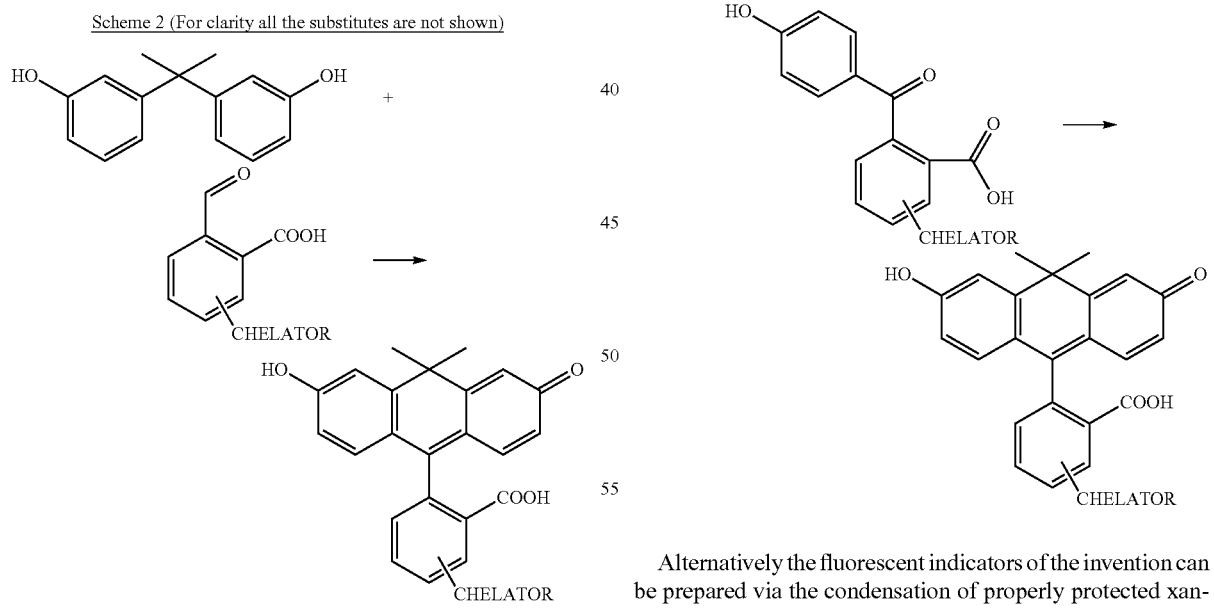

Scheme 4 (For clarity all the substitutes are not shown)

Alternatively the fluorescent indicators of the invention can be prepared via the condensation of properly protected xanthones with a chelator anion, typically prepared from the corresponding chelator bromide or iodide. This organometallic chemistry is also well described in the literature (C. Chen, R. Yeh and D. S. Lawrence, J. Am. Chem. Soc. 2002, 124, 3840; U.S. Pat. No. 5,049,673; Y. Urano, M. Kamiya, K. Kanda, T. Ueno, K. Hirose and T. Nagano, J. Am. Chem. Soc. 2005, 127, 4888) and can be readily adapted to synthesize the compounds of the invention. The protection and deprotection conditions are well described in the literature (C. J. Kocienski, Protecting Groups, 3$^{rd}$ Ed, Georg Thieme Verlag, 2005, pp 187-364 and pp 393-450; T. W. Greene and P. G. M. Wuts, Protective Groups in Organic Synthesis, 3$^{rd}$ Ed, John Wiley & Sons, 1999, pp 246-292 and pp 369-453). This synthetic method is illustrated in Scheme 5.

Scheme 5 (For clarity all the substitutes are not shown)

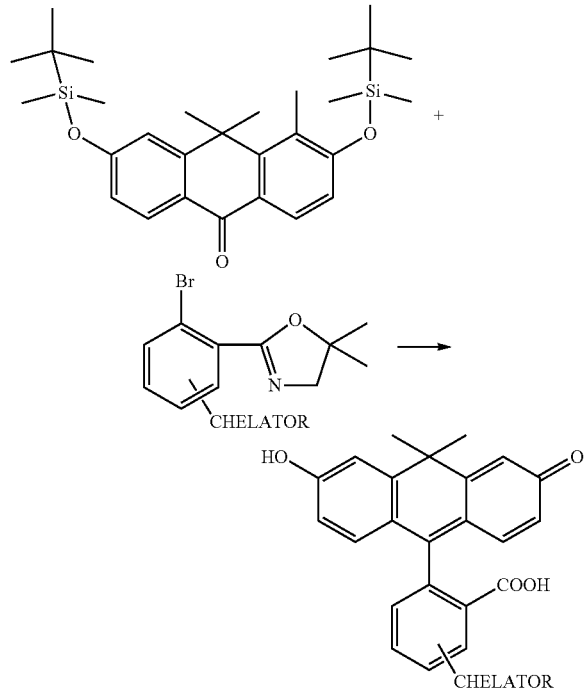

Post-condensation modifications of both the chelator and the fluorophore moiety are typically analogous to known methods of indicator modification. For example, the reduction of nitro substituents to amino groups, the conversion of carboxy substituents to cyano groups, and the preparation of esters of carboxylic acids, including acetoxymethyl esters. Additionally, a given salt or counterion of the indicators of the invention may be readily converted to other salts by treatment with ion-exchange resins, selective precipitation, and basification, as is well-known in the art.

Post-condensation modifications of phenol dyes are well known. For instance, the xanthenone portion of the dye can be halogenated by treatment with an appropriate halogenating agent, such as NCS, hypochlorite, sulfuryl chloride, bromine, NBS and iodine. Xanthenes containing unsaturated fused rings can be hydrogenated to the saturated derivatives.

The reduced and oxidized versions of the carbofluorescein indicators are freely interconvertible by well-known oxidation or reduction reagents, including borohydrides, aluminum hydrides, hydrogen/catalyst, and dithionites. Care must be exercised to select an oxidation or reducing agent that is compatible with the chelator used. A variety of oxidizing agents mediate the oxidation of dihydroxanthenes, including molecular oxygen in the presence or absence of a catalyst, nitric oxide, peroxynitrite, dichromate, triphenylcarbenium and chloranil. The dihydro carbofluoresceins may also be oxidized electrochemically, or by enzyme action, including the use of horseradish peroxidase in combination with peroxides or by nitric oxide.

APPLICATIONS OF THE FLUORESCENT INDICATORS OF THE INVENTION

The indicators disclosed herein possess particular utility for the detection and/or quantification of metal ions in a sample of interest. Such indicators may be useful for measuring ions in extracellular spaces; in vesicles; in vascular tissue of plants and animals; biological fluids such as blood and urine; in fermentation media; in environmental samples such as water, soil, waste water and seawater; and in chemical reactors. Optical indicators for ions are important for qualitative and quantitative determination of ions, particularly in living cells. Fluorescent indicators for metal cations also permit the continuous or intermittent optical determination of these ions in living cells, and in solutions containing the ions.

In effecting such determination, the substance to be determined, or analyte, which contains the ion of interest is contacted with a fluorescent indicator as disclosed above. Complexation of the metal ion in the chelator of the indicator results in a detectable change in the fluorescence properties of the indicator. Detection and optionally quantification of the detectable change permits the ion of interest to be detected and optionally quantified.

Upon binding the target ion in the chelating moiety of the indicator, the optical properties of the attached fluorophore are generally affected in a detectable way, and this change may be correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluorescence microplate readers, or any other application that currently utilize fluorescent metal ion indicators.

This determination method may be based on the so-called "PET effect", or the transfer, induced by photons, of electrons (photoinduced electron transfer=PET) from the ionophoric moiety or ionophore, respectively, to the fluorophore moiety or fluorophore, respectively, which leads to a decrease in the (relative) fluorescence intensity and the fluorescence decay time of the fluorophore. Absorption and emission wavelengths, however, are not significantly affected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect may be partly or completely inhibited, so that there is an increase in the fluorescence of the fluorophore moiety. Hence, the concentration or the activity of the ion to be determined can be deduced by measuring the change in fluorescence properties, i.e. fluorescence intensity and/or fluorescence decay time.

A variety of fluorescent indicators that are useful for the detection of biologically relevant soluble free metal ions (such as $Ca^{2+}$, $Mg^{2+}$ and $Zn^{2+}$) have been described that utilize oxygen-containing anionic or polyanionic chelators to bind to metal ions. In general, a useful property for metal ion indicators is selectivity, or the ability to detect and/or quantify a selected metal ion in the presence of other metal ions. Discrimination of $Ca^{2+}$, $Na^+$ and $K^+$ ions in the presence of other metal ions is particularly advantageous in certain biological or environmental samples. For most biological applications, it is useful that the indicators be effective in aqueous solutions. It is also beneficial if the indicator absorbs and emits light in the visible spectrum where biological materials typically have low intrinsic absorbance or fluorescence.

Optical methods using fluorescence detection of metal ions permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information (Eidelman, O. Cabantchik, Z. I. Biochim. Biophys. Acta, 1989, 988, 319-334). The general principle of monitoring transport by fluorescence is based on having compartment-dependent variations in fluorescence properties associated with translocation of compounds.

Optical methods were developed initially for measuring $Ca^{2+}$ ion flux (U.S. Pat. No. 5,049,673; Scarpa, A. Methods of Enzymology, 1979, 56, 301 Academic Press, Orlando, Fla.; Tsien, R. Y. Biochemistry, 1980, 19, 2396; Grynkiewicz, G., Poenic, M., Tsien, R. Y. J. Biol Chem., 260, 3440) and have been modified for high-throughput assays (U.S. Pat. No. 6,057,114). The flux of $Ca^{2+}$ ion is typically performed using calcium-sensitive fluorescent dyes such as Fluo-3, Fluo-4, Fluo-8, Cal-520, Calcium Green, and others.

In particular, fluorescent indicators utilizing a BAPTA chelator have been previously described. A determination method utilizing aza-cryptands as the chelator moiety and using xanthenes and coumarins as fluorophores has also been described (U.S. Pat. No. 5,439,828 and US Patent Application 20020164616). These aza-cryptand may, depending on their structure, exhibit selectivity for lithium, sodium or potassium ions. Some fluorescent indicators selective for $Li^+$, $Na^+$ and $K^+$ in aqueous or organic solution have also been described, based on the chemical modification of crown ethers (U.S. Pat. No. 5,134,232; U.S. Pat. No. 5,405,975).

A variety of carbofluorescein metal ion indicators can be prepared as discussed above. A person skilled in the art can readily prepare carbofluorescein indicators using the methods discussed above. Selected embodiments of the invention are given in Table 4 for illustration purpose:

TABLE 1

Example compounds of the invention:

| Indicator | Structure | Use |
|---|---|---|
| 8 | 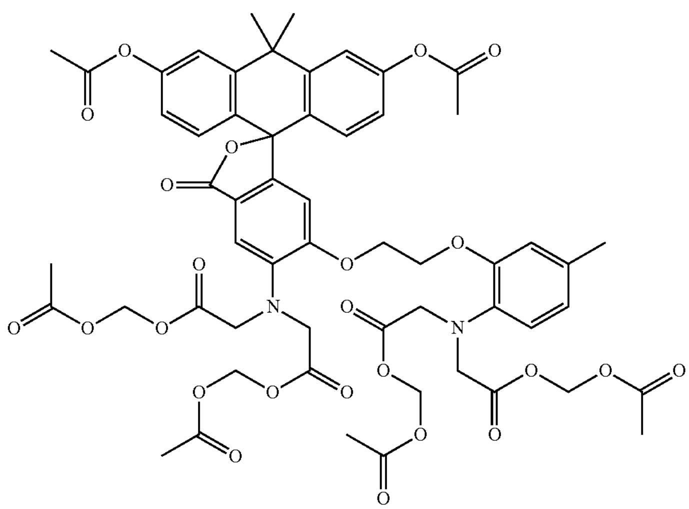 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2ccc(OC(C)=O)cc2C(C)(C)c2cc(OC(C)=O)ccc21] | Detecting $Ca^{2+}$ |
| 9 | 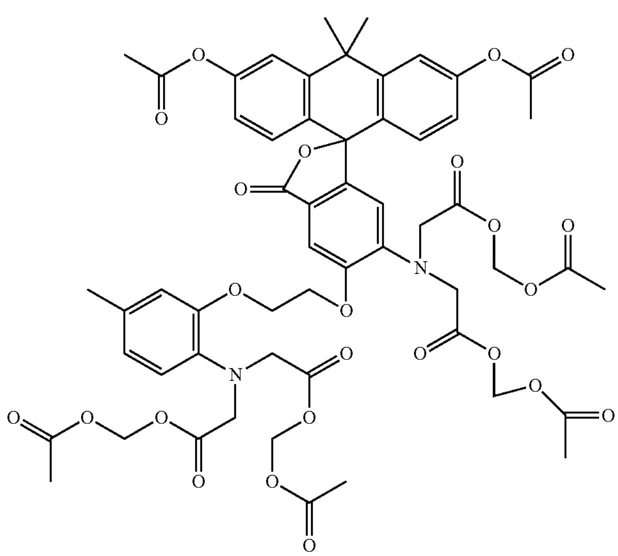 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C1(OC2=O)c2ccc(OC(C)=O)cc2C(C)(C)c2cc(OC(C)=O)ccc21] | Detecting $Ca^{2+}$ |

TABLE 1-continued

Example compounds of the invention:

| Indicator | Structure | Use |
|---|---|---|
| 16 | 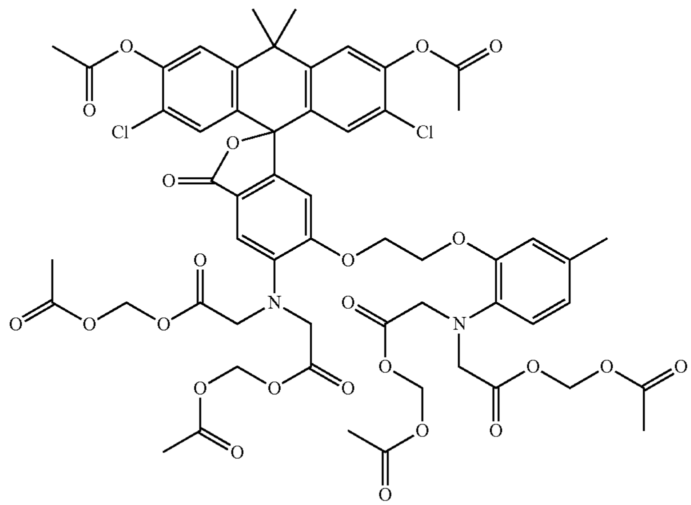 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(Cl)c(OC(C)=O)cc2C(C)(C)c2cc(OC(C)=O)c(Cl)cc21] | Detecting $Ca^{2+}$ |
| 85 | 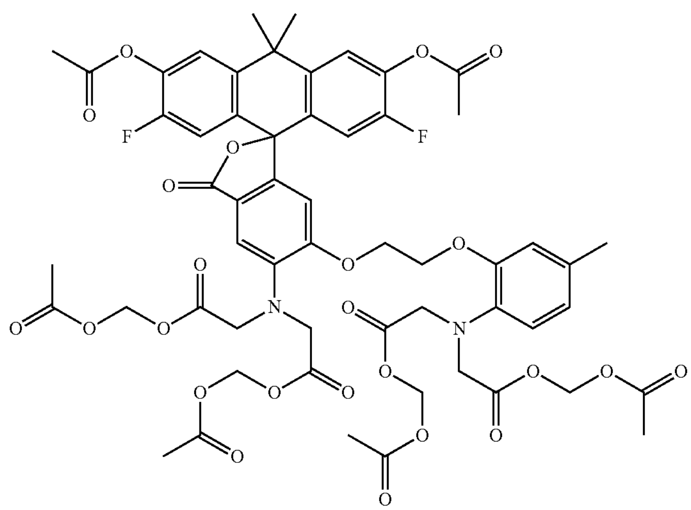 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(F)c(OC(C)=O)cc2C(C)(C)c2cc(OC(C)=O)c(F)cc21] | Detecting $Ca^{2+}$ |
| 93 | 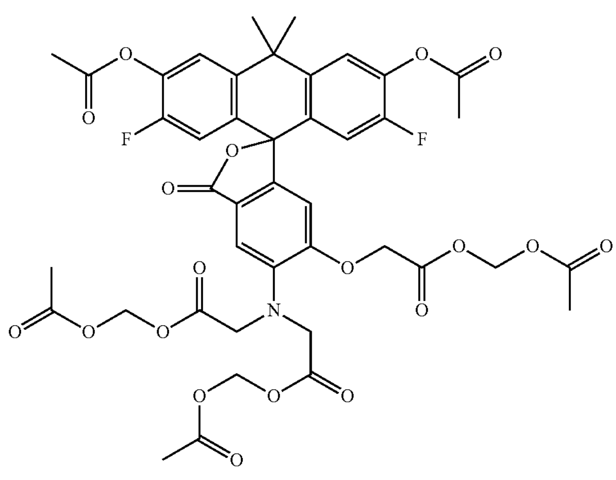 [SMILES: CC(=O)OCOC(=O)COc1cc2c(cc1N(CC(=O)OCOC(C)=O)CC(=O)OCOC(C)=O)C(=O)OC21c2cc(F)c(OC(C)=O)cc2C(C)(C)c2cc(OC(C)=O)c(F)cc21] | Detecting $Zn^{2+}$ and $Mg^{2+}$ |

TABLE 1-continued

Example compounds of the invention:

| Indicator | Structure | Use |
|---|---|---|
| 125 | 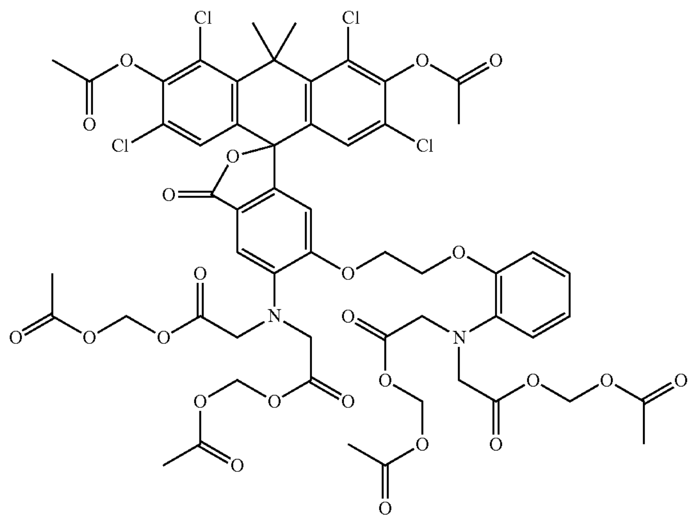 [SMILES: CC(=O)OCOC(=O)CN(CC(=O)OCOC(C)=O)c1ccccc1OCCOc1cc2c(cc1N(CC(=O)OCOC(C)=O)CC(=O)OCOC(C)=O)C(=O)OC21c2cc(Cl)c(OC(C)=O)c(Cl)c2C(C)(C)c2c1cc(Cl)c(OC(C)=O)c2Cl] | Detecting $Ca^{2+}$ |
| 128 | 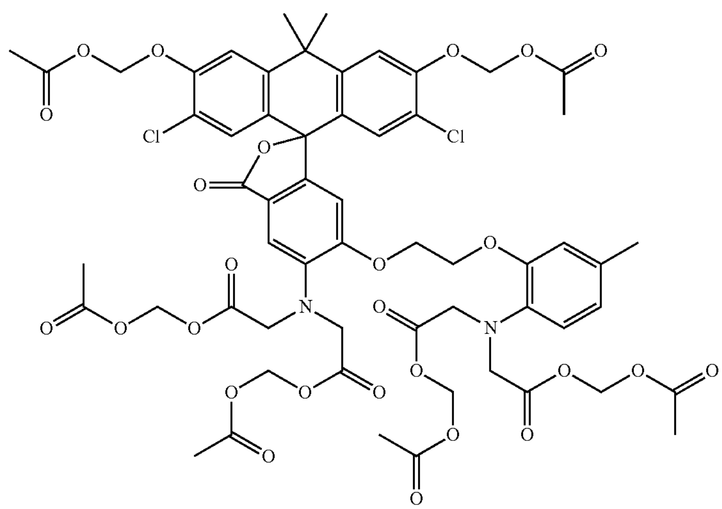 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(Cl)c(OCOC(C)=O)cc2C(C)(C)c2cc(OCOC(C)=O)c(Cl)cc21] | Detecting $Ca^{2+}$ |
| 139 | 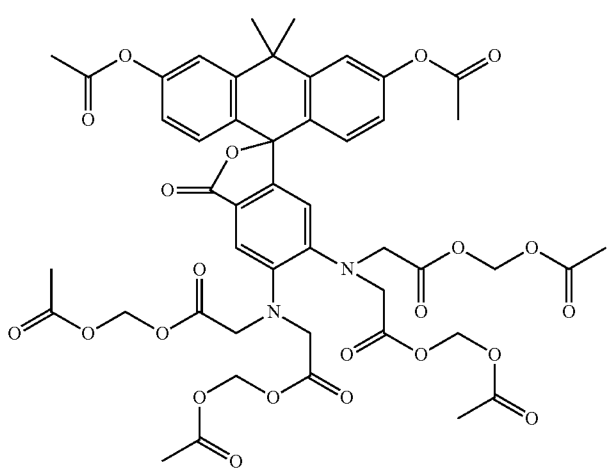 [SMILES: CC(=O)OCOC(=O)CN(CC(=O)OCOC(C)=O)c1cc2c(cc1N(CC(=O)OCOC(C)=O)CC(=O)OCOC(C)=O)C1(OC2=O)c2ccc(OC(C)=O)cc2C(C)(C)c2cc(OC(C)=O)ccc21] | Detecting transitional metal ions |

TABLE 1-continued

Example compounds of the invention:

| Indicator | Structure | Use |
|---|---|---|
| 145 | 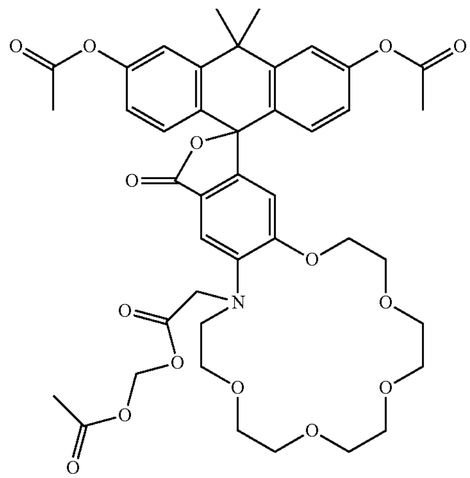 [SMILES: CC(=O)OCOC(=O)CN1CCOCCOCCOCCOCCOc2cc3c(cc21)C(=O)OC31c2ccc(OC(C)=O)cc2C(C)(C)c2cc(OC(C)=O)ccc21] | Detecting Na$^+$ |
| 150 | 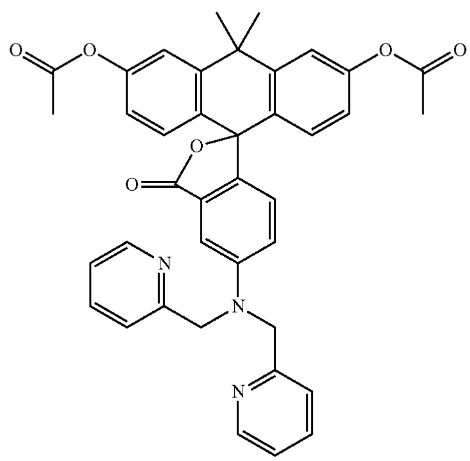 [SMILES: CC(=O)Oc1ccc2c(c1)C(C)(C)c1cc(OC(C)=O)ccc1C21OC(=O)c2cc(N(Cc3ccccn3)Cc3ccccn3)ccc21] | Detecting Ni$^{2+}$ |
| 200 | 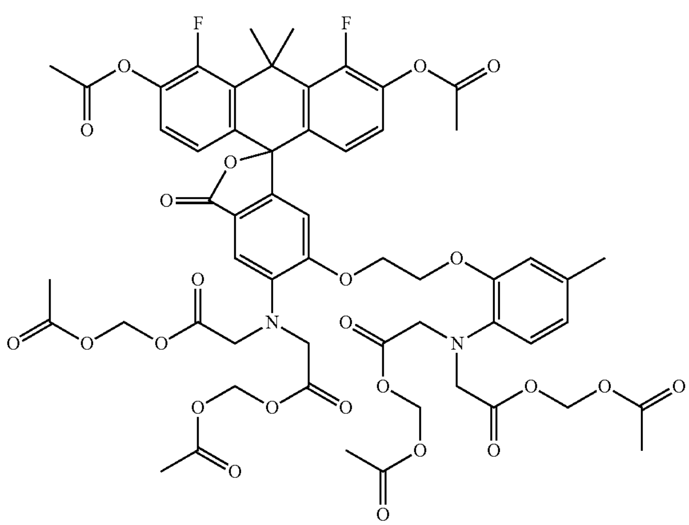 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2ccc(OC(C)=O)c(F)c2C(C)(C)c2c1ccc(OC(C)=O)c2F] | Detecting Ca$^{2+}$ |

TABLE 1-continued

Example compounds of the invention:

| Indicator | Structure | Use |
|---|---|---|
| 201 | (structure) | Detecting $Ca^{2+}$ |
| 202 | (structure) | Detecting $Ca^{2+}$ |
| 203 | (structure) | Detecting $Ca^{2+}$ |

TABLE 1-continued
| Indicator | Structure | Use |
|---|---|---|
| 204 | 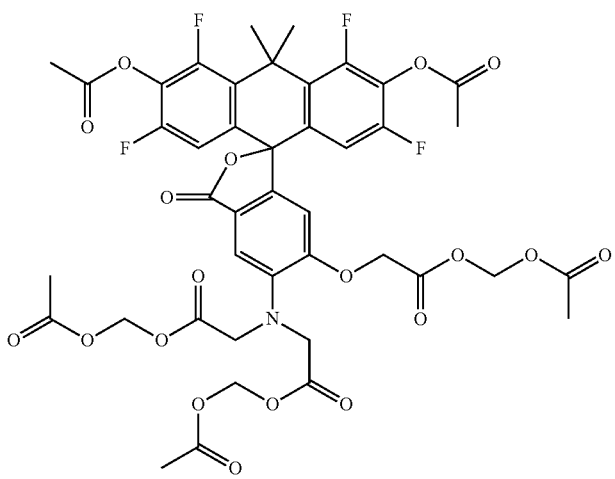 | Detecting $Zn^{2+}$ and $Mg^{2+}$ |
| 205 | 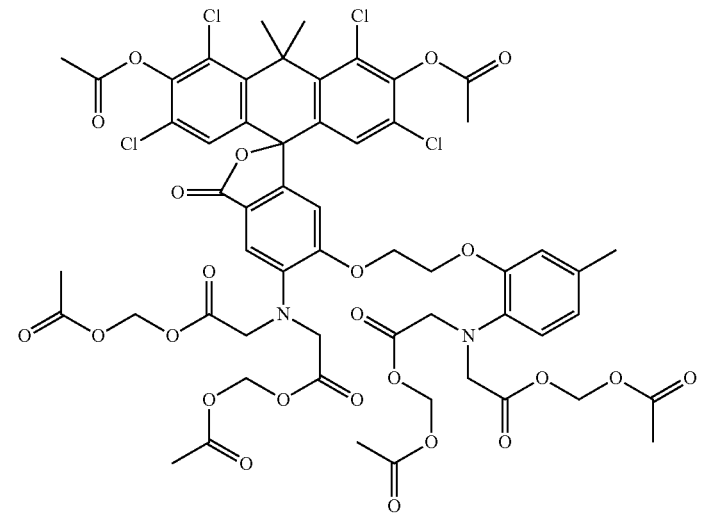 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(Cl)c(OC(C)=O)c(F)c2C(C)(C)c2c1cc(Cl)c(OC(C)=O)c2F] | Detecting $Ca^{2+}$ |
| 206 | 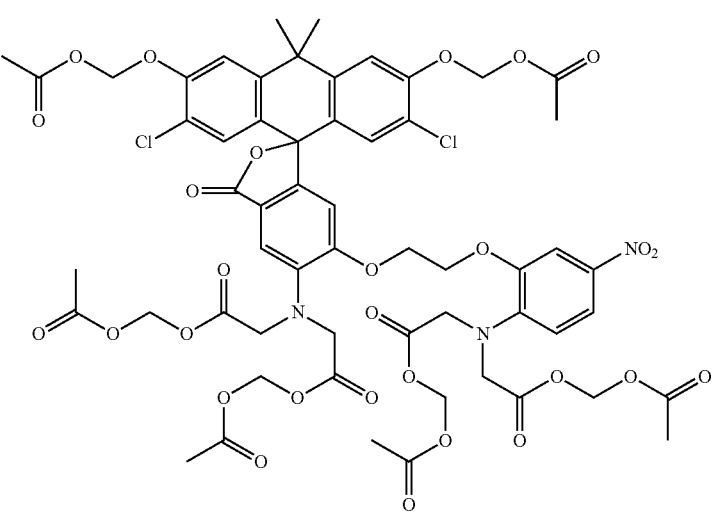 [SMILES: CC(=O)OCOC(=O)CN(CC(=O)OCOC(C)=O)c1ccc([N+](=O)[O-])cc1OCCOc1cc2c(cc1N(CC(=O)OCOC(C)=O)CC(=O)OCOC(C)=O)C(=O)OC21c2cc(Cl)c(OCOC(C)=O)cc2C(C)(C)c2cc(OCOC(C)=O)c(Cl)cc21] | Detecting $Ca^{2+}$ |

TABLE 1-continued
| Indicator | Structure | Use |
|---|---|---|
| 207 | 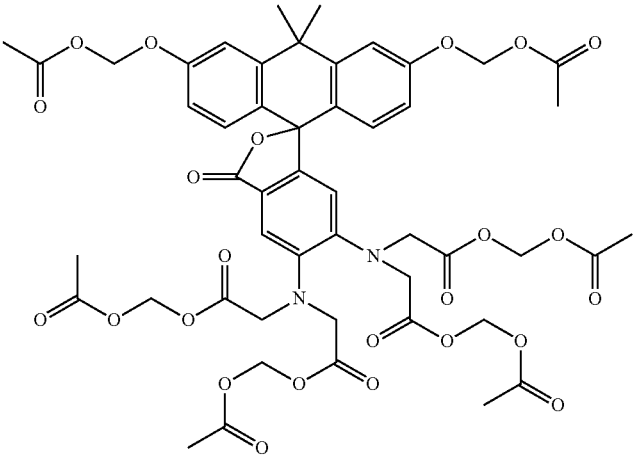 [SMILES: CC(=O)OCOC(=O)CN(CC(=O)OCOC(C)=O)c1cc2c(cc1N(CC(=O)OCOC(C)=O)CC(=O)OCOC(C)=O)C1(OC2=O)c2ccc(OCOC(C)=O)cc2C(C)(C)c2cc(OCOC(C)=O)ccc21] | Detecting transitional metal ions |
| 208 | 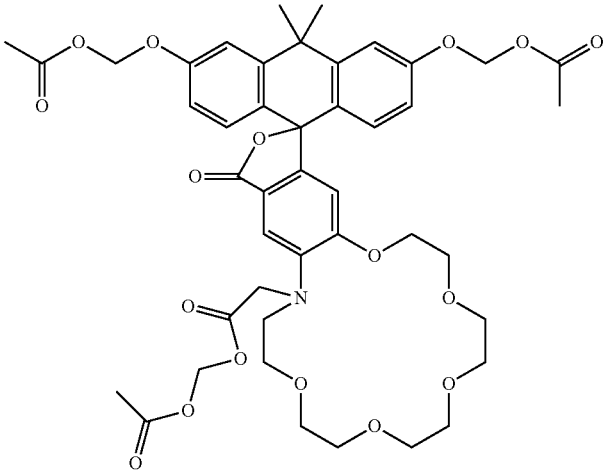 [SMILES: CC(=O)OCOC(=O)CN1CCOCCOCCOCCOCCOc2cc3c(cc21)C(=O)OC31c2ccc(OCOC(C)=O)cc2C(C)(C)c2cc(OCOC(C)=O)ccc21] | Detecting Na$^+$ |
| 209 | 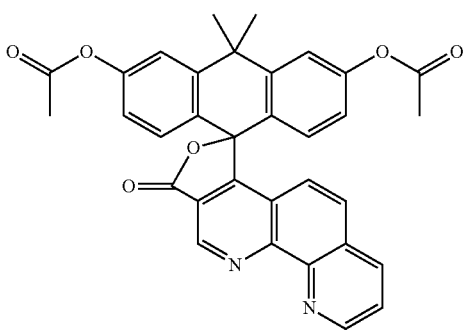 [SMILES: CC(=O)Oc1ccc2c(c1)C(C)(C)c1cc(OC(C)=O)ccc1C21OC(=O)c2cnc3c(ccc4cccnc43)c21] | Detecting transitional metal ions |

TABLE 1-continued
Example compounds of the invention:
| Indicator | Structure | Use |
|---|---|---|
| 210 | 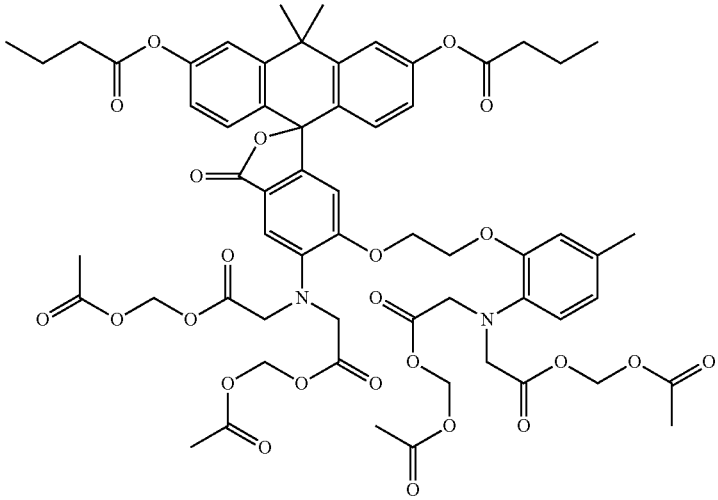 [SMILES: CCCC(=O)Oc1ccc2c(c1)C(C)(C)c1cc(OC(=O)CCC)ccc1C21OC(=O)c2cc(N(CC(=O)OCOC(C)=O)CC(=O)OCOC(C)=O)c(OCCOc3cc(C)ccc3N(CC(=O)OCOC(C)=O)CC(=O)OCOC(C)=O)cc21] | Detecting $Ca^{2+}$ |
| 211 | 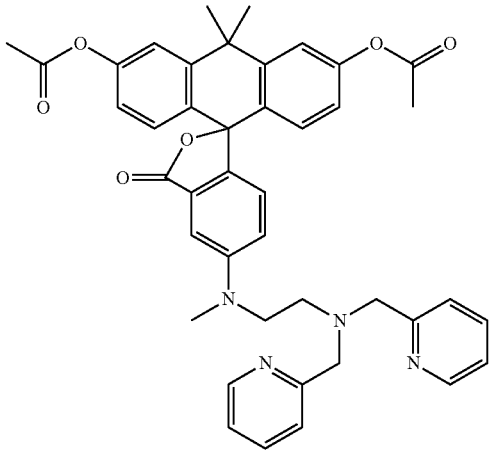 [SMILES: CC(=O)Oc1ccc2c(c1)C(C)(C)c1cc(OC(C)=O)ccc1C21OC(=O)c2cc(N(C)CCN(Cc3ccccn3)Cc3ccccn3)ccc21] | Detecting $Zn^{2+}$ |
| 212 | 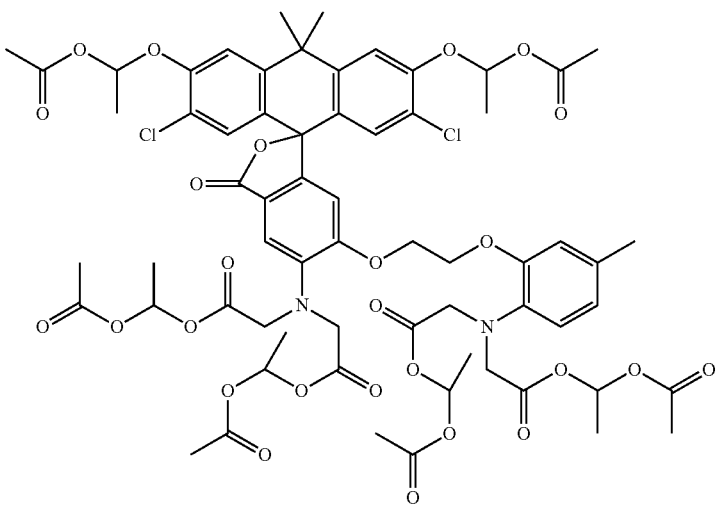 [SMILES: CC(=O)OC(C)OC(=O)CN(CC(=O)OC(C)OC(C)=O)c1ccc(C)cc1OCCOc1cc2c(cc1N(CC(=O)OC(C)OC(C)=O)CC(=O)OC(C)OC(C)=O)C(=O)OC21c2cc(Cl)c(OC(C)OC(C)=O)cc2C(C)(C)c2cc(OC(C)OC(C)=O)c(Cl)cc21] | Detecting $Ca^{2+}$ |

TABLE 1-continued
Example compounds of the invention:
| Indicator | Structure | Use |
|---|---|---|
| 213 | 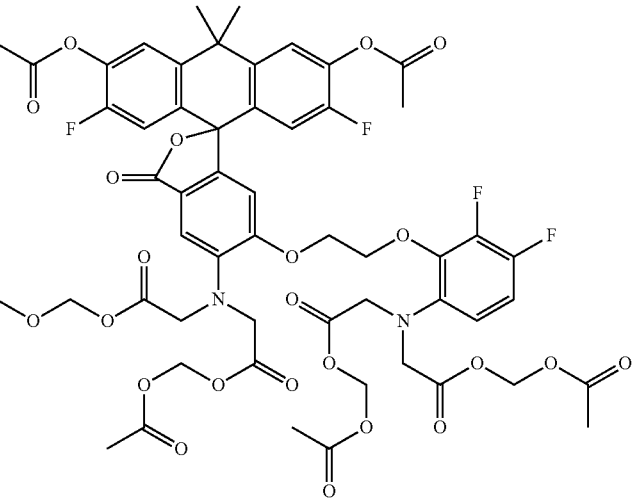 | Detecting $Ca^{2+}$ |
| 214 | 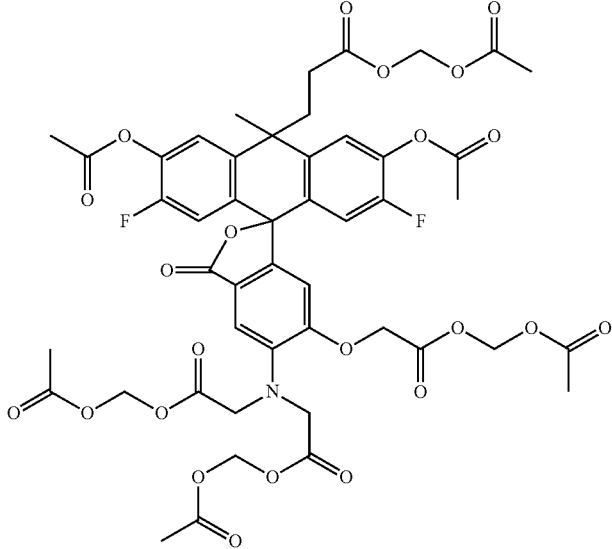 [SMILES: CC(=O)OCOC(=O)CCC1(C)c2cc(OC(C)=O)c(F)cc2C2(OC(=O)c3cc(N(CC(=O)OCOC(C)=O)CC(=O)OCOC(C)=O)c(OCC(=O)OCOC(C)=O)cc32)c2cc(F)c(OC(C)=O)cc21] | Detecting $Mg^{2+}$ |
| 215 | 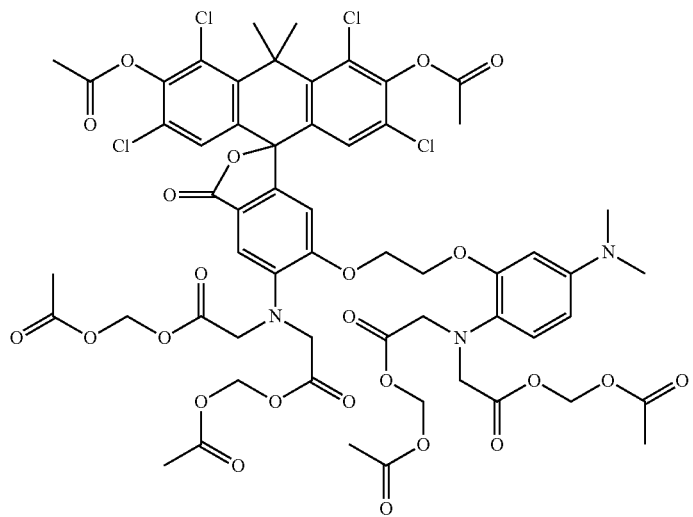 [SMILES: CC(=O)OCOC(=O)CN(CC(=O)OCOC(C)=O)c1ccc(N(C)C)cc1OCCOc1cc2c(cc1N(CC(=O)OCOC(C)=O)CC(=O)OCOC(C)=O)C(=O)OC21c2cc(Cl)c(OC(C)=O)c(Cl)c2C(C)(C)c2c1cc(Cl)c(OC(C)=O)c2Cl] | Detecting $Ca^{2+}$ |

TABLE 1-continued
Example compounds of the invention:
| Indicator | Structure | Use |
|---|---|---|
| 216 | 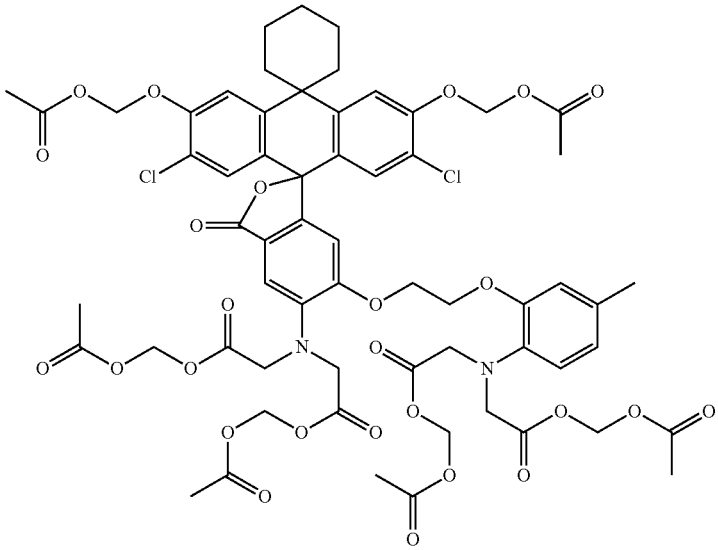 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(Cl)c(OCOC(C)=O)cc2C2(CCCCC2)c2cc(OCOC(C)=O)c(Cl)cc21] | Detecting Ca$^{2+}$ |
| 217 | 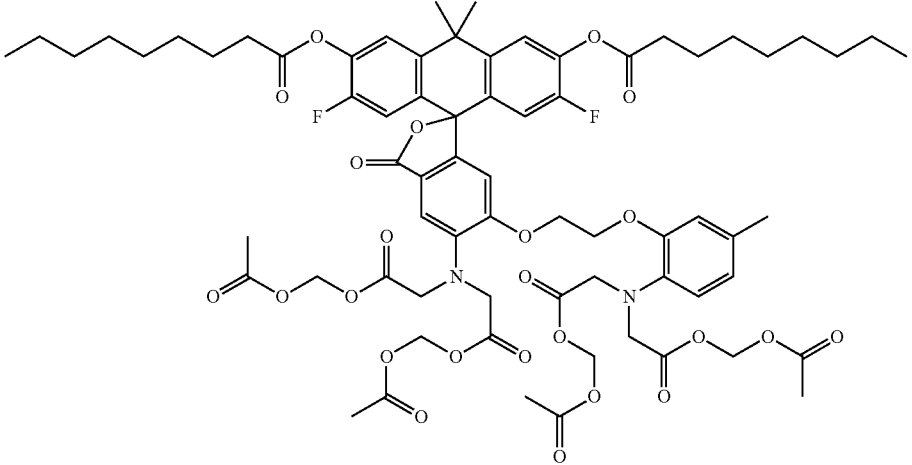 [SMILES: CCCCCCCCC(=O)Oc1cc2c(cc1F)C1(OC(=O)c3cc(N(CC(=O)OCOC(C)=O)CC(=O)OCOC(C)=O)c(OCCOc4cc(C)ccc4N(CC(=O)OCOC(C)=O)CC(=O)OCOC(C)=O)cc31)c1cc(F)c(OC(=O)CCCCCCCC)cc1C2(C)C] | Detecting Ca$^{2+}$ |
| 218 | 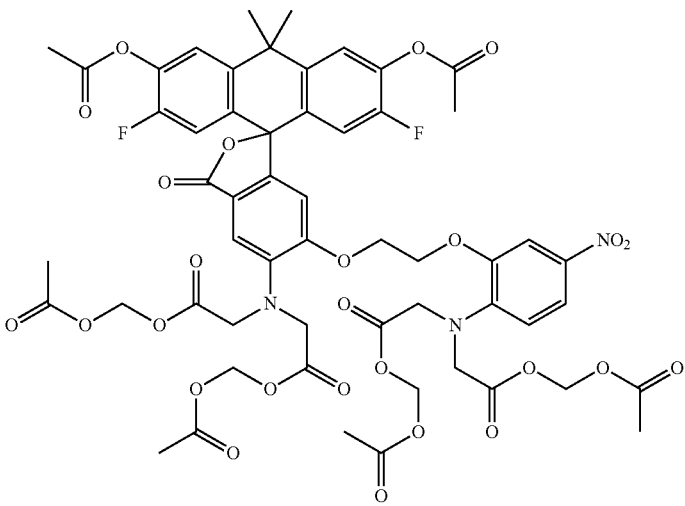 [SMILES: CC(=O)OCOC(=O)CN(CC(=O)OCOC(C)=O)c1ccc([N+](=O)[O-])cc1OCCOc1cc2c(cc1N(CC(=O)OCOC(C)=O)CC(=O)OCOC(C)=O)C(=O)OC21c2cc(F)c(OC(C)=O)cc2C(C)(C)c2cc(OC(C)=O)c(F)cc21] | Detecting Ca$^{2+}$ |

TABLE 1-continued

Example compounds of the invention:

| Indicator | Structure | Use |
|---|---|---|
| 219 | 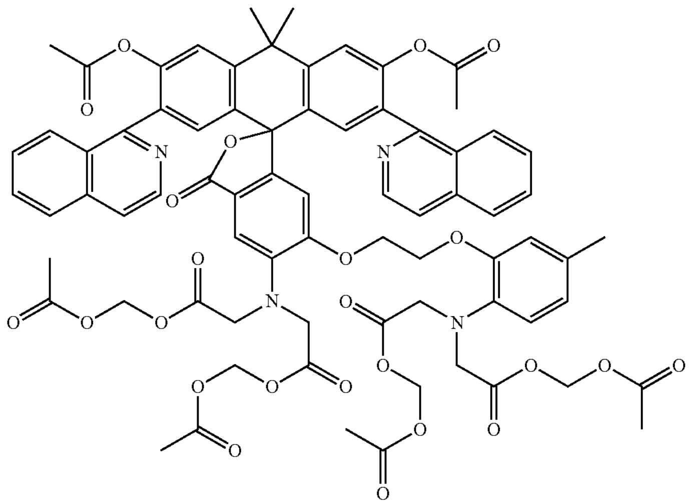 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(-c3nccc4ccccc34)c(OC(C)=O)cc2C(C)(C)c2cc(OC(C)=O)c(-c3nccc4ccccc34)cc21] | Detecting $Ca^{2+}$ |
| 220 | 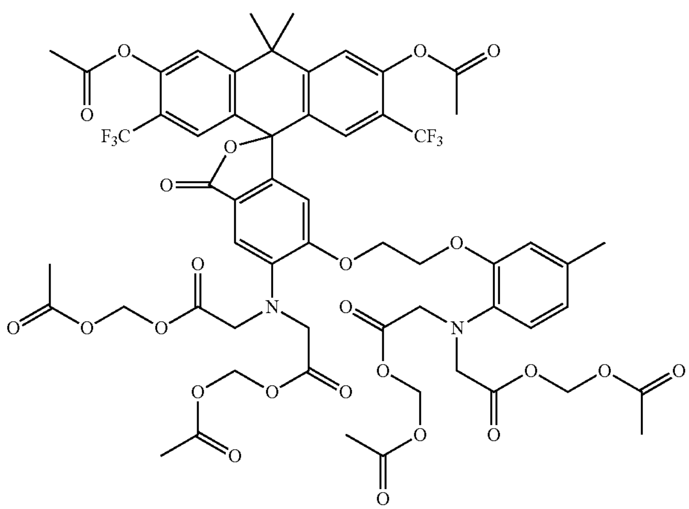 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(C(F)(F)F)c(OC(C)=O)cc2C(C)(C)c2cc(OC(C)=O)c(C(F)(F)F)cc21] | Detecting $Ca^{2+}$ |
| 221 | 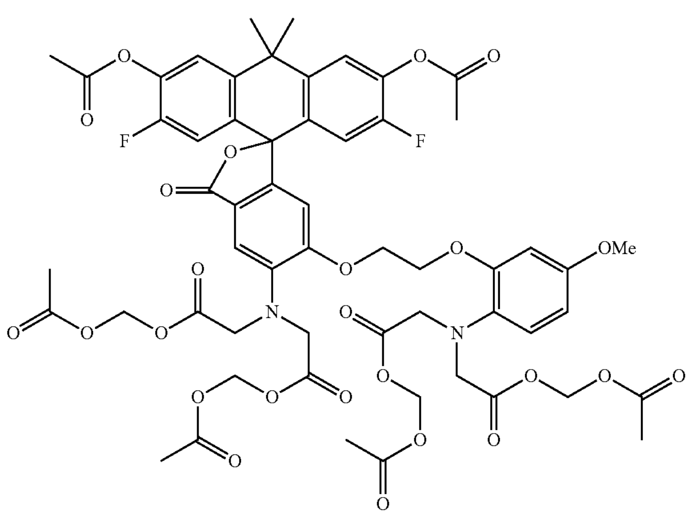 | Detecting $Ca^{2+}$ |

TABLE 1-continued

Example compounds of the invention:

| Indicator | Structure | Use |
|---|---|---|
| 222 | 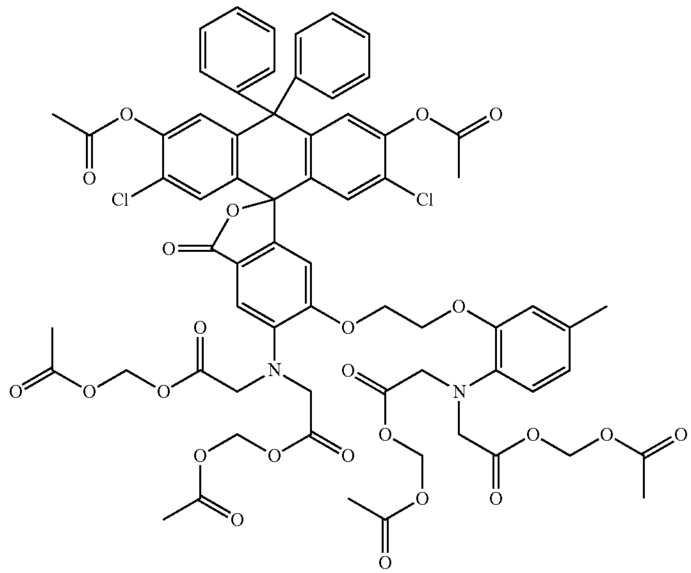 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(Cl)c(OC(C)=O)cc2C(c2ccccc2)(c2ccccc2)c2cc(OC(C)=O)c(Cl)cc21] | Detecting $Ca^{2+}$ |
| 223 | 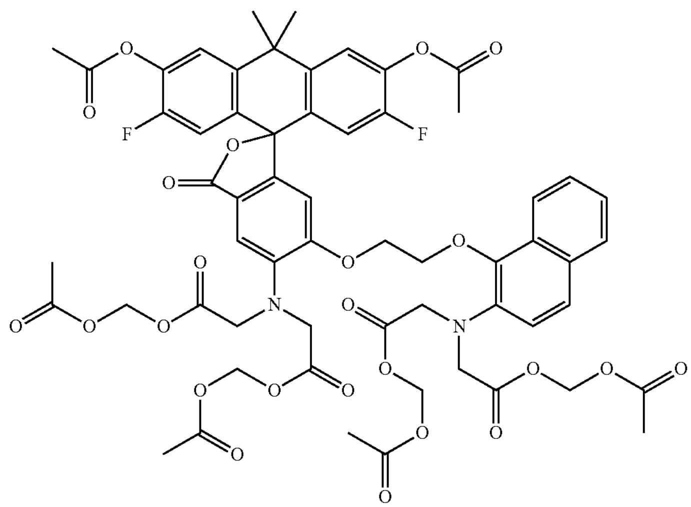 [SMILES: CC(=O)OCOC(=O)CN(CC(=O)OCOC(C)=O)c1cc2c(cc1OCCOc1c(N(CC(=O)OCOC(C)=O)CC(=O)OCOC(C)=O)ccc3ccccc13)C1(OC2=O)c2cc(F)c(OC(C)=O)cc2C(C)(C)c2cc(OC(C)=O)c(F)cc21] | Detecting $Ca^{2+}$ |
| 224 | 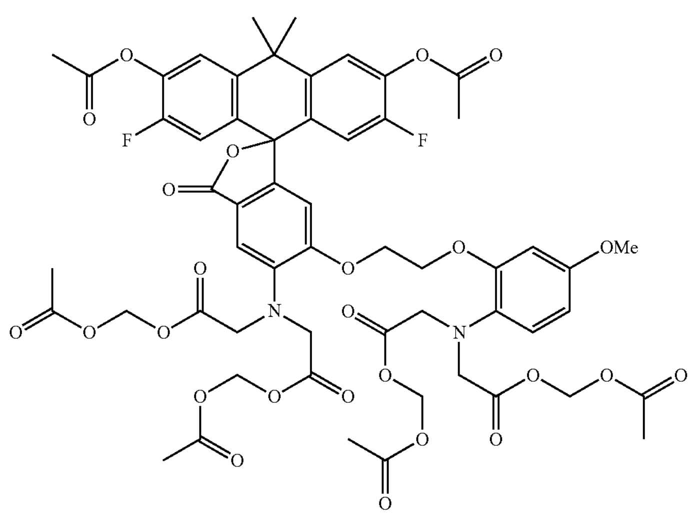 | Detecting $Ca^{2+}$ |

TABLE 1-continued

Example compounds of the invention:

| Indicator | Structure | Use |
|-----------|-----------|-----|
| 225 | 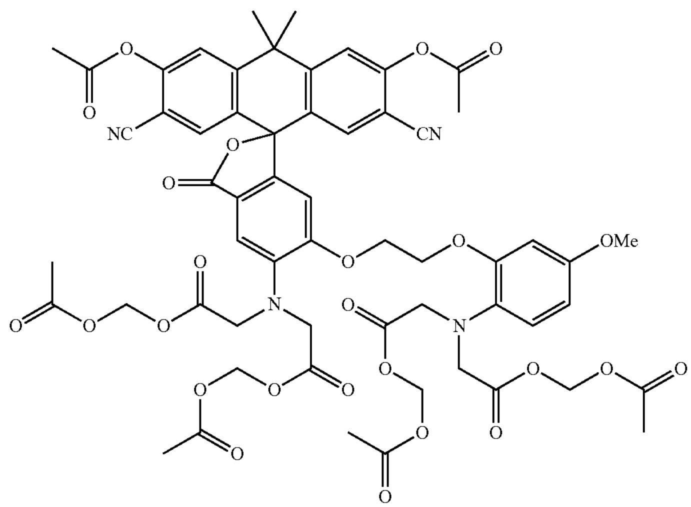 [SMILES: COc1ccc(N(CC(=O)OCOC(C)=O)CC(=O)OCOC(C)=O)c(OCCOc2cc3c(cc2N(CC(=O)OCOC(C)=O)CC(=O)OCOC(C)=O)C(=O)OC32c3cc(C#N)c(OC(C)=O)cc3C(C)(C)c3cc(OC(C)=O)c(C#N)cc32)c1] | Detecting $Ca^{2+}$ |
| 226 | 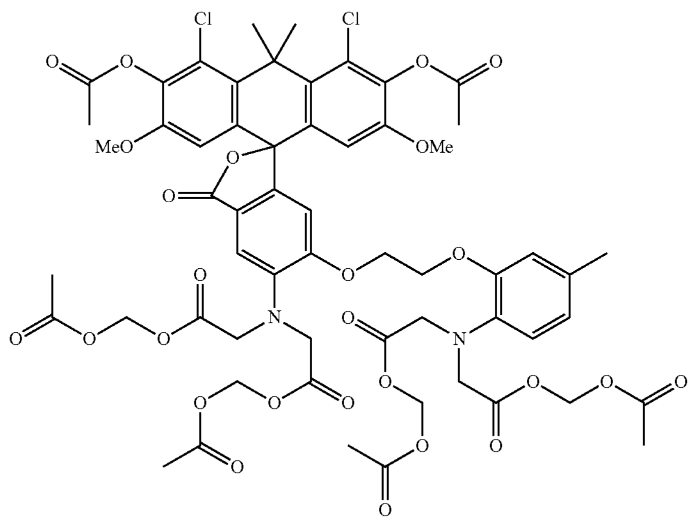 [SMILES: COc1cc2c(c(Cl)c1OC(C)=O)C(C)(C)c1c(cc(OC)c(OC(C)=O)c1Cl)C21OC(=O)c2cc(N(CC(=O)OCOC(C)=O)CC(=O)OCOC(C)=O)c(OCCOc3cc(C)ccc3N(CC(=O)OCOC(C)=O)CC(=O)OCOC(C)=O)cc21] | Detecting $Ca^{2+}$ |
| 227 | 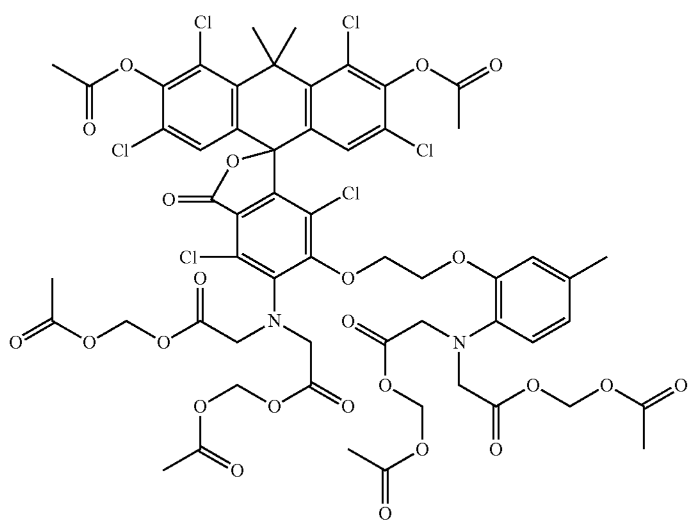 [SMILES: CC(=O)OCOC(=O)CN(CC(=O)OCOC(C)=O)c1ccc(C)cc1OCCOc1c(Cl)c2c(c(Cl)c1N(CC(=O)OCOC(C)=O)CC(=O)OCOC(C)=O)C(=O)OC21c2cc(Cl)c(OC(C)=O)c(Cl)c2C(C)(C)c2c1cc(Cl)c(OC(C)=O)c2Cl] | Detecting $Ca^{2+}$ |

TABLE 1-continued

Example compounds of the invention:

| Indicator | Structure | Use |
|---|---|---|
| 228 | 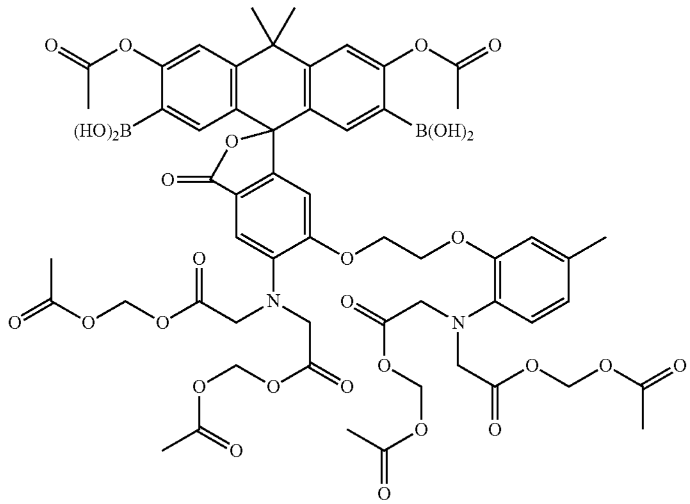 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(B(O)O)c(OC(C)=O)cc2C(C)(C)c2cc(OC(C)=O)c(B(O)O)cc21] | Detecting Ca$^{2+}$ |
| 229 | 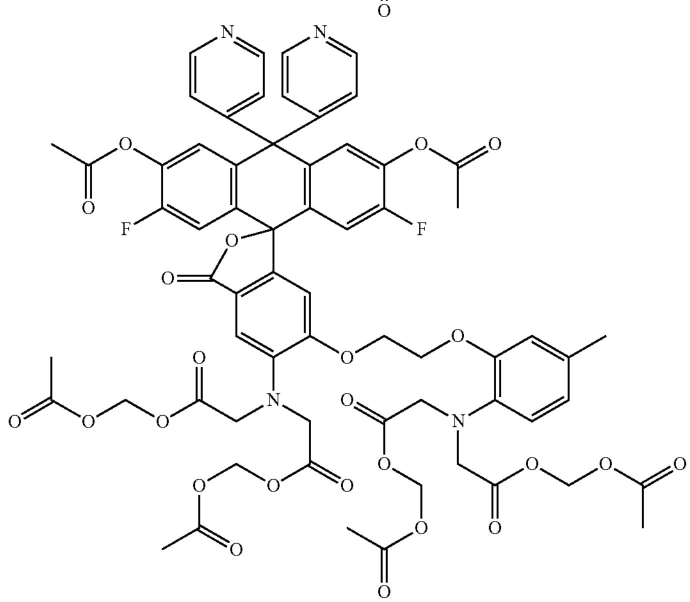 | Detecting Ca$^{2+}$ |
| 230 | 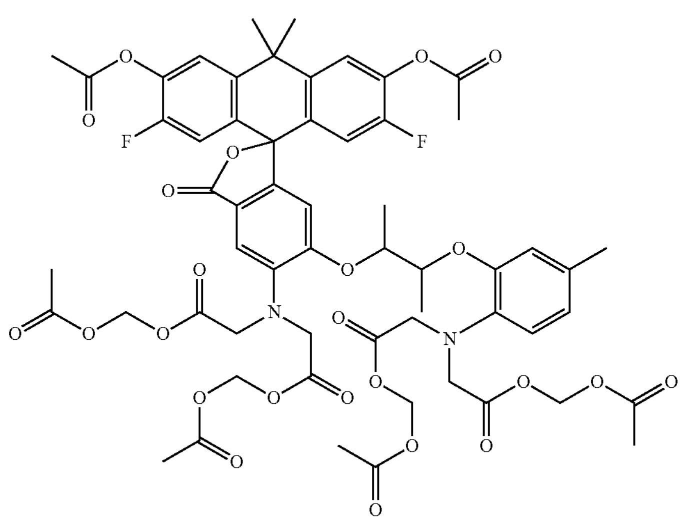 [SMILES: CC(=O)OCOC(=O)CN(CC(=O)OCOC(C)=O)c1ccc(C)cc1OC(C)C(C)Oc1cc2c(cc1N(CC(=O)OCOC(C)=O)CC(=O)OCOC(C)=O)C(=O)OC21c2cc(F)c(OC(C)=O)cc2C(C)(C)c2cc(OC(C)=O)c(F)cc21] | Detecting Ca$^{2+}$ |

TABLE 1-continued

Example compounds of the invention:

| Indicator | Structure | Use |
|---|---|---|
| 231 | 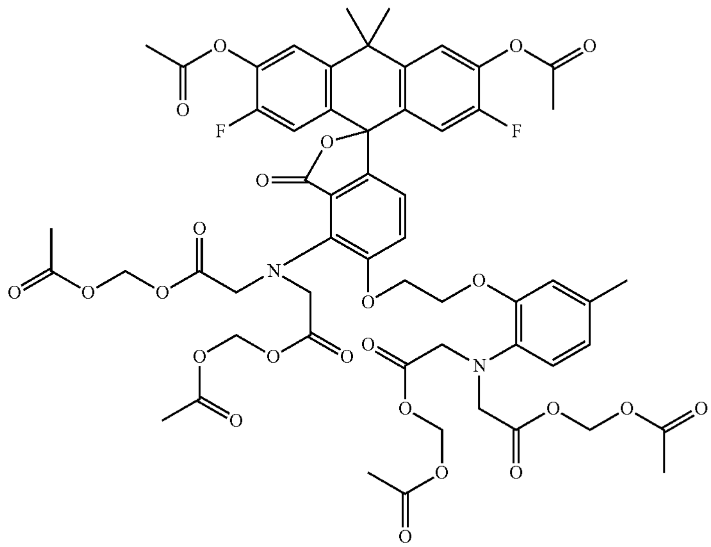 [SMILES: CC(=O)OCOC(=O)CN(CC(=O)OCOC(C)=O)c1ccc(C)cc1OCCOc1ccc2c(c1N(CC(=O)OCOC(C)=O)CC(=O)OCOC(C)=O)C(=O)OC21c2cc(F)c(OC(C)=O)cc2C(C)(C)c2cc(OC(C)=O)c(F)cc21] | Detecting $Ca^{2+}$ |
| 232 | 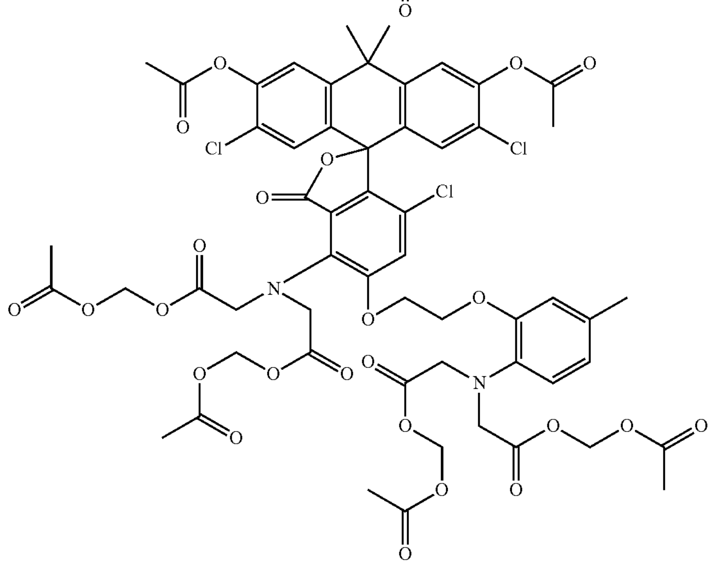 | Detecting $Ca^{2+}$ |
| 233 | 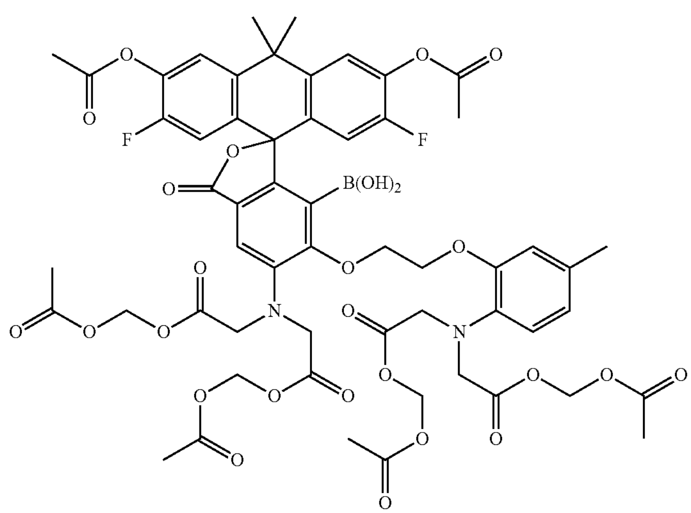 [SMILES: CC(=O)OCOC(=O)CN(CC(=O)OCOC(C)=O)c1ccc(C)cc1OCCOc1c(N(CC(=O)OCOC(C)=O)CC(=O)OCOC(C)=O)cc2c(c1B(O)O)C1(OC2=O)c2cc(F)c(OC(C)=O)cc2C(C)(C)c2cc(OC(C)=O)c(F)cc21] | Detecting $Ca^{2+}$ |

TABLE 1-continued
| Indicator | Structure | Use |
|---|---|---|
| 234 | 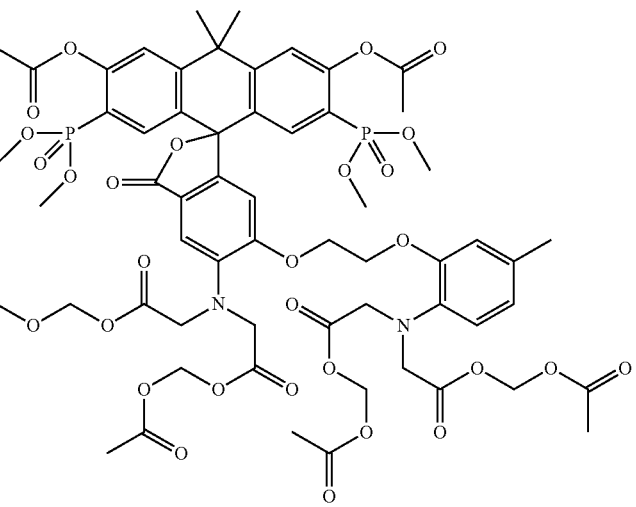 | Detecting $Ca^{2+}$ |
| 235 | 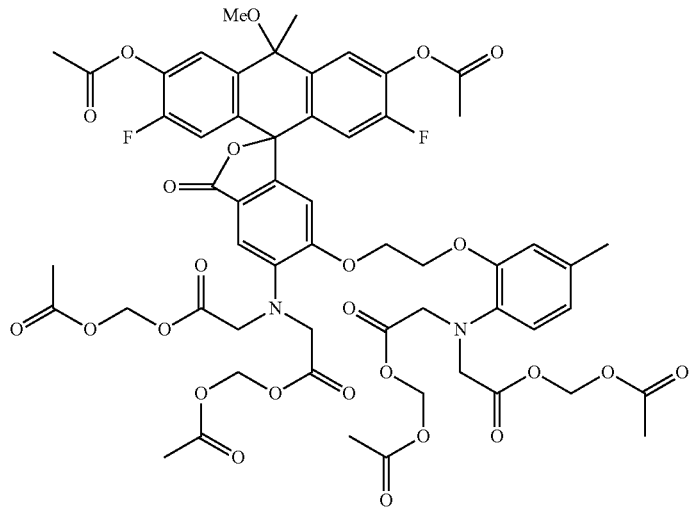 [SMILES: COC1(C)c2cc(OC(C)=O)c(F)cc2C2(OC(=O)c3cc(N(CC(=O)OCOC(C)=O)CC(=O)OCOC(C)=O)c(OCCOc4cc(C)ccc4N(CC(=O)OCOC(C)=O)CC(=O)OCOC(C)=O)cc32)c2cc(F)c(OC(C)=O)cc21] | Detecting $Ca^{2+}$ |
| 236 | 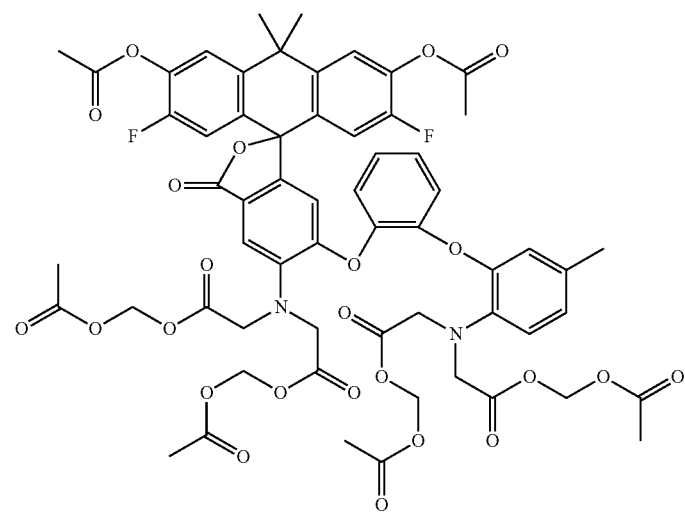 [SMILES: CC(=O)OCOC(=O)CN(CC(=O)OCOC(C)=O)c1ccc(C)cc1Oc1ccccc1Oc1cc2c(cc1N(CC(=O)OCOC(C)=O)CC(=O)OCOC(C)=O)C(=O)OC21c2cc(F)c(OC(C)=O)cc2C(C)(C)c2cc(OC(C)=O)c(F)cc21] | Detecting $Ca^{2+}$ |

TABLE 1-continued
Example compounds of the invention:
| Indicator | Structure | Use |
|---|---|---|
| 237 | 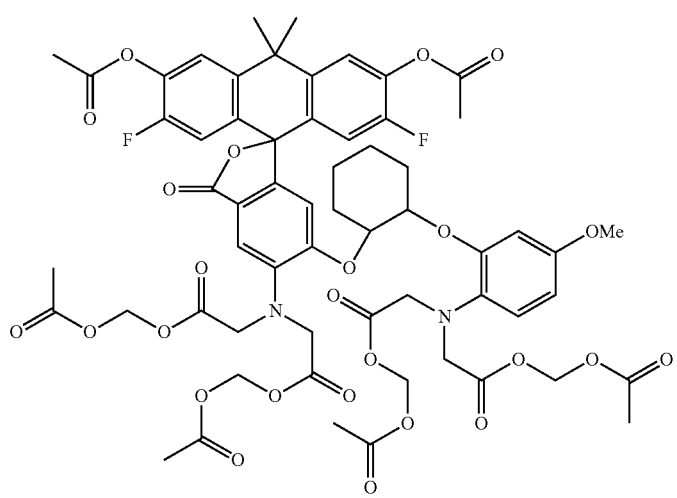 [SMILES: COc1ccc(N(CC(=O)OCOC(C)=O)CC(=O)OCOC(C)=O)c(OC2CCCCC2Oc2cc3c(cc2N(CC(=O)OCOC(C)=O)CC(=O)OCOC(C)=O)C(=O)OC32c3cc(F)c(OC(C)=O)cc3C(C)(C)c3cc(OC(C)=O)c(F)cc32)c1] | Detecting $Ca^{2+}$ |
| 238 | 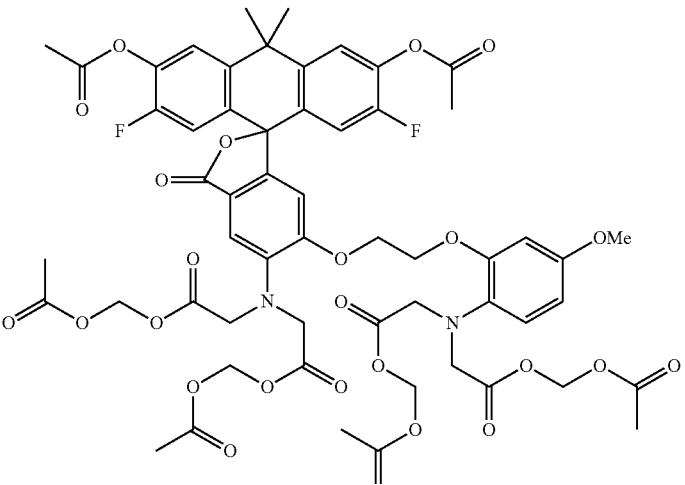 | Detecting $Ca^{2+}$ |
| 239 | 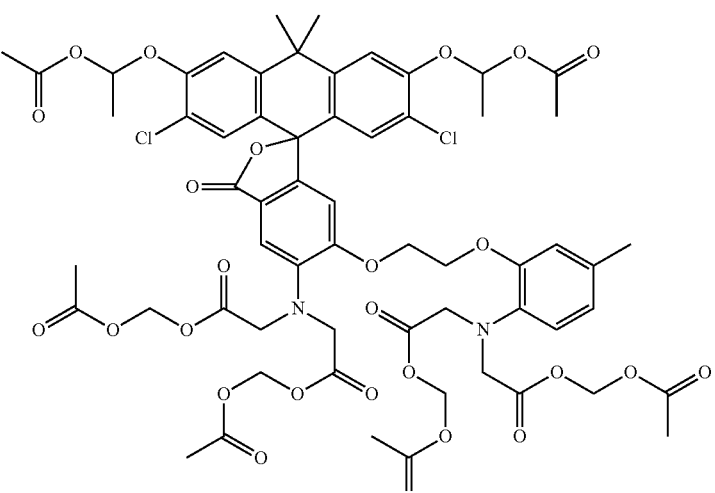 | Detecting $Ca^{2+}$ |

TABLE 1-continued

Example compounds of the invention:

| Indicator | Structure | Use |
|---|---|---|
| 240 | 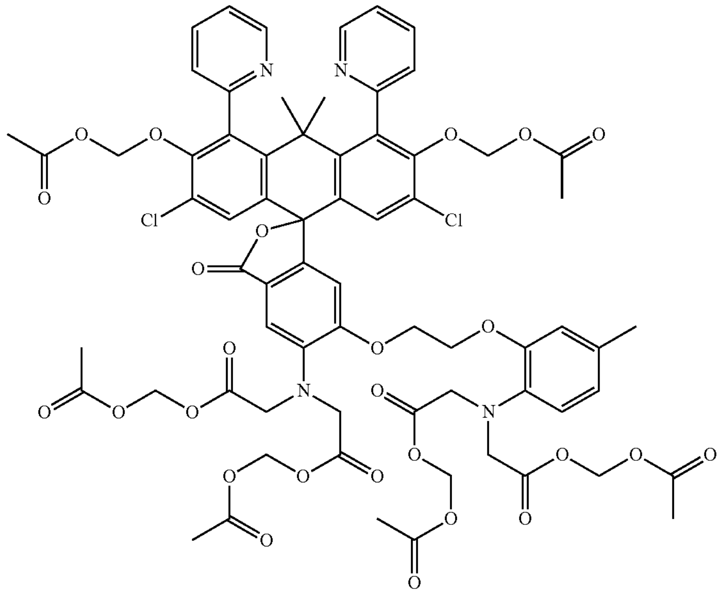 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(Cl)c(OCOC(C)=O)c(-c3ccccn3)c2C(C)(C)c2c1cc(Cl)c(OCOC(C)=O)c2-c1ccccn1] | Detecting Ca$^{2+}$ |
| 241 | 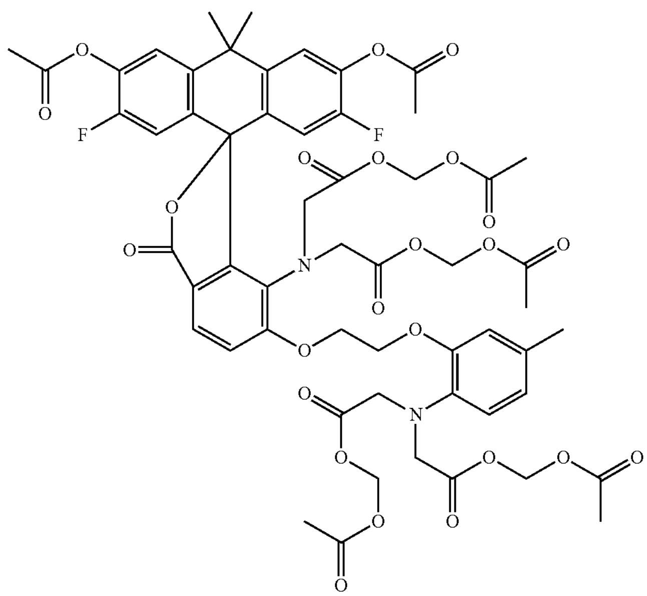 [SMILES: CC(=O)OCOC(=O)CN(CC(=O)OCOC(C)=O)c1ccc(C)cc1OCCOc1ccc2c(c1N(CC(=O)OCOC(C)=O)CC(=O)OCOC(C)=O)C1(OC2=O)c2cc(F)c(OC(C)=O)cc2C(C)(C)c2cc(OC(C)=O)c(F)cc21] | Detecting Ca$^{2+}$ |

The desired indicator compound is generally prepared for use as a detection reagent by dissolving the indicator in solution at a concentration that is optimal for detection of the indicator at the expected concentration of the target ion. Modifications that are designed to enhance permeability of the indicator through the membranes of live cells, such as functionalization of carboxylic acid moieties using acetoxymethyl esters and acetates, may require the indicator to be predissolved in an organic solvent such as dimethylsulfoxide (DMSO) before addition to a cell suspension, where the indicators may then readily enter the cells. Intracellular enzymes then cleave the esters, generating more polar acids and phenols which are then well-retained inside the cells. For applications where permeability of cell-membranes is required, the indicators of the invention are typically substituted by only one fluorophore.

The specific indicator used in a particular assay or experiment may be selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Where the binding of an ion in the metal ion-binding moiety of the indicator results in a detectable change in spectral properties of the indicator compound, that indicator may be used for the detection and/or quantification of that ion (the target ion). Although the change in spectral properties may include for example a change in absorption intensity or wavelength, preferably the change in spectral properties is a detectable fluorescence response. Preferred indicators display a high selectivity, that is, they show a sufficient rejection of non-target ions. The interference of a non-target ion is tested by a comparable titration of the indicator with that ion. In one aspect of the invention, the target ions for the indicators of the present invention are selected from $Ca^{2+}$, $Na^+$ and $K^+$.

A detectable fluorescence response, as used herein, is a change in a fluorescence property of the indicator that is capable of being perceived, either by direct visual observation or instrumentally, the presence or magnitude of which is a function of the presence and/or concentration of a target metal ion in the test sample. This change in a fluorescence property is typically a change in fluorescence quantum yield, fluorescence polarization, fluorescence lifetime, a shift in excitation or emission wavelength, among others, or a combination of one or more of such changes in fluorescence properties. The detectable change in a given spectral property is generally an increase or a decrease. However, spectral changes that result in an enhancement of fluorescence intensity and/or a shift in the wavelength of fluorescence emission or excitation may also be useful. The change in fluorescence on ion binding may be due to conformational or electronic changes in the indicator that may occur in either the excited or ground state of the fluorophore, due to changes in electron density at the ion binding site, due to quenching of fluorescence by the bound target metal ion, or due to any combination of these or other effects.

A typical indicator for a specific target ion is an indicator that exhibits at least a 50-fold change in net fluorescence emission intensity (either an increase or decrease), or at least a 1 nanosecond difference in fluorescence lifetime (either shorter or longer). In one aspect of the invention, the indicator exhibits a 50-fold or greater change in net fluorescence emission intensity, and/or a 100% change in fluorescence lifetime in the presence of the target ion.

The spectral response of a selected indicator to a specific metal ion is a function of the characteristics of the indicator in the presence and absence of the target ion. For example, binding to a metal ion may alter the relative electron densities of the fluorophore and the metal binding site. Additionally, or in the alternative, some metal ions may quench fluorescence emission when in close proximity to a fluorophore (heavy atom quenching). In one embodiment of the invention, the indicator is essentially nonfluorescent or exhibits low fluorescence in target ion-free solution and exhibits an increase in fluorescence intensity or fluorescence lifetime (or both) upon target metal ion binding.

As the optical response of the indicating reagent is typically determined by changes in fluorescence, the threshold of detection of the target ion will be dependent upon the sensitivity of the equipment used for its detection.

If the optical response of the indicator will be determined using fluorescence measurements, the sample of interest is typically stained with indicator concentrations of $10^{-9}$ M to $10^{-3}$ M. The most useful range of analyte concentration includes about one log unit above and below the dissociation constant of the ion-indicator complex. This dissociation constant may be determined by titration of the indicator with known concentrations of the target ion, usually over the range of virtually zero concentration to approximately 100 mM of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects are readily determined, and can be taken into account when calibrating a selected indicator.

The indicator is typically combined with a sample in a way that will facilitate detection of the target ion concentration in the sample. The sample is generally a fluid or liquid suspension that is known or suspected to contain the target ion. Representative samples include intracellular fluids from cells such as in blood cells, cultured cells, muscle tissue, neurons and the like; extracellular fluids in areas immediately outside of cells; fluids in vesicles; fluids in vascular tissue of plants and animals; biological fluids such as blood, saliva, and urine; biological fermentation media; environmental samples such as water, soil, waste water and sea water; industrial samples such as pharmaceuticals, foodstuffs and beverages; and samples from chemical reactors. Detection and quantitation of the target ion in a sample can help characterize the identity of an unknown sample, or facilitate quality control of a sample of known origin.

In one embodiment of the invention, the sample includes cells, and the indicator is combined with the sample in such a way that the indicator is added within the sample cells. By selection of the appropriate chelating moiety, fluorophore, and the substituents thereon, indicators may be prepared that will selectively localize in a desired organelle, and provide measurements of the target ion in those organelles. Conjugates of the indicators of the invention with organelle-targeting peptides may be used to localize the indicator to the selected organelle, facilitating measurement of target ion presence or concentration within the organelle (as described in U.S. Pat. No. 5,773,227, hereby incorporated by reference). Alternatively, selection of a lipophilic fluorophore, or a fluorophore having predominantly lipophilic substituents may result in localization of the indicator in lipophilic environments in the cell, such as cell membranes. Selection of cationic indicators will typically result in localization of the indicator in mitochondria.

In one embodiment of the invention, the indicator compound of the invention optionally further includes a metal ion. In another embodiment, the compounds of the invention, in any of the embodiments described above, are associated, either covalently or noncovalently, with a surface such as a microfluidic chip, a silicon chip, a microscope slide, a microplate well, or another solid or semisolid matrix, and is combined with the sample of interest as it flows over the surface. In this embodiment, the detectable optical response may therefore be detected on the matrix surface itself, typically by use of instrumental detection. This embodiment of the invention may be particularly suited to high-throughput screening using automated methods.

The fluorescence response of the indicator to the target ion may be detected by various means that include without limitation measuring fluorescence changes with fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator may be covalently attached to the fiber optic probe material, typically glass or functionalized glass (e.g., aminopropyl glass) or the indicator may be attached to the fiber optic probe via an intermediate polymer, such as polyacrylamide. The indicator solution is alternatively incorporated non-covalently within a fiber optic probe, as long as there is a means whereby the target ion may come into contact with the indicator solution. More preferably, the BAPTA indicators of the invention are used with a fluorescence microplate reader that is equipped with an automated liquid handling system such as FLIPR, FlexStation and FDSS.

In another aspect of the invention, the fluorescent ion indicators of the invention may be used in combination with one or more non-fluorescent dyes that are not substantially cell-permeable in order to reduce the background fluorescence analogous to the methods described in U.S. Pat. No. 6,420,183, hereby incorporated by reference. Non-fluorescent dyes and dye mixtures that have large water solubilities and minimal effects on the physiology of the cells are preferred for this application. More preferably are water-soluble azo dyes (such as trypan blue), which have been used in cell-based assays for many years (H. W. Davis, R. W. Sauter. Histochemistry, 1977, 54, 177; W. E. Hathaway, L. A. Newby, J. H. Githens, Blood, 1964, 23, 517; C. W. Adams, O. B. Bayliss, R. S. Morgan, Atherosclerosis, 1977, 27, 353).

The screening methods described herein can be performed with cells growing in or deposited on solid surfaces. A common technique is to use a microwell plate where the fluorescence measurements are performing using a commercially available fluorescent plate reader. These methods lend themselves to use in high throughput screening using both automated and semi-automated systems.

Using the indicators of the present invention, the measurement of fluorescence intensity can provide a sensitive method for monitoring changes in intracellular ion concentrations. Thus, fluorescence measurements at appropriate excitation and emission wavelengths provide a fluorescence readout which is sensitive to the changes in the ion concentrations.

In one embodiment, the invention includes a) adding a compound as described above to a sample containing a cell; b) incubating the sample for a time sufficient for the compound to be loaded into the cell and an indicator compound to be generated intracellularly; c) illuminating the sample at a wavelength that generates a fluorescence response from the indicator compound; d) detecting a fluorescence response from the indicator compound; and e) correlating the fluorescence response with the presence of intracellular calcium.

In one aspect of the invention, the disclosed method is useful for screening potential therapeutic drugs, for example drugs which may affect ion concentrations in biological cells. These methods may include measuring ion concentrations as described above in the presence and absence (as a control measurement) of the test sample. Control measurements are usually performed with a sample containing all components of the test sample except for the putative drug being screened. Detection of a change in ion concentration in the presence of the test agent relative to the control indicates that the test agent is active. Ion concentrations can also be determined in the presence or absence of a pharmacologic agent of known activity (i.e., a standard agent) or putative activity (i.e., a test agent). A difference in ion concentration as detected by the methods disclosed herein allows one to compare the activity of the test agent to that of a standard agent of known activity. It will be recognized that many combinations and permutations of drug screening protocols are known to one of skill in the art and they may be readily adapted to use with the method of ion concentration measurement disclosed herein to identify compounds which affect ion concentrations.

Figure 7:
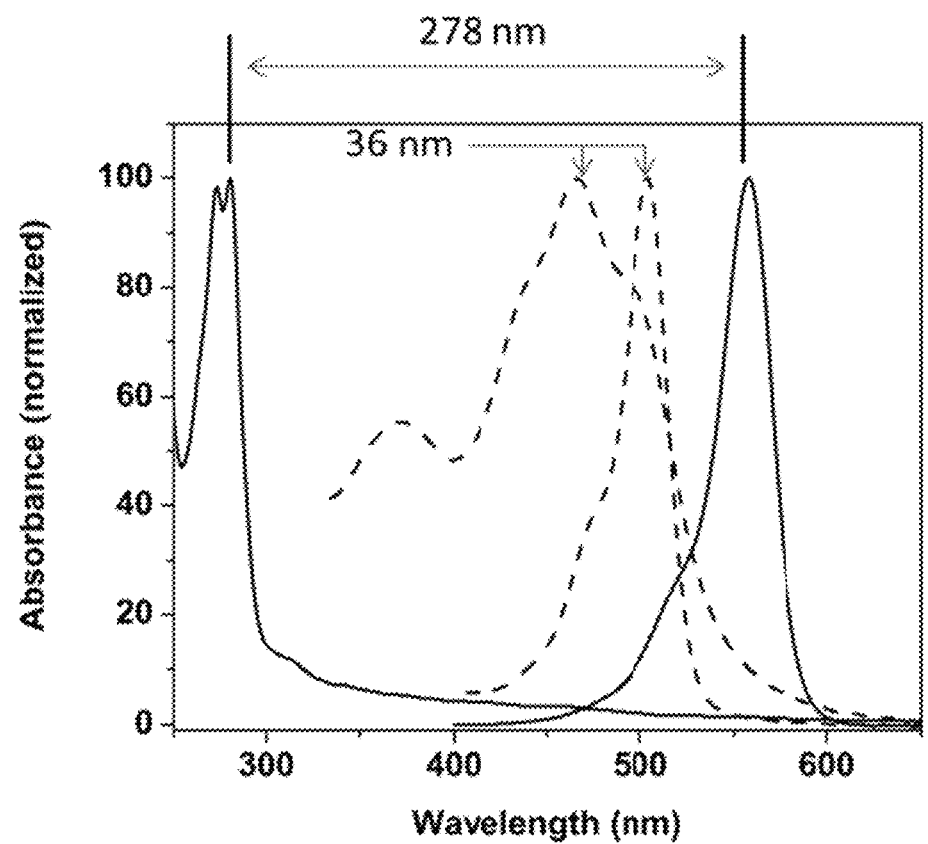
FIG. 7. The cell-induced absorption spectral shift comparison of Fluo-3 AM and Compound 16. The absorption spectra are normalized at their maximum absorption peak. Solid lines represent the absorption spectra of Compound 16 in the absence of CHO cells (left) and in the presence of CHO cells (right) respectively. Dot lines represent the absorption spectra of Fluo-3 AM in the absence of CHO cells (left) and in the presence of CHO cells (right) respectively.

Fluo-3 AM and Fluo-4 AM are predominantly used for monitoring intracellular calcium signal. However, Fluo-3 AM, Fluo-4 AM and their cell-hydrolyzed products (Fluo-3 and Fluo-4) can be simultaneously excited by the same excitation source (see FIGS. 7 and 8), causing high assay background. The present application is directed to a family of fluorescent dyes that are useful for preparing fluorescent metal ion indicators. The indicators include a carbofluorescein lactone fluorophore that is incorporated with an ionophore, and are useful for the detection, discrimination and quantification of metal cations. The fluorescent indicators of this invention demonstrate unexpected larger spectral shift upon cell-induced hydrolysis, as shown in Table 2, FIGS. 7 and 8.

TABLE 2

Spectral shift comparison

| Compound | Cell-Induced Excitation Wavelength Shift (nm) | Residual absorption of dye AM at the maximum excitation of dye acid |
|---|---|---|
| Fluo-3 AM | 36 nm | 7.6% |
| Compound 16 | 278 nm | 0% |
| Fluo-4 AM | 38 nm | 7.8% |
| Compound 85 | 277 nm | 0% |

The fluorescent indicators of this invention demonstrate unexpected emission shift to the longer wavelength as shown in Table 3. The red-shift excitation and emission wavelengths provide a great advantage for the use of current invention in the high throughput screening of new drug candidates since there are many fluorescent compounds of short wavelength in the screening compound libraries. Fluo-3 AM and Fluo-4 AM are currently used in the high throughput screening of new drug candidates, but their short wavelength overlap with the fluorescence of some fluorescent compounds in the screening compound libraries, causing severe interference.

TABLE 3

Spectral property comparison

| Compound | Excitation Wavelength (nm) | Emission Wavelength (nm) |
|---|---|---|
| Fluo-3 | 504 nm | 526 nm |
| Compound 11 | 558 nm | 584 nm |
| Fluo-4 | 493 nm | 515 nm |
| Compound 79 | 554 nm | 582 nm |

Figure 2:
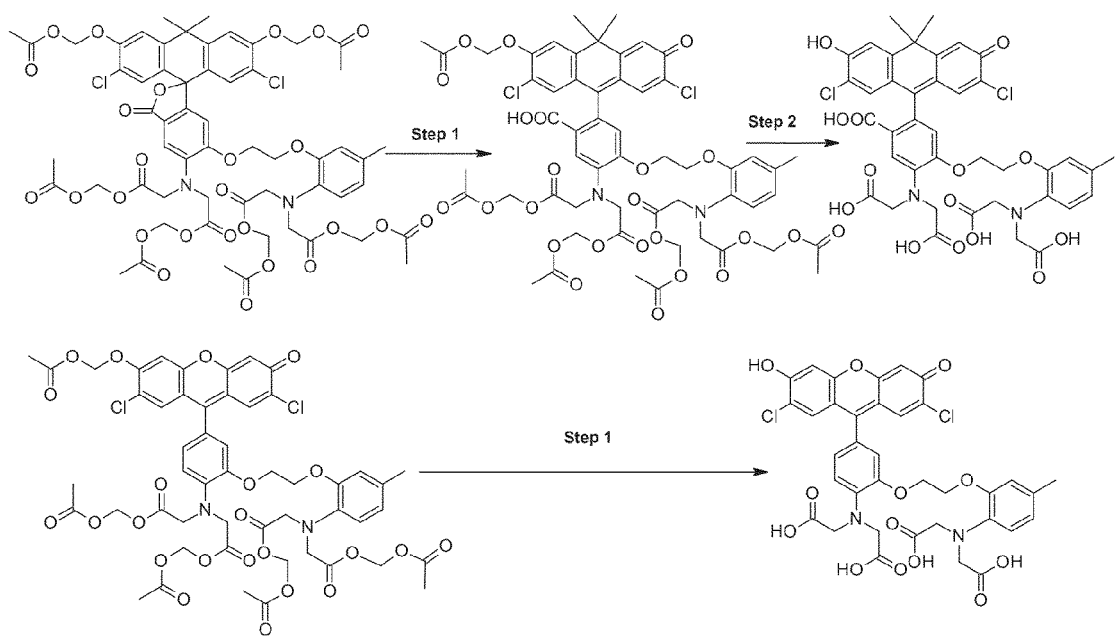
FIG. 2. The spontaneous hydrolysis of of Fluo-3 AM and Compound 128.
Figure 9:
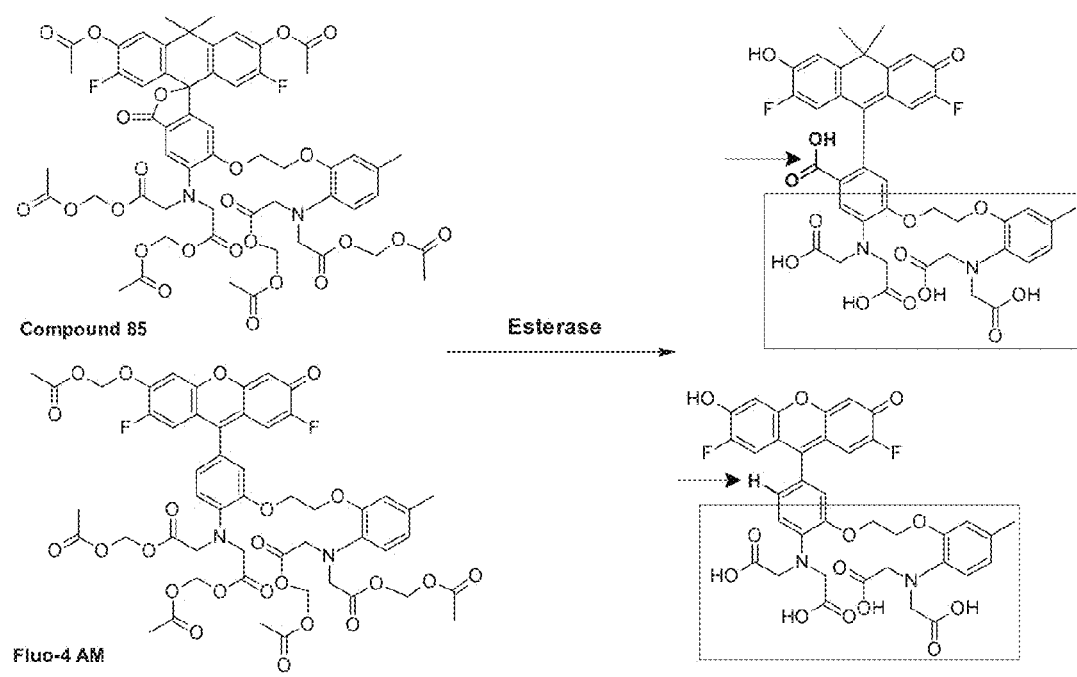
FIG. 9. The esterase-induced hydrolysis comparison of Compound 85 and Fluo-4 AM in live cells. Both of the compounds generate the same calcium-binding BAPTA moiety (marked in the rectangle). However, in live cells Compound 85 generates a fluorophore that carries an additional carboxy group, which significantly enhances the indicator fluorescence and retains the indicator from leaking out of cells.
Figure 10:
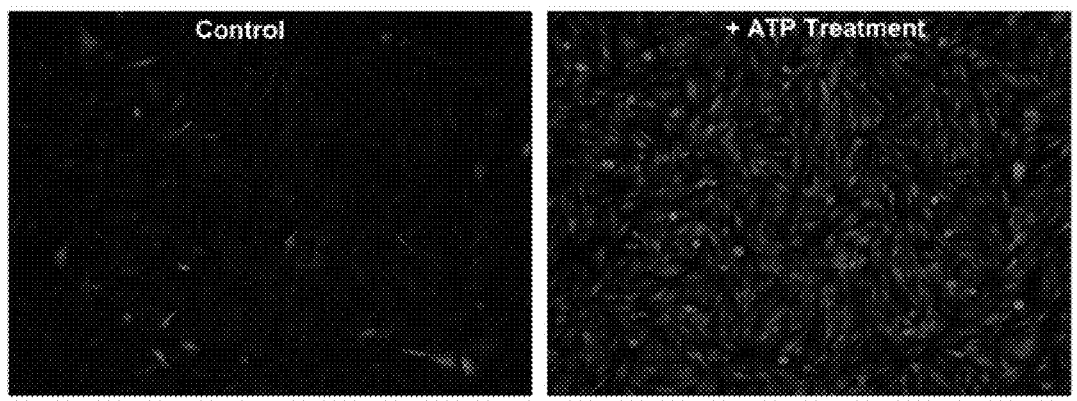
FIG. 10. Calcium responses of Compound 85 in CHO—K1 cells measured with a fluorescence microscope. CHO—K1 cells are seeded overnight at 50,000 cells per 100 µl per well in a 96-well black wall/clear bottom costar plate. The growth medium is removed, and the cells are incubated with 100 µl of Compound 85 at 5 µM in Hanks and Hepes buffer in the presence of 1 mM probenecid for 3 hours at 37° C., 5% $CO_2$ incubator. ATP (3 µM, 50 µL/well) was added, and imaged with a fluorescence microscope using TRITC channel.

The fluorescent indicators of this invention demonstrate better stability in the presence of cells and better cellular retention compared to the existing fluorescein ion indicators as shown in FIG. 2. The fluorescent indicators of this invention have double esterase-cleavable blocking groups that slow down the spontaneous hydrolysis in cell medium, thus reducing the assay background caused by the spontaneously hydrolyzed indicators. In addition, the fluorescent indicators of this invention provide an extra negative charge upon cell hydrolysis, reducing the hydrolyzed indicators from leaking out of cells, another factor that contributes the high assay background as shown in FIG. 9.

In one aspect of the invention, the disclosed calcium indicators have the minimal assay background in their masked form since their non-hydrolyzed AM esters cannot be excited in the range of visible wavelengths. As seen from FIG. 7, Compound 16 has essentially no absorption at 555 nm, the optimal excitation wavelength used for detecting intracellular calcium signal with Compound 16 while Fluo-3 AM has substantial absorption at 488 nm, the optimal excitation wavelength used for detecting intracellular calcium signal with Fluo-4 AM. Compound 16 and Fluo-3 AM are the masked form that does not bind calcium, shall not generate fluorescence signal unless binding calcium ion inside cells. The fluorescence outside cells generates the detrimental assay background. It is evident that the calcium indicators of the invention (e.g., Compound 16) have unexpected spectral properties that enable more sensitive detection of calcium in cells compared to the existing fluorescein-based calcium indicators (such as Fluo-3 AM).

Figure 8:
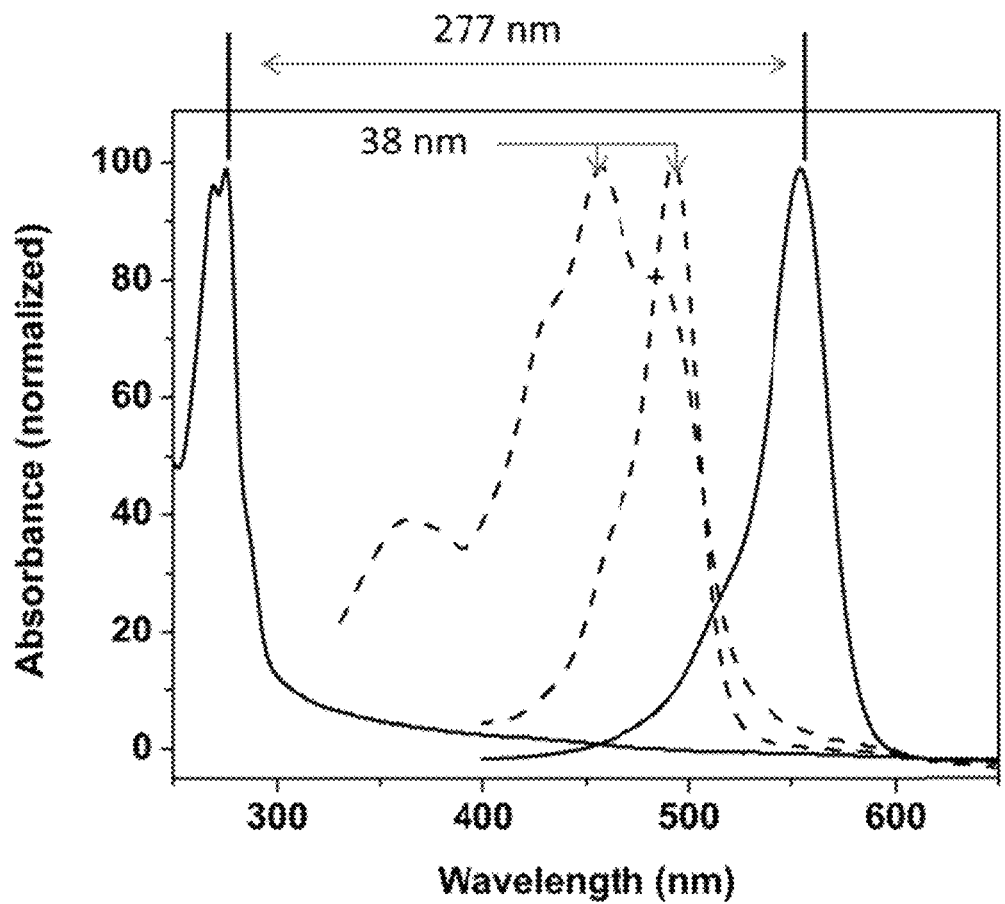
FIG. 8. The cell-induced absorption spectral shift comparison of Fluo-4 AM and Compound 85. The absorption spectra are normalized at their maximum absorption peak. Solid lines represent the absorption spectra of Compound 85 in the absence of CHO cells (left) and in the presence of CHO cells (right) respectively. Dot lines represent the absorption spectra of Fluo-4 AM in the absence of CHO cells (left) and in the presence of CHO cells (right) respectively.

As seen from FIG. 8, Compound 85 has essentially no absorption at 555 nm (the wavelength used to excite the deblocked Compound 85 inside cells) while Fluo-4 AM has substantial absorption at 488 nm (the wavelength used to excite the deblocked Fluo-4 AM inside cells). Compound 85 and Fluo-4 AM are the masked form that does not bind calcium, their fluorescence caused by 555 nm (for Compound 85) and 488 nm (for Fluo-4) excitation generates the detrimental assay background. It is evident that the calcium indicators of the invention (e.g., Compound 85) have unexpected spectral properties that enable more sensitive detection of calcium in cells compared to the existing fluorescein-based calcium indicators (such as Fluo-4 AM).

Figure 5:
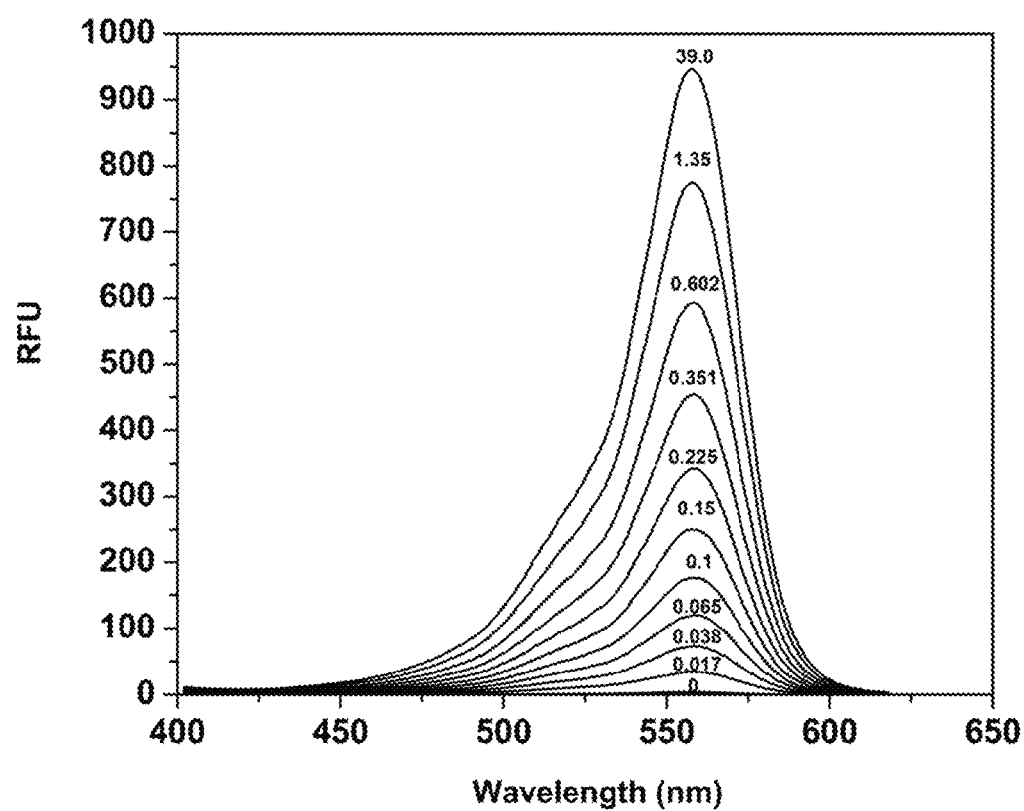
FIG. 5. Calcium responses of Compound 79 (5 μM) measured in fluorescence excitation in PBS buffer solution. The calcium concentrations are indicated in the graph in the unit of μM.
Figure 6:
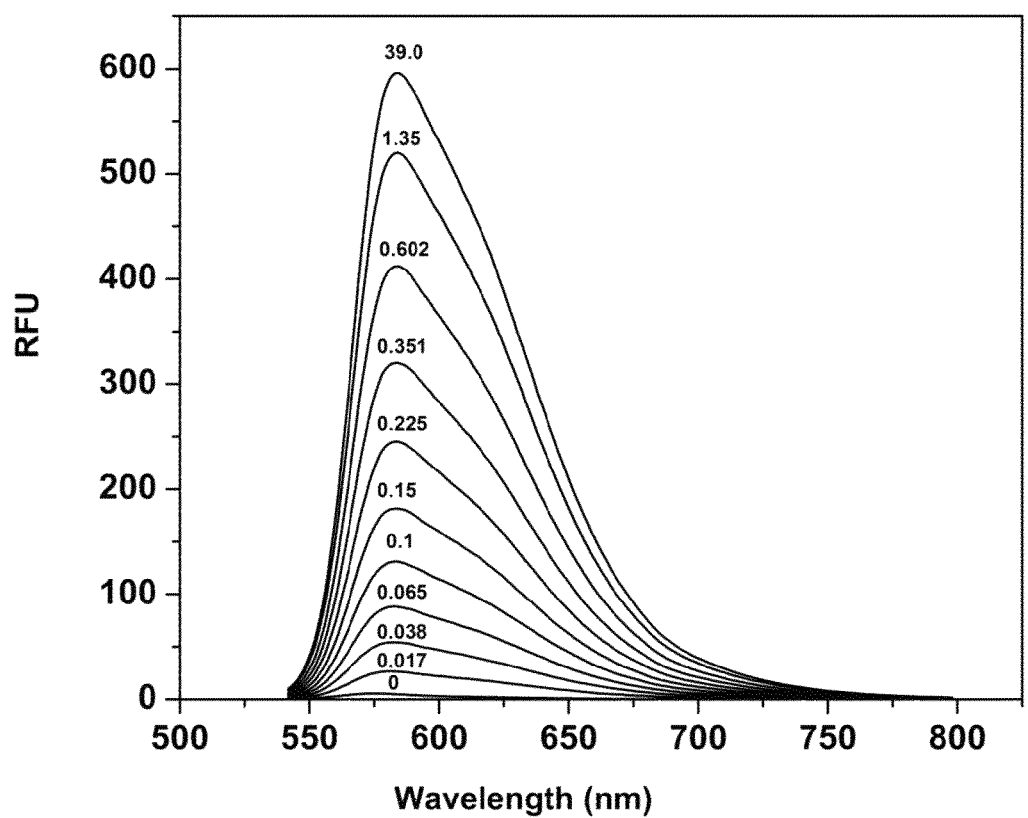
FIG. 6. Calcium responses of Compound 79 (5 μM) measured in fluorescence emission in PBS buffer solution. The calcium concentrations are indicated in the graph in the unit of μM.

FIG. 5 indicates that Compound 79 (the hydrolyzed product of Compound 85) binds calcium, and is well excited at 555 nm to give the fluorescence that is related to calcium concentration.

In yet another aspect of the invention, the fluorescent ion indicators are used in a method to measure calcium flux. Cells (e.g., CHO cells) stably transfected with muscarinic receptor 1 are plated—e.g., at 60,000 cells per 100 µl per well in F12 with 5% FBS and 1% glutamine in a 96-well black wall/clear bottom Costar plate—and incubated (e.g., in 5% $CO_2$ at 37° C. overnight). The growth medium is removed and the cells are incubated with a fluorescent ion indicator (e.g., with 100 µl/well of 1-8 µM Fluo-4 AM or Compound 85 in Hanks and HEPES buffer for 1 hour at room temperature) with or without probenecid. Carbachol is added (e.g., 50 µl/well by NOVOstar, FlexStation or FLIPR) to achieve a final concentration. Fluorescent ion indicators of the invention (e.g., Compound 85) load into cells much better than Fluo-4 AM, at certain ATP concentrations (e.g., 0.1 µM, 0.2 µM, 0.3 µM, 0.4 µM, 0.5 µM, 0.6 µM, 0.7 µM, 0.8 µM, 0.9 µM, 1.0, 10 or 100 µM) loading more than 10%, 20%, 30%, 40%, 50%, 60%, 70%, 80%, 90% or 100% faster. When probenecid is not used, the fluorescence intensity of a fluorescent ion indicator of the invention (e.g., Compound 85), is much greater than that of Fluo-4 AM. At certain ATP concentrations (e.g., 0.1 µM, 0.2 µM, 0.3 µM, 0.4 µM, 0.5 µM, 0.6 µM, 0.7 µM, 0.8 µM, 0.9 µM, 1.0, 10 or 100 µM) the intensity is more than 50%, 100%, 150%, 200%, 250%, 300%, 350% or 400% greater. The calcium indicators of the invention are unexpectedly well retained inside cells compared to the existing fluorescein-based calcium indicators (such as Fluo-3 and Fluo-4) that quickly leaks out of cell, another factor resulting higher assay background besides their high 488 nm absorption (see above). When probenecid is not used, Fluo-4 AM is not capable of detecting calcium in some types of cells and tissues for which Compound 85 is used.

In yet another aspect of the invention, the disclosed method may facilitate the screening of test samples in order to identify one or more compounds that are capable of modulating the activity of an ion channel, pump or exchanger in a membrane, and the method further includes stimulating the cell, monitoring changes in the intensity of the fluorescence response from the indicator compound, and correlating the changes in fluorescence intensity with changes in intracellular calcium levels.

An additional method may be used to evaluate the efficacy of a stimulus that generates a target ion response, including (a) loading a first set and a second set of cells with the ion indicators of the invention which monitor ion concentrations; (b) optionally, exposing both the first and second set of cells to a stimulus which modulates the ion channel, pump or exchanger; (c) exposing the first set of cells to the test sample; (d) measuring the ion concentrations in the first and second sets of cells; and (e) relating the difference in ion concentrations between the first and second sets of cells to the ability of a compound in the test sample to modulate the activity of an ion channel, pump or exchanger in cells. In one aspect of the recited method, the method may include the addition of probenecid or a probenecid derivative to the sample.

One or more of the methods disclosed herein may be enhanced by the addition of a cell-impermeant and non-fluorescent dye to the sample, such that the dye remains in the extracellular solution, and acts as an acceptor dye for energy transfer from the indicator compound, thereby decreasing background signal from the sample solution. In one aspect of the method, the cell-impermeant and non-fluorescent dye is a water-soluble azo dye.

Ion channels of particular interest may include, but are not limited to, sodium, calcium, potassium, nonspecific cation, and chloride ion channels, each of which may be constitutively open, voltage-gated, ligand-gated, or controlled by intracellular signaling pathways.

Biological cells of potential interest for screening application may include, but are not limited to, primary cultures of mammalian cells, cells dissociated from mammalian tissue, either immediately or after primary culture. Cell types may include, but are not limited to white blood cells (e.g. leukocytes), hepatocytes, pancreatic beta-cells, neurons, smooth muscle cells, intestinal epithelial cells, cardiac myocytes, glial cells, and the like. The disclosed method may also include the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel, hereby incorporated by reference) and methods for their expression in cell lines of interest are within the knowledge of one of skill in the art (see, U.S. Pat. No. 5,436,128, hereby incorporated by reference). Representative cultured cell lines derived from humans and other mammals include LM cells, HEK-293 (human embryonic kidney cells), 3T3 fibroblasts, COS cells, CHO cells, RAT1 and HepG2 cells, Hela cells, $U_2OS$ cells and Jurkat cells etc.

ASSAY KITS

Due to the advantageous properties and the simplicity of use of the disclosed ion indicator compounds, they possess particular utility in the formulation of a kit for the complexation, detection, or quantification of selected target ions. An exemplary kit may include one or more compounds or compositions of the invention in any of the embodiments described above, either present as a pure compound, in a suitable composition, or dissolved in an appropriate stock solution. The kit may further include instructions for the use of the indicator compound to complex or detect a desired target ion. The kit may further include one or more additional components, such as an additional detection reagent.

The indicator of the invention may be present in the kit associated with a surface, such as a chip, microplate well, or other solid or semi-solid matrix.

The additional kit components may be selected from, without limitation, calibration standards of a target ion, ionophores, fluorescence standards, aqueous buffers, surfactants and organic solvents. The additional kit components may be present as pure compositions, or as aqueous solutions that incorporate one or more additional kit components. Any or all of the kit components optionally further comprise buffers.

In one aspect of the disclosed kit, the kit includes at least one indicator compound as described above, and a non-fluorescent and cell-impermeant quencher dye. The non-fluorescent and cell-impermeant quencher dye is optionally present in a combined buffer solution with the compound, or the buffer solution of the cell-impermeant quencher dye is present in a separate container from the indicator compound.

The examples provided below illustrate selected aspects of the invention. They are not intended to limit or define the entire scope of the invention.

EXAMPLES

Example 1

Preparation of Compounds 3 and 4

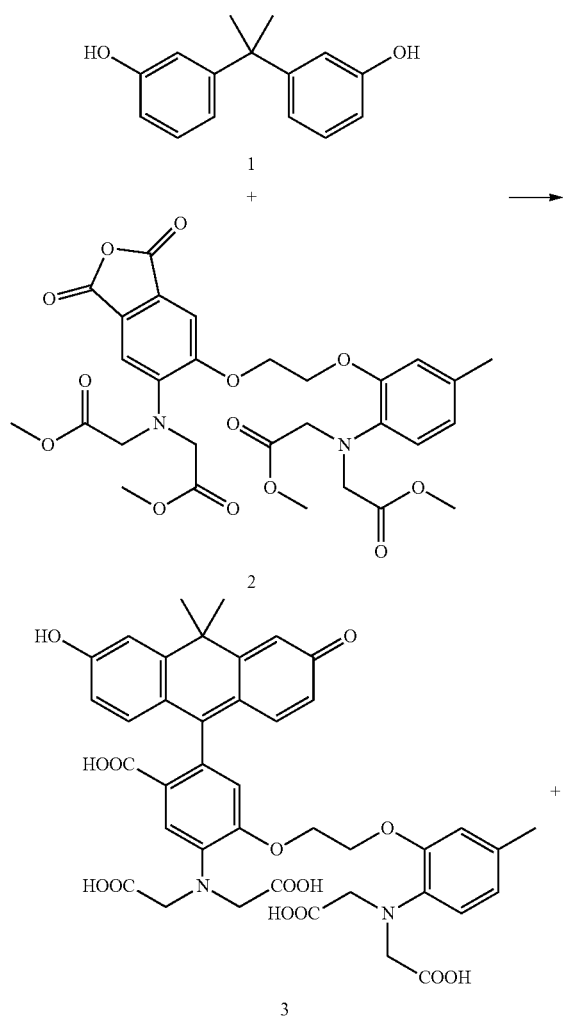

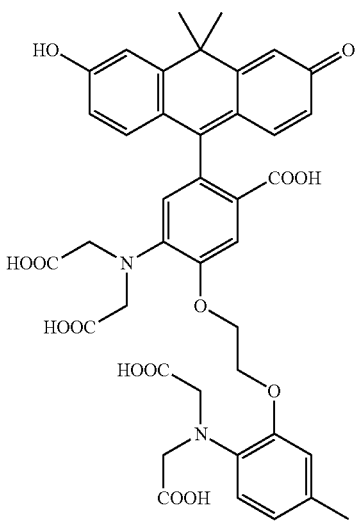

Compound 2 (20 g) is prepared according to the procedure of US Patent Application US20120183986 (Diwu et al). To the solution of Bisphenol 1 (5 g) in methanesulfonic acid (15 mL) Compound 2 is added with stirring. The resulting mixture is heated under dry nitrogen at 70-80° C. until Compound 1 is mostly consumed. The cooled mixture is poured into ice water. The reaction mixture is stirred at room temperature overnight to completely convert partially demethylated Compounds 3 and 4 to the mixture of free acid Compounds 3 and 4. The filtrate containing Compound 3 and its isomer 4 are dried, and purified on a silica gel column eluted with a gradient of water/acetonitrile to give the mixture of Compound 3 and its isomer 4. The mixture of Compounds 3 and 4 is further purified by HPLC using C18 column and a gradient of 0.1% triethylammonium acetate acetonitrile-0.1% triethylammonium acetate buffer to give the pure Compounds 3 and 4.

Example 2

Preparation of Compound 8

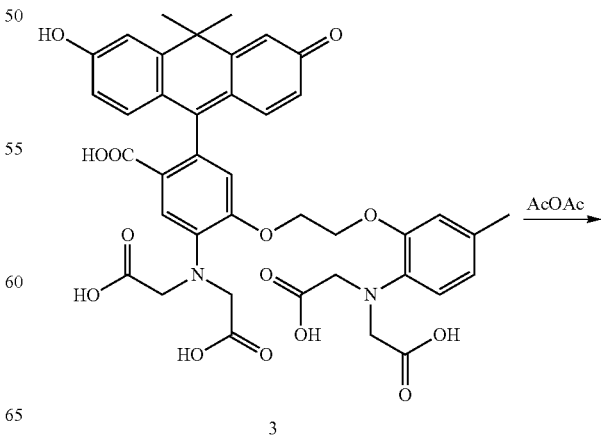

73
-continued

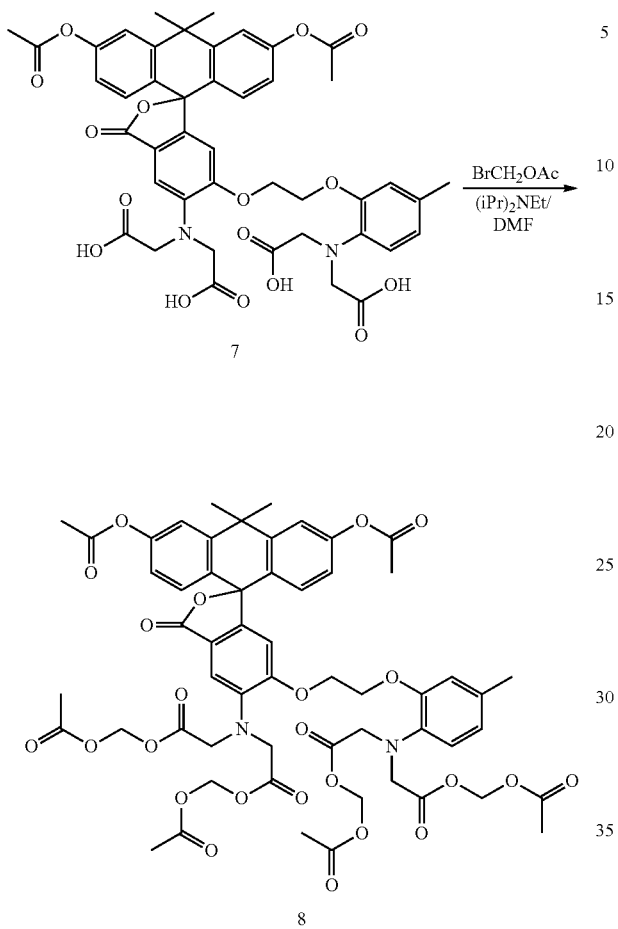

Compound 3 (50 mg) is heated at 80° C. with Ac₂O (5 mL) and pyridine (0.1 mL) until Compound 3 is completely consumed. The solution is cooled to room temperature. The reaction mixture is poured into ice water, and carefully adjusted to pH=4-5. The aqueous mixture is titrated with dioxane to give a precipitate that is collected by filtration. The resulting mixture is first air-dried, and further vacuum-dried in a desiccator with P₂O₅ for 12 hours to yield crude Compound 7 that is directly used for next step reaction.

The crude Compound 7 (50 mg) is dissolved in anhydrous DMF (2 mL) at room temperature. To the solution of Compound 7 BrCH₂OAc (0.1 mL) was slowly added while stirring in a water bath. To the resulted mixture iPr₂NEt (0.3 mL) is added slowly. The reaction mixture is stirred until Compound 7 is completely consumed and concentrated in vacuo. The residue is suspended in ethyl acetate (20 mL) and stirred for 1-2 hours. The mixture is filtered to remove the solid that is washed with ethyl acetate, and the filtrate is evaporated to dryness. The filtrate residue is purified on a silica gel column using 3:1:1 hexanes/EtOAc/chloroform as an eluent to give the desired Compound 8.

74

Example 3

Preparation of Compound 9

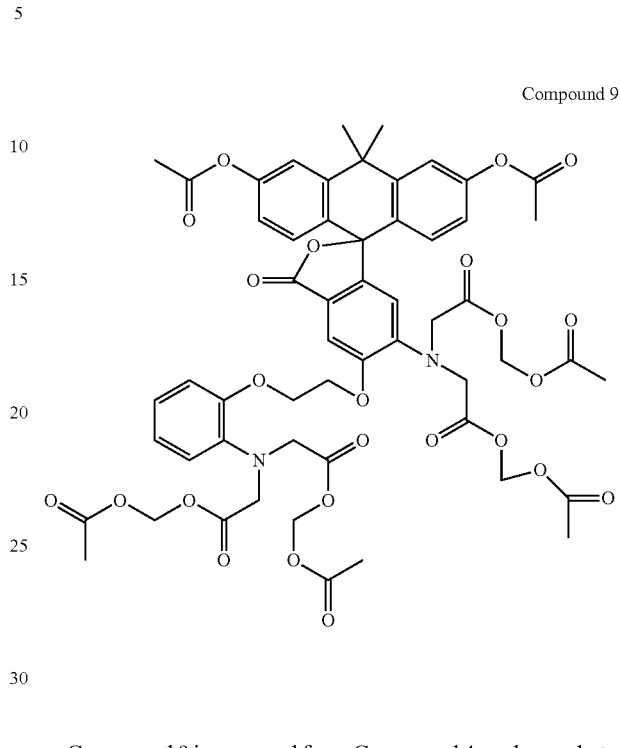

Compound 9 is prepared from Compound 4 analogously to the procedure of Compound 8.

Example 4

Preparation of Compounds 11 and 12

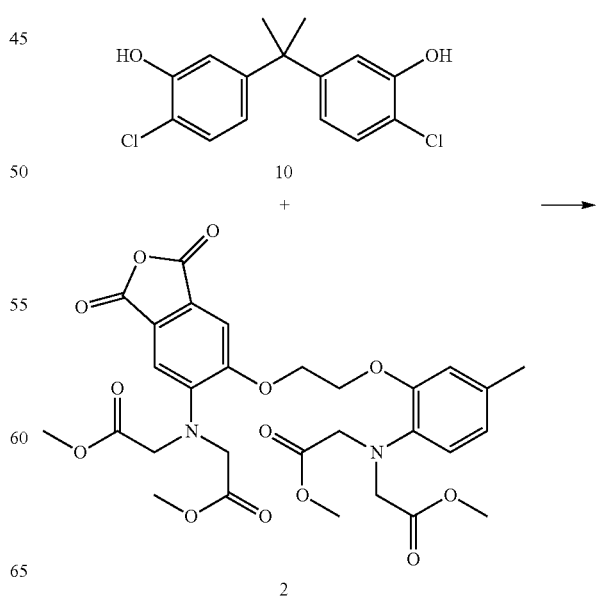

75

-continued

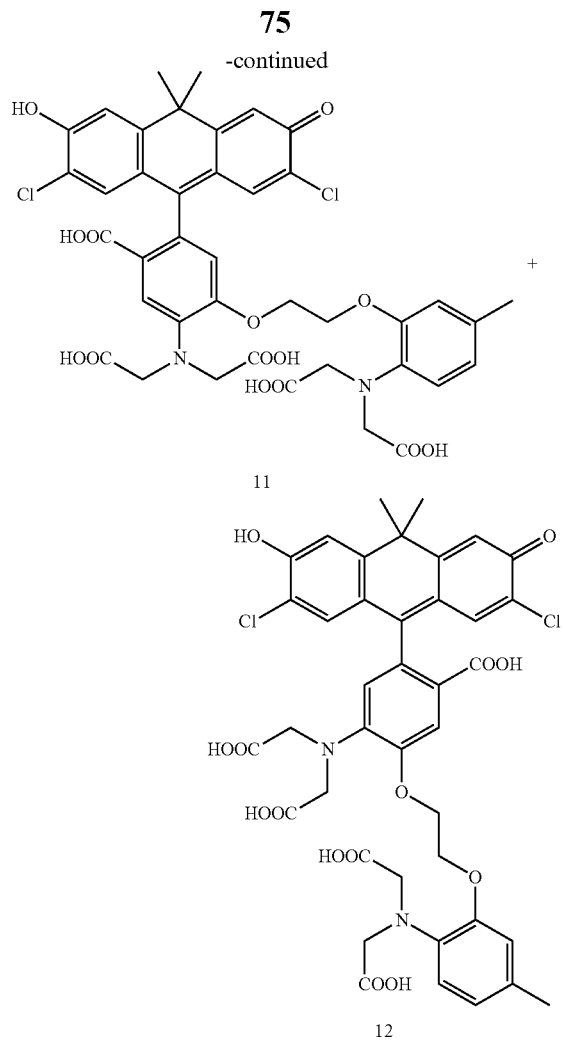

11

12

The mixture of Compounds 11 and 12 are prepared from the reaction of Bisphenol 10 with Compound 2 analogously to the procedure of Compounds 3 and 4. The mixed Compound 11 and its isomer 12 are further purified by HPLC using C18 column and a gradient of 0.1% triethylammonium acetate acetonitrile-0.1% triethylammonium acetate buffer to give the pure Compound 11 and 12.

Example 5

Preparation of Compound 16

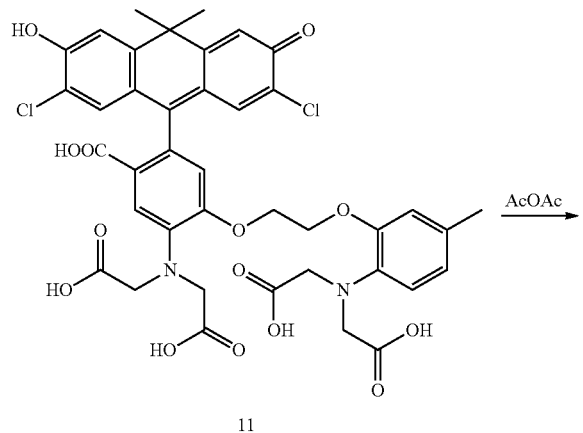

11

76

-continued

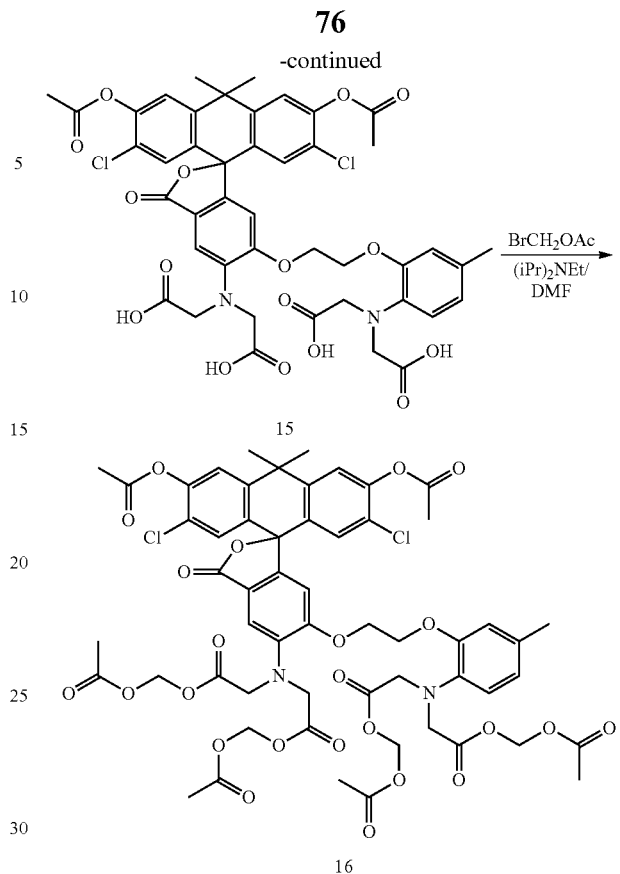

15

16

Compound 16 is prepared from Compound 11 analogously to the procedure of Compound 8.

Example 6

Preparation of Compound 18

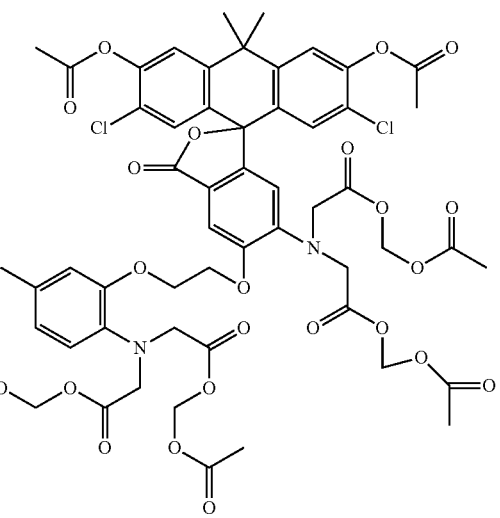

Compound 18

Compound 18 is prepared from Compound 12 analogously to the procedure of Compound 8.

Example 7

Preparation of Compound 20

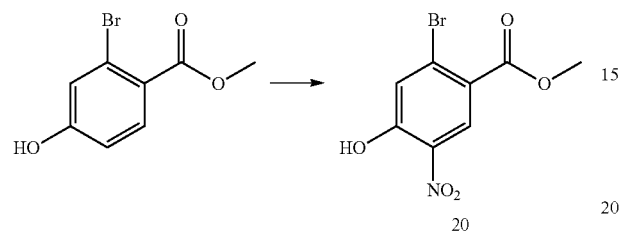

Example 9

Preparation of Compound 30

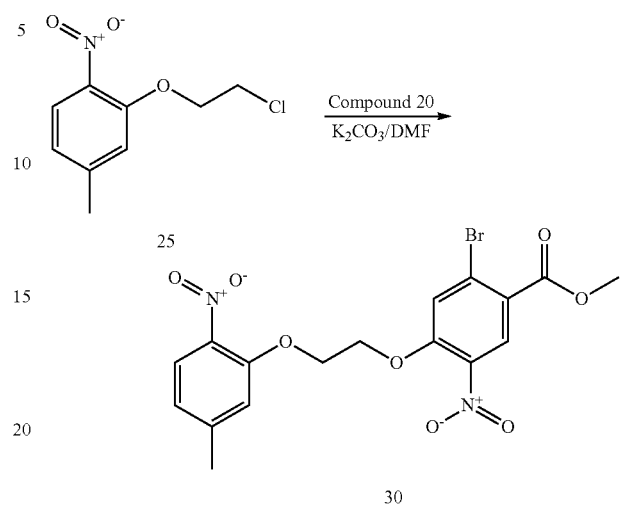

Methyl 2-Bromo-4-hydroxybenzoate (100 g) is suspended in acetic acid (200 ml), and cooled to 0° C. To the suspension is dropwise added fuming nitric acid (45 ml). The reaction mixture is stirred at 0° C. for 2 hours, and slowly warmed to room temperature. The reaction is continued until methyl 2-bromo-4-hydroxybenzoate is completely consumed. The reaction mixture is poured to ice water, and the resulted mixture is filtered to give yellow solid product that is further purified on a silica gel column using a gradient of methanol and chloroform as eluent.

The mixture of Compound 20 (20 g) and 25 (20 g) is dissolved in DMF at room temperature. To the reaction mixture $K_2CO_3$ is added, and the reaction mixture is stirred at 140-160° C. for 12-24 h. The reaction mixture is cooled, and poured into water, and resulted solid is collected. The dried solid is purified on a silica gel column using a gradient of hexanes/ethyl acetate to give a very light yellow solid.

Example 8

Preparation of Compound 25

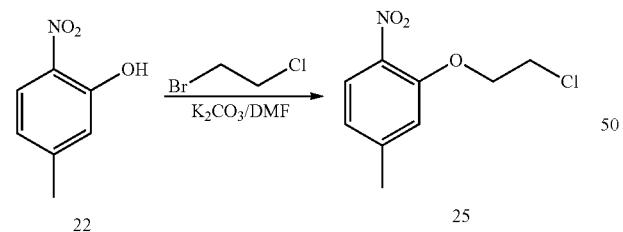

Example 10

Preparation of Compound 35

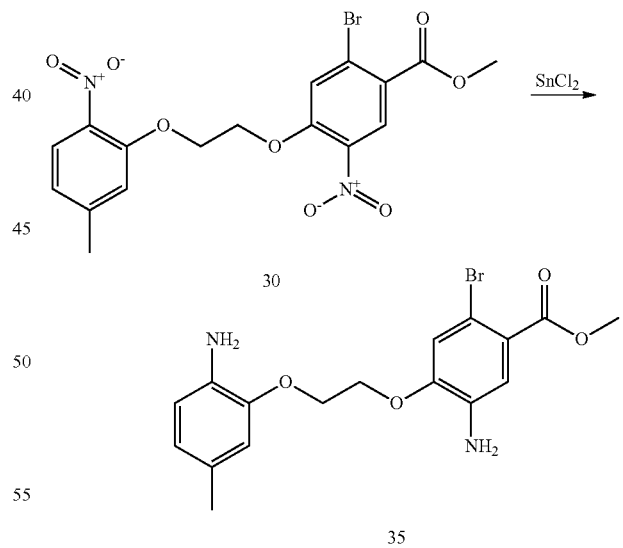

Compound 25 is analogously prepared according to the procedure of U.S. Application No. 2002/0164616. A mixture of Compound 22 (15 g) and 1-bromo-2-chloroethane (50 g) is dissolved in DMF at room temperature. To the reaction mixture $K_2CO_3$ is added with stirring. The reaction mixture is stirred at room temperature for 4-6 days. The reaction mixture is poured into water, and the resulted solid is collected. The dried solid is purified on a silica gel column using a gradient of hexanes/ethyl acetate to give a light yellow solid.

Compound 30 (30 g) is dissolved in methanol (200 ml) at room temperature. To the MeOH solution is added stannous chloride dihydrate (25 g). The reaction mixture is heated with stirring at 70-80° C. until Compound 30 is completely consumed. The reaction mixture is cooled to room temperature, and poured into ice/water. The resulted suspension is extracted with ethyl acetate (3×500 ml), and combined organic phase is dried over anhydrous sodium sulfate. The solution is evaporated under vacuum to give a crude solid. The dried solid is purified on a silica gel column using a gradient of chloroform/ethyl acetate to give an off-white solid.

Example 11

Preparation of Compound 45

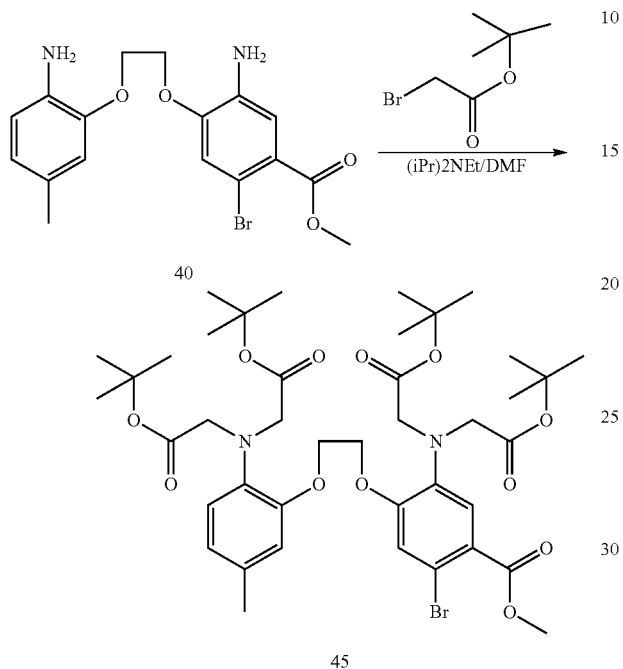

To the solution of Compound 40 (20 g) and (iPr)₂NEt (50 mL) in DMF (100 ml) is added tert-butyl bromoacetate (100 mL) with stirring. The reaction mixture is refluxed until Compound 40 is completely consumed. The concentrated DMF solution is poured into water. The formed solid is collected by filtration, and washed with water. The dried solid is purified on a silica gel column using a gradient of chloroform/ethyl acetate to give an off-white solid.

Example 12

Preparation of Compound 50

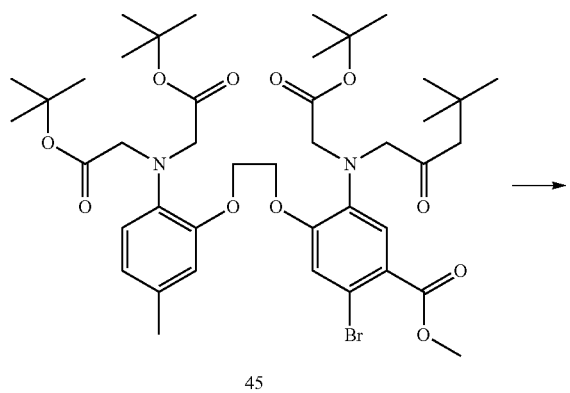

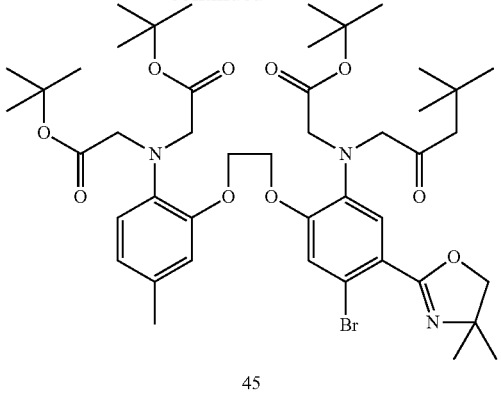

To the solution of Compound 45 (5 g) in methanol (100 ml) is added with stirring 1 M KOH (20 mL) is added with stirring at 0° C. The reaction mixture is stirred at 0° C. until the maximum amount of Compound 45 monoacid is formed. The reaction mixture is carefully neutralized to pH 7.5 with 1M HCl. The concentrated MeOH solution is poured into water. The formed solid is collected by filtration, and washed with water. The crude solid is dried under high vacuum to give an off-white solid. The completely dried solid is dissolved in dichloromethane (100 ml), and cooled to 0° C. To the dichloromethane solution is added oxalyl chloride (5 ml) at 0° C., and followed with the addition of 3 drops of DMF. The reaction mixture was warmed to room temperature, and stirred for 6 hours. The reaction solution was concentrated under vacuum, and residue was added to cold ether to give a suspension. The suspension is filtered to collect the formed solid that is completely dried under high vacuum. The dried solid is immediately dissolved in dichloromethane (50 ml). To the dichloromethane solution is dropwise added 2,2-dimethylethanolamine (5 ml), and followed by the dropwise addition of triethylamine (5 ml). The reaction solution is stirred at room temperature until Compound 45 monoacyl chloride is consumed. The reaction solution is diluted with dichloromethane (150 ml), washed with saturated sodium bicarbonate and brine. The organic phase is dried over anhydrous sodium sulfate, and evaporated under vacuum to give a gummy solid. The crude solid is dissolved in DMF (50 ml), and followed by the addition of N,N'-dicyclohexylcarbodiimide (1 g). The DMF solution is stirred at ~50° C. overnight, and filtered to collect the filtrate. The filtrate is concentrated, and poured to water (100 ml) to collect the crude solid. The crude solid is dried and purified on a silica gel column using a gradient of dichloromethane/ethyl acetate to give an off-white solid.

Example 13

Preparation of Compound 70

Compound 50 (10 g) is suspended in dichloromethane (40 ml). To the suspension is added oxalyl chloride (8 ml), and followed by the addition of DMF (20 μL). The reaction mixture is stirred until Compound 50 is completely consumed. The reaction mixture is concentrated, followed by azeotrope with dichloromethane twice. The resulting oil is dried under high vacuum, and redissolved in dichloromethane (80 ml). To the dichloromethane solution is added Compound 51 (12 g), followed by the addition of AlCl₃ (10.6 g) portionwise in ice bath. The reaction mixture is stirred at room temperature until the amount of Compound 52 is maximized, and the reaction mixture is diluted with dichloromethane and poured onto ice. The mixture is sequentially washed with water and saturated Na₂CO₃. The organic phase is dried by MgSO₄, filtered, and concentrated to give the crude. The crude is purified on a silica gel column with a gradient of hexanes/EtOAc to give Compound 52 as a white solid. Compound 52 is readily converted to Compound 56 according to the procedure of J. B. Grimm et al. (ACS Chem Biol 2013, 8, 1303-1310).

Example 14

Preparation of Compound 79

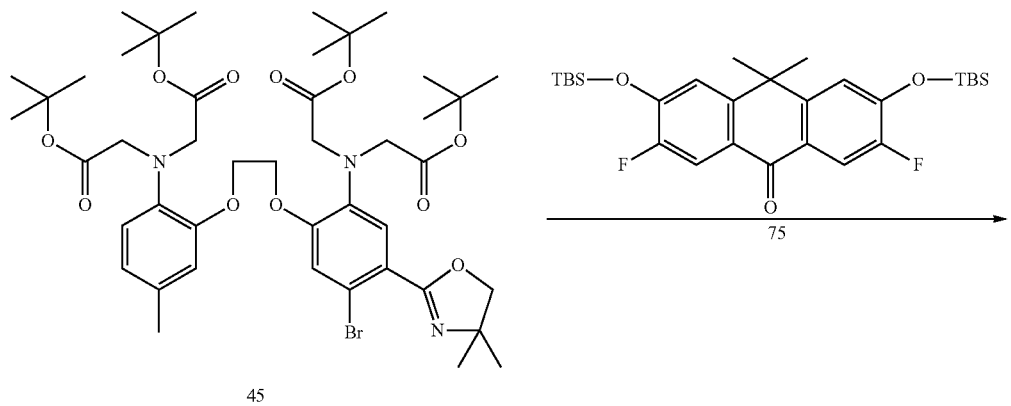

45

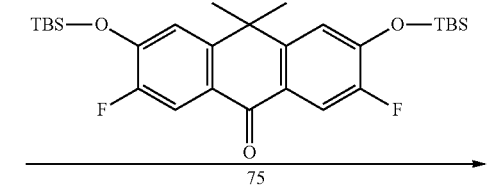

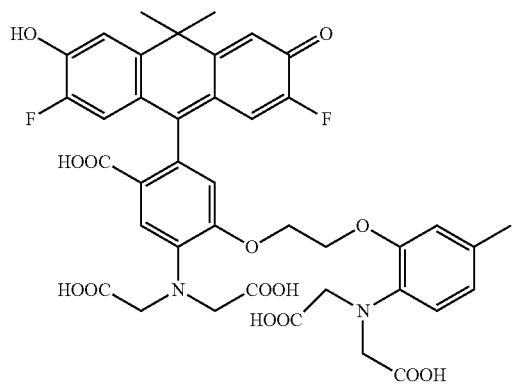

79

Compound 79 is prepared analogously to the procedure of J. B Grimm et al. (ACS Chem Biol 2013, 8, 1303-1310). Compound 45 (1.2 g) is dissolved in methyltetrahydrofuran, and the solution is cooled to −150° C. To the cold solution of Compound 45 is added 1.7 M t-BuLi (5 ml). The solution is stirred at −150° C. for 2 hours. The solution of Compound 75 (1.1 g) in methyltetrahydrofuran (20 ml) is carefully added to maintain the reaction solution around −150° C. The reaction solution is stirred at −150° C. for 2 hours. To the reaction mixture is carefully added 1:1 water/tetrahydrofuran (50 ml) to stop the reaction. The reaction mixture is extracted with EtOAc, and the organic phase is washed with brine, and dried over sodium sulfate. The EtOAc solution is evaporated under vacuum, and the residue is redissolved in THF (50 ml). To the THF solution is added tetrabutylammonium fluoride, and stirred until the solution change to red. The solution is evaporated under vacuum, and redissolved in EtOAc. The EtOAc solution is washed with water for three times, and dried over sodium sulfate. The resulted EtOAC solution is evaporated under vacuum, and the residue is suspended in 20% HCl (50 ml), and heated at 70-80° C. until the amount of Compound 79 is maximized. The crude product is further purified on a C18 reverse phase silica gel column with a gradient of triethylammonium bicarbonate buffer/acetonitrile.

Example 15

Preparation of Compound 85

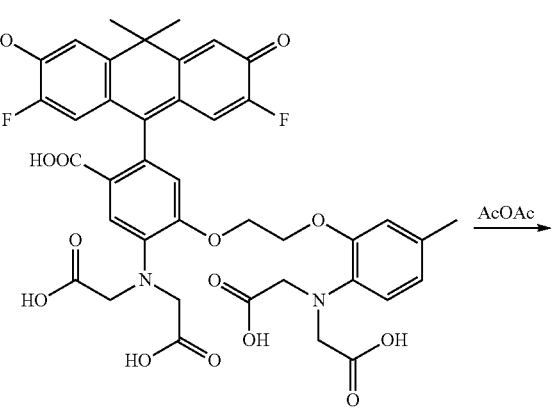

79

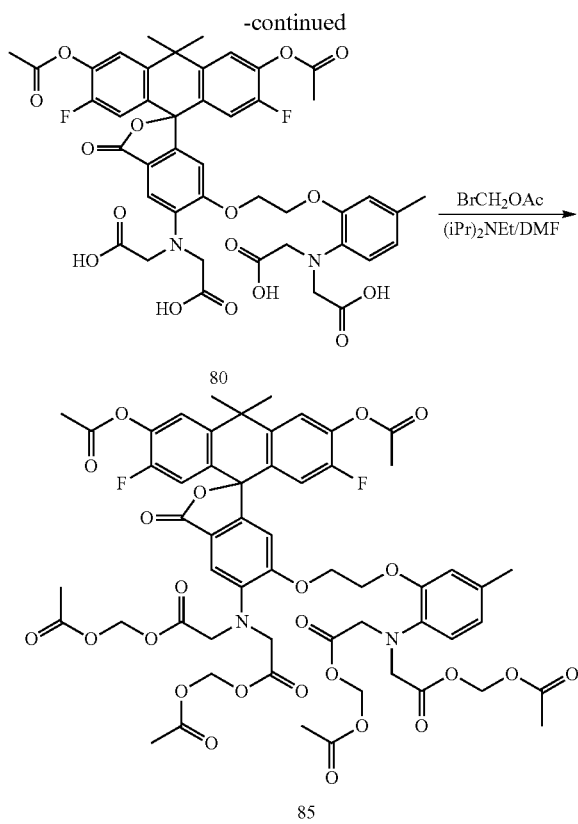

Compound 85 is prepared from Compound 79 analogously to the procedure of Compound 8.

Example 16

Preparation of Compound 89

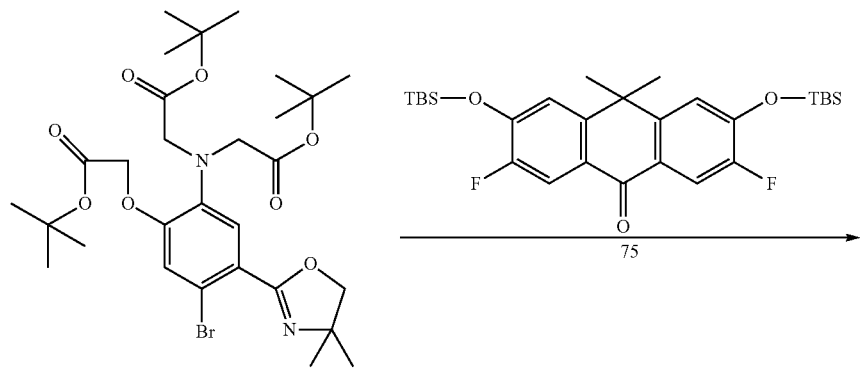

Compound 87 (200 mg) is dissolved in methyltetrahydrofuran, and solution is cooled to −150° C. To the cold solution of Compound 87 is added 1.7 M t-BuLi (1 ml). The solution is stirred at −150° C. for 1 hour. The solution of Compound 75 (180 mg) in methyltetrahydrofuran (5 ml) is carefully added to maintain the reaction solution around −150° C. The reaction solution is stirred at −150° C. for 1 hour. To the reaction mixture is carefully added 1:1 water/tetrahydrofuran (10 ml) to stop the reaction. The reaction mixture is extracted with EtOAc, and the organic phase is washed with brine, and dried over sodium sulfate. The EtOAc solution is evaporated under vacuum, and the residue is redissolved in THF (10 ml). To the THF solution is added tetrabutylammonium fluoride, and stirred until the solution change to red. The solution is evaporated under vacuum, and redissolved in EtOAc. The EtOAc solution is washed with water for three times, and dried over sodium sulfate. The resulted EtOAC solution is evaporated under vacuum, and the residue is suspended in 20% HCl (5 ml), and heated at 70-80° C. until the amount of Compound 89 is maximized. The crude product is further purified on a C18 reverse phase silica gel column with a gradient of triethylammonium bicarbonate buffer/acetonitrile.

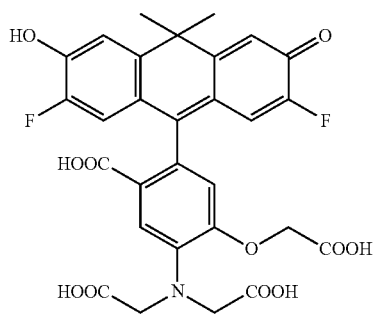

Example 17

Preparation of Compound 93

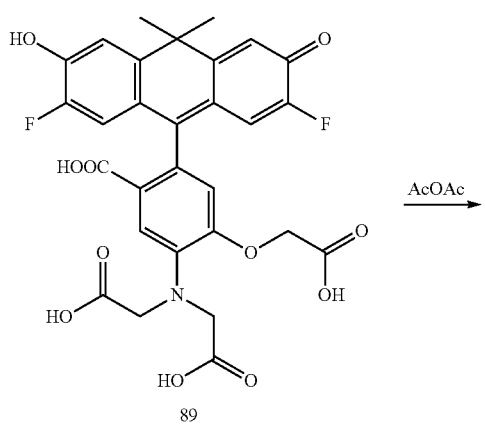

89

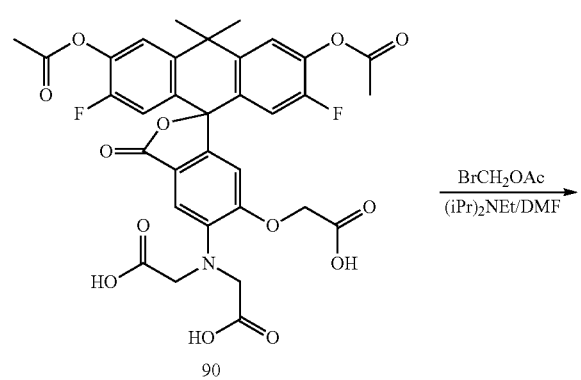

90

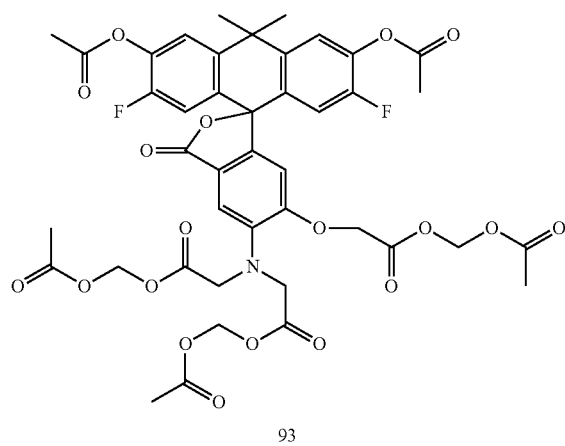

93

Compound 93 is prepared from Compound 89 analogously to the procedure of Compound 8.

Example 18

Preparation of Compound 97

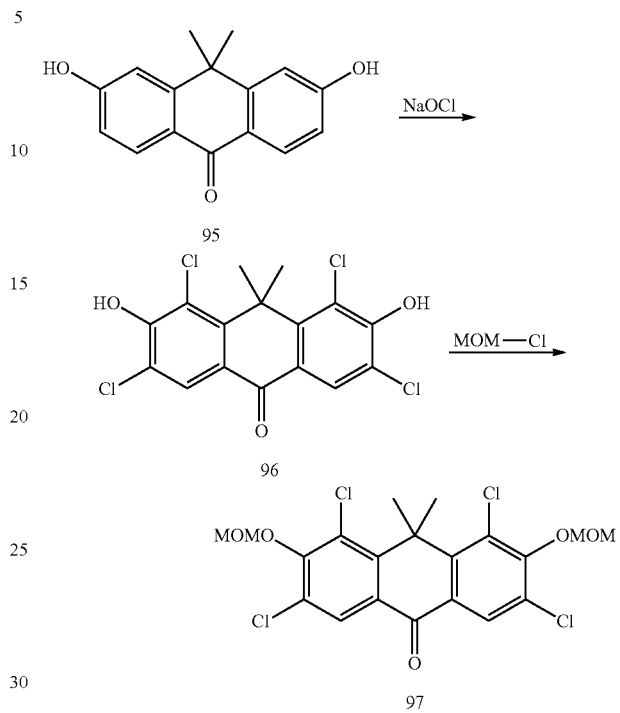

Compound 95 is prepared according to the procedure of J. B. Grimm et al. (ACS Chem Biol 2013, 8, 1303-1310). To the solution of Compound 95 (0.1 g) in MeOH (5 ml) is dropwise added the mixture of NaOCl (0.6 ml, 10% aqueous solution) and 0.1 N NaOH (4 ml) at room temperature. Multiple portions of the mixed solution of NaOCl (0.4 ml) and 0.1 N NaOH (3 ml) is added at every hour until Compound 95 is completely consumed. The reaction is neutralized with 0.2 N HCl. The mixture is extracted with EtOAc and the organic phase is dried with anhydrous $Na_2SO_4$, filtered, and concentrated to give the crude solid. The crude material is further purified on a silica gel column with a gradient of hexanes/EtOAc to give Compound 96 as a light yellow solid. To the solution of Compound 96 (0.31 g) in THF (15 ml) is added $iPr_2NEt$ (0.69 ml) and MOM-Cl (1.2 ml, 2M toluene solution) in ice bath. The reaction is stirred at room temperature until Compound 96 is completely consumed. The reaction is worked with the addition of saturated aqueous $NH_4Cl$. The mixture is extracted with EtOAc and the organic phase is dried with anhydrous $Na_2SO_4$, filtered, and concentrated to give the crude solid. The crude material is further purified on a silica gel column with a gradient of hexanes/EtOAc to give Compound 97 as a pale yellow wax.

Example 19

Preparation of Compound 100

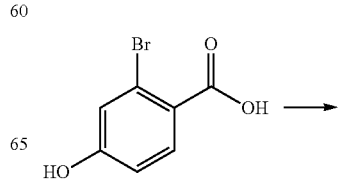

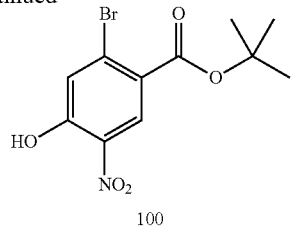

100

2-Bromo-4-hydroxybenzoic acid (100 g) is suspended in acetic acid (200 ml), and cooled to 0° C. To the suspension is dropwise added fuming nitric acid (45 ml) at 0° C. The reaction mixture is stirred at 0° C. for 2 hours, and slowly warmed to room temperature. The reaction is continued until 2-Bromo-4-hydroxybenzoic acid is mostly consumed. The reaction mixture is poured to ice water, and the resulted mixture is filtered to give yellow solid product that is further purified on a silica gel column using a gradient of methanol and chloroform as eluent. 2-Bromo-4-hydroxy-5-nitrobenzoic acid is converted to Compound 100 according the procedure of U. Schmidt et al. (J. Org. Chem. 1983, 48, 2680-2685).

Example 20

Preparation of Compound 105

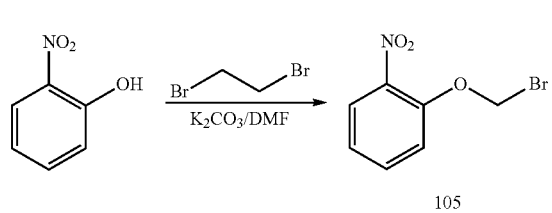

105

Compound 25 is analogously prepared according to the procedure of U.S. Pat. No. 4,689,432.

Example 21

Preparation of Compound 110

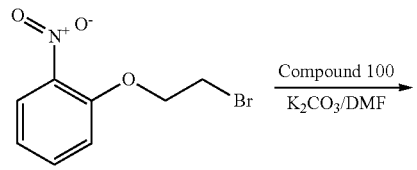

105

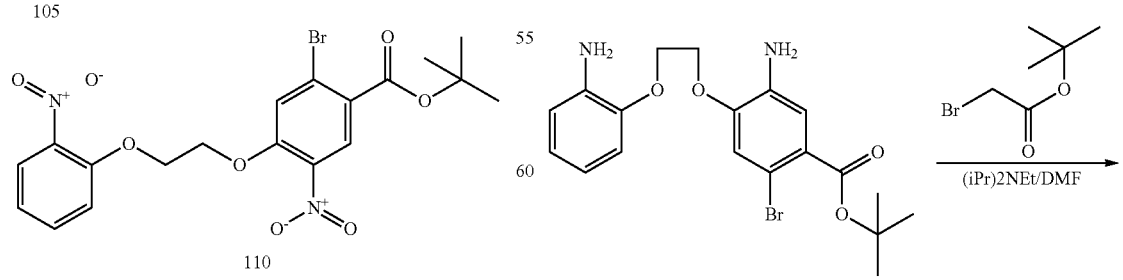

110

The mixture of Compound 105 (40 g) and 100 (20 g) is dissolved in DMF at room temperature. To the reaction mixture $K_2CO_3$ is added, and the reaction mixture is stirred at 140-160° C. for 12-24 h. The reaction mixture is cooled, and poured into water, and resulted solid is collected. The dried solid is purified on a silica gel column using a gradient of hexanes/ethyl acetate to give a very light yellow solid.

Example 22

Preparation of Compound 113

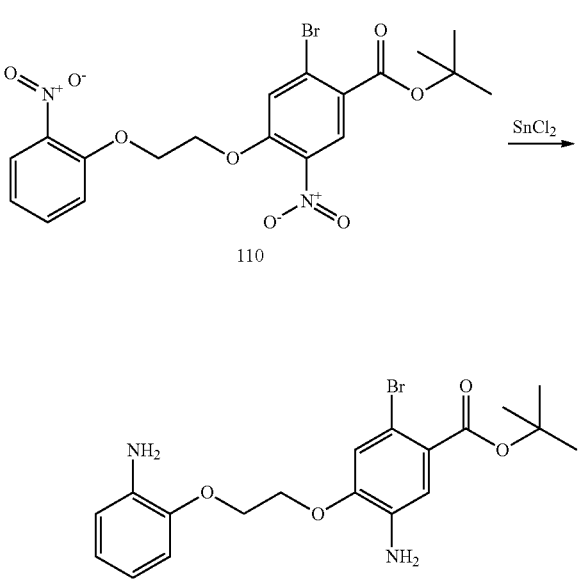

Compound 110 is reduced to Compound 113 analogously to the procedure of Compound 35.

Example 23

Preparation of Compound 115

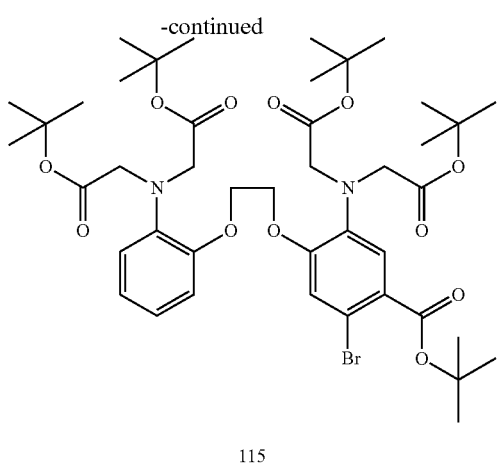

115

Compound 113 is converted to Compound 115 by t-butyl-bromoacate alkylation analogously to the procedure of Compound 45.

Example 24

Preparation of Compound 120

Compound 115 (220 mg) is dissolved in methyltetrahydrofuran (3 ml), and solution is cooled to −150° C. To the cold solution of Compound 115 is added 1.7 M t-BuLi (0.9 ml). The solution is stirred at −150° C. for 1 hour. To the solution of Compound 115 the solution of Compound 97 (240 mg) in methyltetrahydrofuran (3 ml) is carefully added to maintain the reaction solution around −150° C. The reaction solution is stirred at −150° C. for 2 hours. To the reaction mixture is carefully added 1:1 water/tetrahydrofuran (5 ml) to stop the reaction. The reaction mixture is extracted with EtOAc, and the organic phase is washed with brine, and dried over sodium sulfate. The EtOAc solution is evaporated under vacuum, and the residue is redissolved in dichloromethane (3 ml). To the dichloromethane solution is added trifluoroacetic acid (3 ml), and followed by the addition of anisole (0.1 ml), and stirred at room temperature until the solution change to red. The solution is evaporated under vacuum, and redissolved in water. The aqueous solution is washed with EtOAc for three times. The resulted aqueous solution is concentrated under high vacuum, and the residue is further purified on a C18 reverse phase silica gel column with a gradient of triethylammonium bicarbonate buffer/acetonitrile.

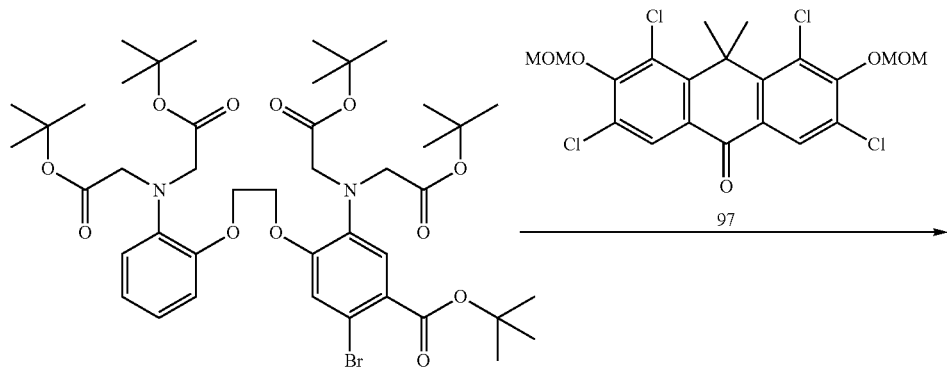

115

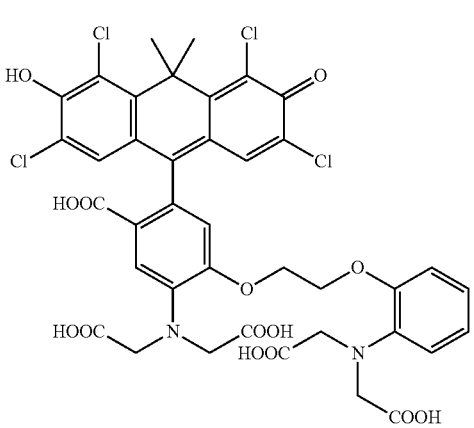

120

Example 25

Preparation of Compound 125

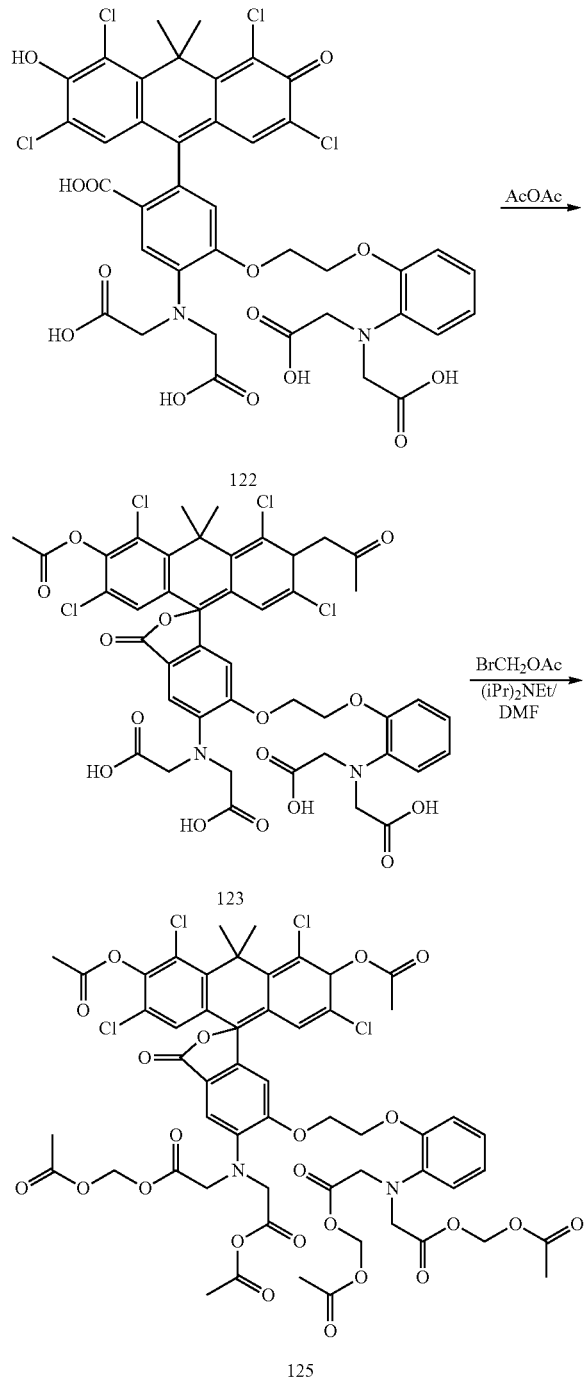

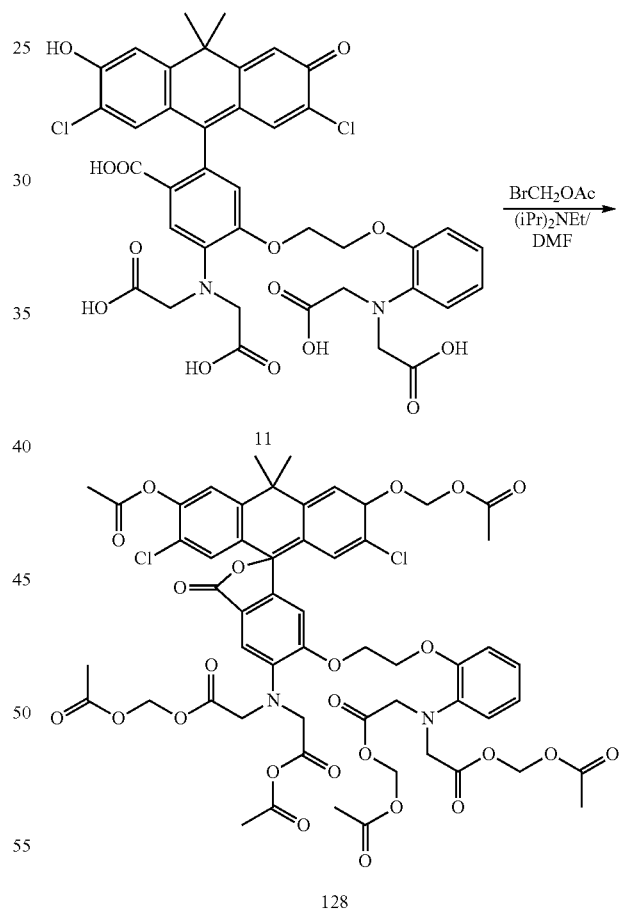

Compound 125 is prepared from Compound 122 analogously to the procedure of Compound 8. Compound 122 (40 mg) is heated at 80° C. with Ac$_2$O (5 mL) and pyridine (0.1 mL) until Compound 122 is completely consumed. The solution is cooled to room temperature. The reaction mixture is poured into ice water, and carefully adjusted to pH=4-5. The aqueous mixture is titrated with dioxane to give a precipitate that is collected by filtration. The resulting mixture is first air-dried, and further vacuum-dried in a desiccator with P$_2$O$_5$ for 12 hours to yield crude Compound 123 that is directly used for next step reaction.

The crude Compound 123 (40 mg) is dissolved in anhydrous DMF (2 mL) at room temperature. To the solution of Compound 123 BrCH$_2$OAc (0.1 mL) was slowly added while stirring in a water bath. To the resulted mixture iPr$_2$NEt (0.3 mL) is added slowly. The reaction mixture is stirred until Compound 123 is completely consumed and concentrated in vacuo. The residue is suspended in ethyl acetate (20 mL) and stirred for 1-2 hours. The mixture is filtered to remove the solid that is washed with ethyl acetate, and the filtrate is evaporated to dryness. The filtrate residue is purified on a silica gel column using 3:1:1 hexanes/EtOAc/chloroform as an eluent to give the desired Compound 125.

Example 26

Preparation of Compound 128

Compound 128 (100 mg) is dissolved in anhydrous DMF (3 mL) at RT. To the solution BrCH$_2$OAc (0.5 mL) is slowly added while stirring in a water bath. To the resulted mixture iPr$_2$NEt (0.38 mL) is added slowly. The reaction mixture is stirred for 24-36 hours, and concentrated in vacuo. The oily residue is purified on a silica gel column using 3:1:1 EtOAc/hexanes/chloroform as an eluent to give the desired Compound 128.

Example 27
Preparation of Compounds 132 and 133
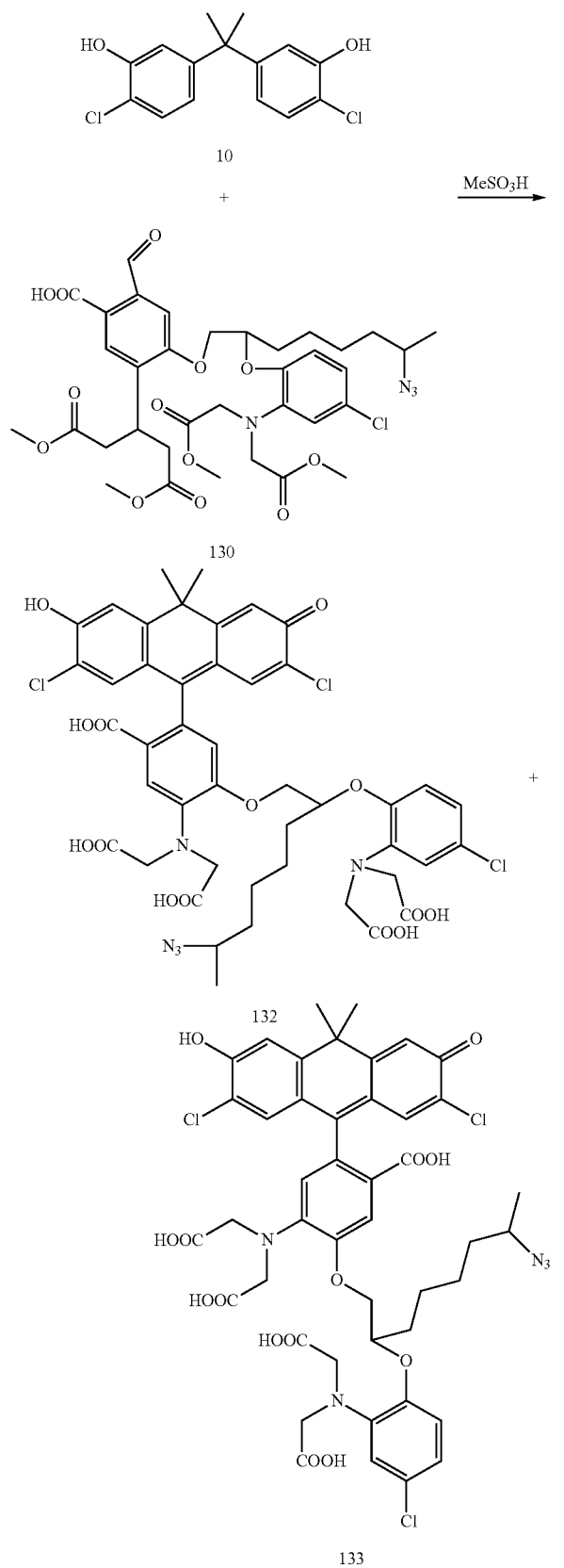
The mixture of free acid Compounds 132 and 133 are prepared from the reaction of Bisphenol 10 with Compound 130 analogously to the procedure of S. Gaillard et al. (Org. Lett. 2007, 9, 2629-2632).
Example 28
Preparation of Compounds 135
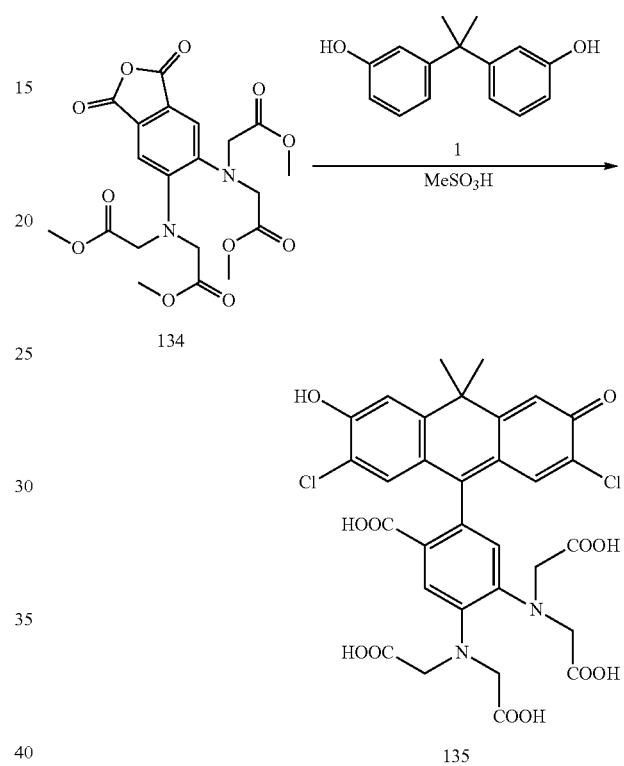
Compound 135 is analogously prepared according to the procedure of Compounds 3 and 4.
Example 29
Preparation of Compound 139
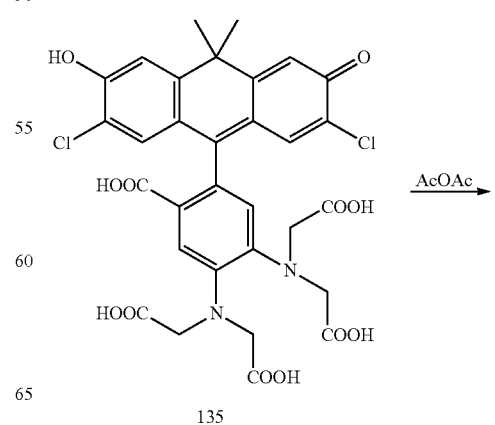

95
-continued
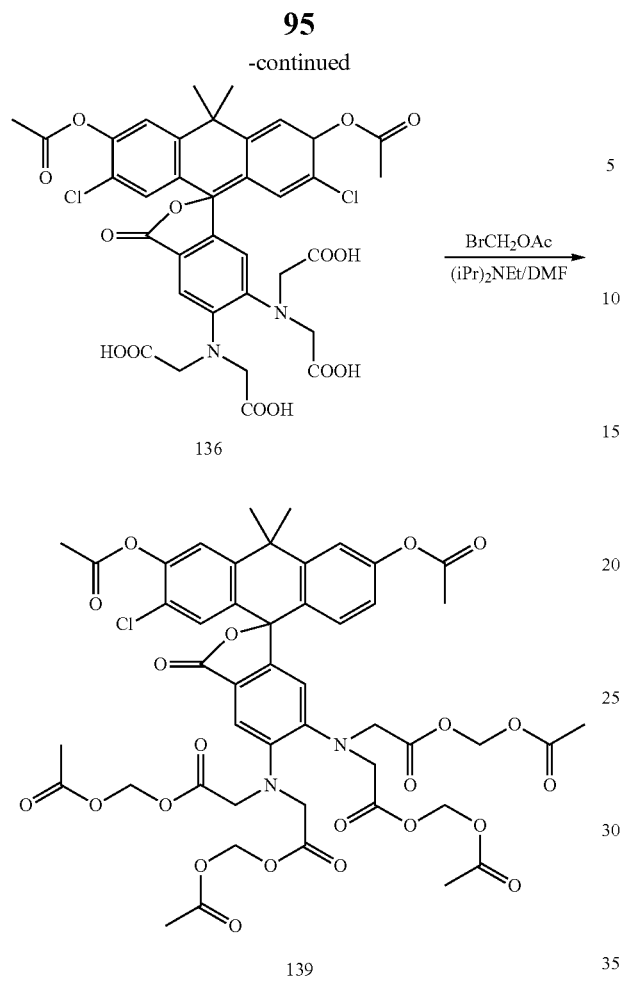
Compound 139 is prepared from Compound 135 analogously to the procedure of Compound 8.
Example 30
Preparation of Compounds 143
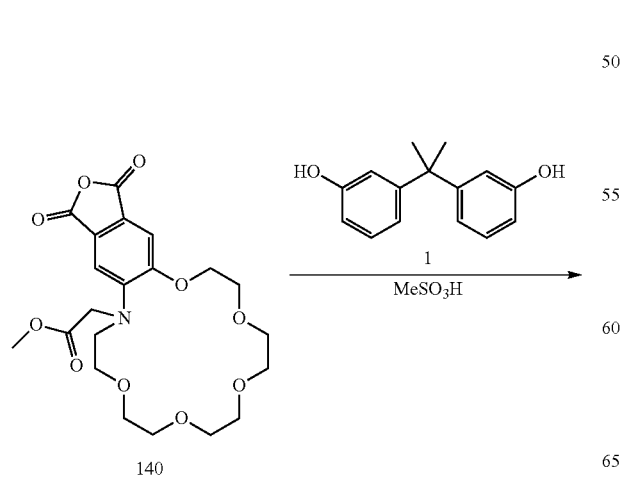
96
-continued
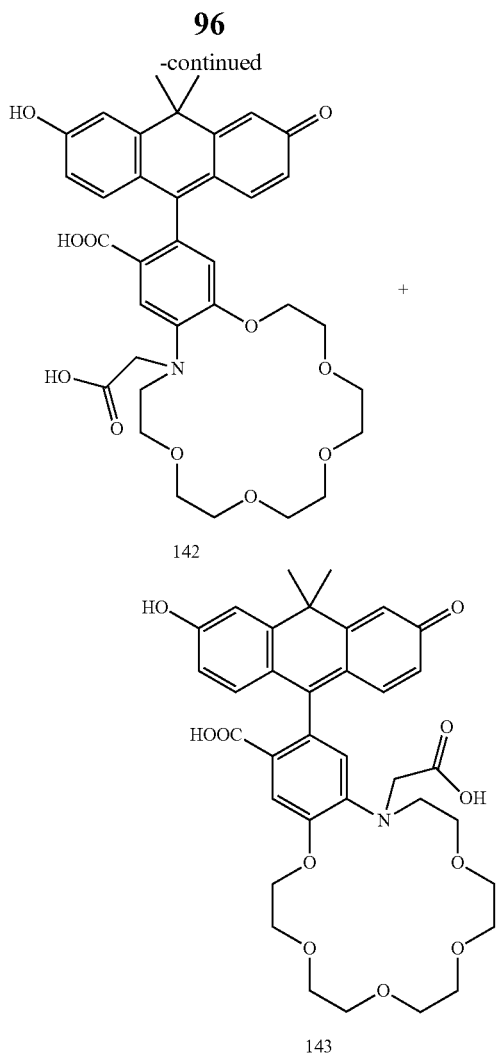
Compound 142 and 143 is analogously prepared from Compound 140 according to the procedure of Compounds 3 and 4.
Example 31
Preparation of Compound 145
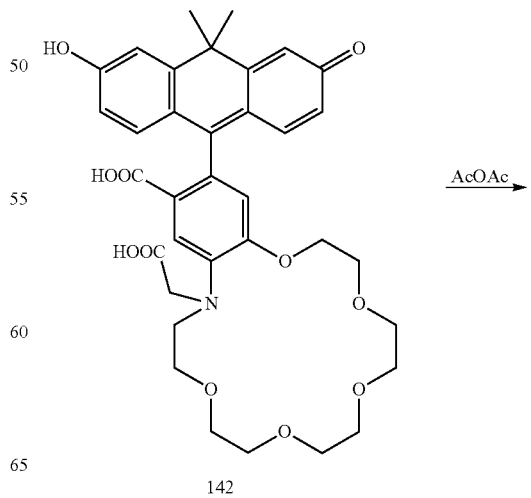

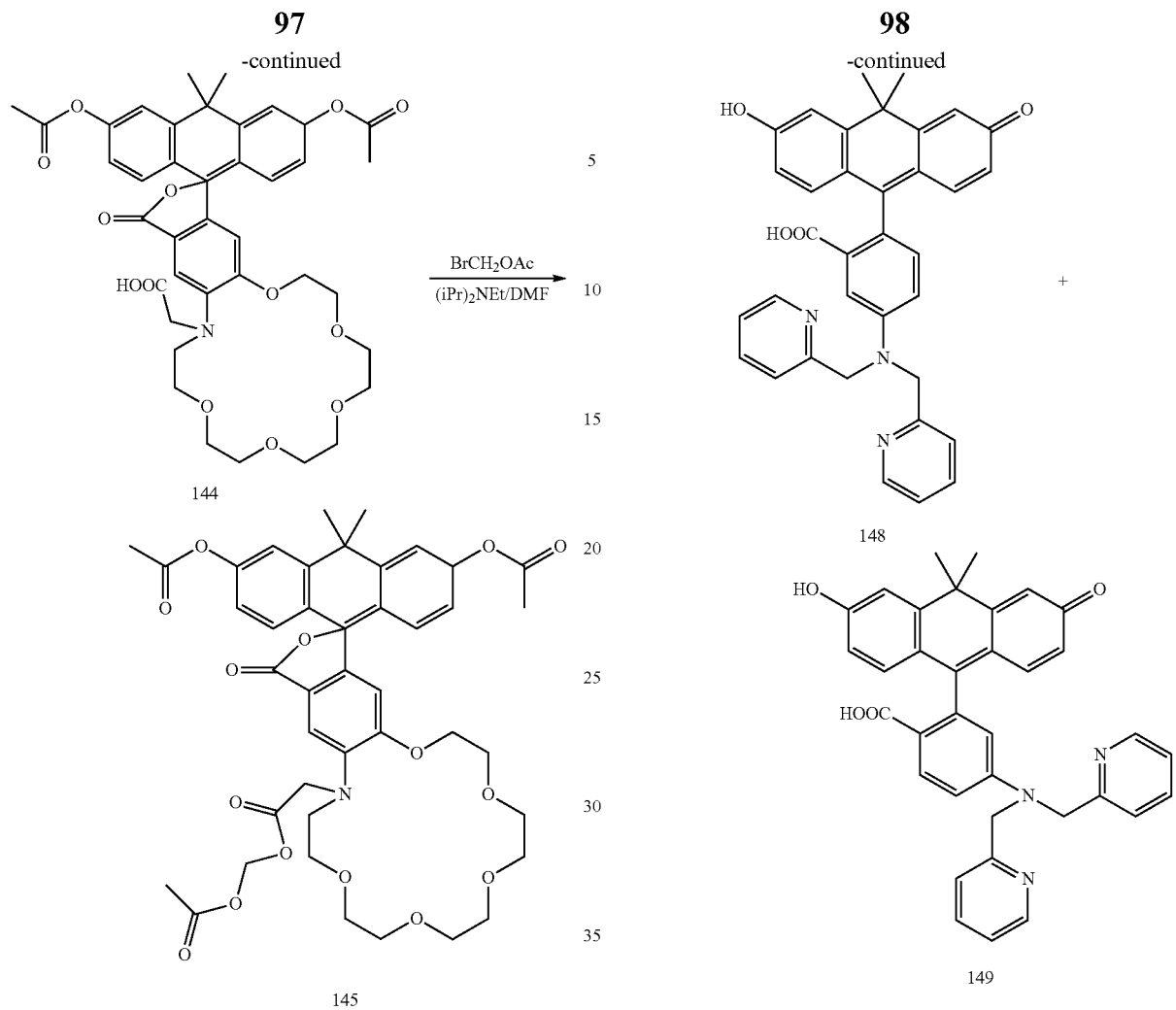
Compound 145 is prepared from Compound 142 analogously to the procedure of Compound 8.
Example 32
Preparation of Compounds 148 and 149
Compounds 148 and 149 are analogously prepared from Compound 146 according to the procedure of Compounds 3 and 4.
Example 33
Preparation of Compound 150
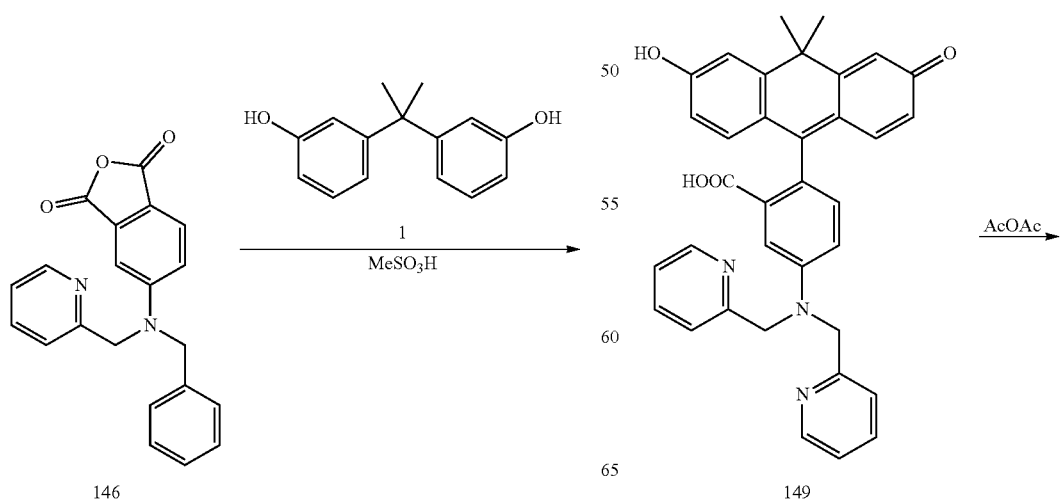

-continued

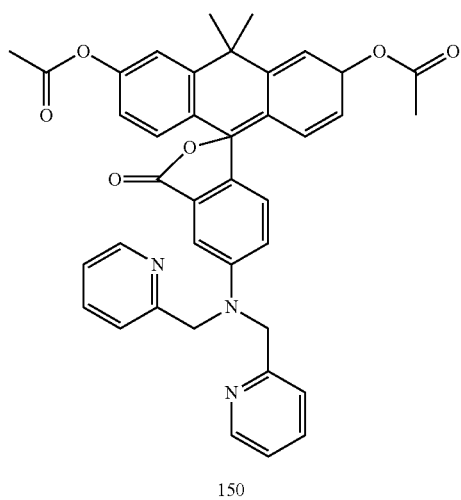

150

Compound 149 (50 mg) is heated at 80° C. with Ac$_2$O (5 mL) and pyridine (0.1 mL) until Compound 149 is completely consumed. The solution is cooled to room temperature. The reaction mixture is poured into ice water, and carefully adjusted to pH=6-7. The aqueous mixture is titrated with dioxane to give a precipitate that is collected by filtration. The resulting mixture is first air-dried, and further vacuum-dried in a desiccator with P$_2$O$_5$ for 12 hours to yield crude Compound 150 that is purified on a silica gel column using a gradient of chloroform/methanol as an eluent to give the desired Compound 150.

Example 34

Calcium Responses of the Fluorescent Indicators Measured Using a Microplate Reader Equipped with an Automated Liquid Handling System Calcium flux assays are preferred methods in drug discovery for screening G protein coupled receptors (GPCR). The fluorescent indicators of the invention provide a homogeneous fluorescence-based assay for detecting the intracellular calcium mobilization. Cells expressing a GPCR of interest that signals through calcium are pre-loaded with the indicator AM esters (such as Fluo-3 AM, Fluo-4 AM, Compounds 8, 16, 85, 125 or 128) which can cross cell membrane. Once inside the cell, the lipophilic blocking groups are cleaved by non-specific cell esterase, resulting in a negatively charged fluorescein dye that is well-retained in cells, and its fluorescence is greatly enhanced upon binding to calcium. When the sample cells are stimulated with screening compounds, the receptor triggers a release of intracellular calcium, which then greatly increases the fluorescence of the intracellular indicators. The combination of long wavelength fluorescence properties, high sensitivity, and often a >100 times increase in fluorescence upon binding with calcium makes the disclosed indicators well-suited for measurement of cellular calcium.

Figure 3:
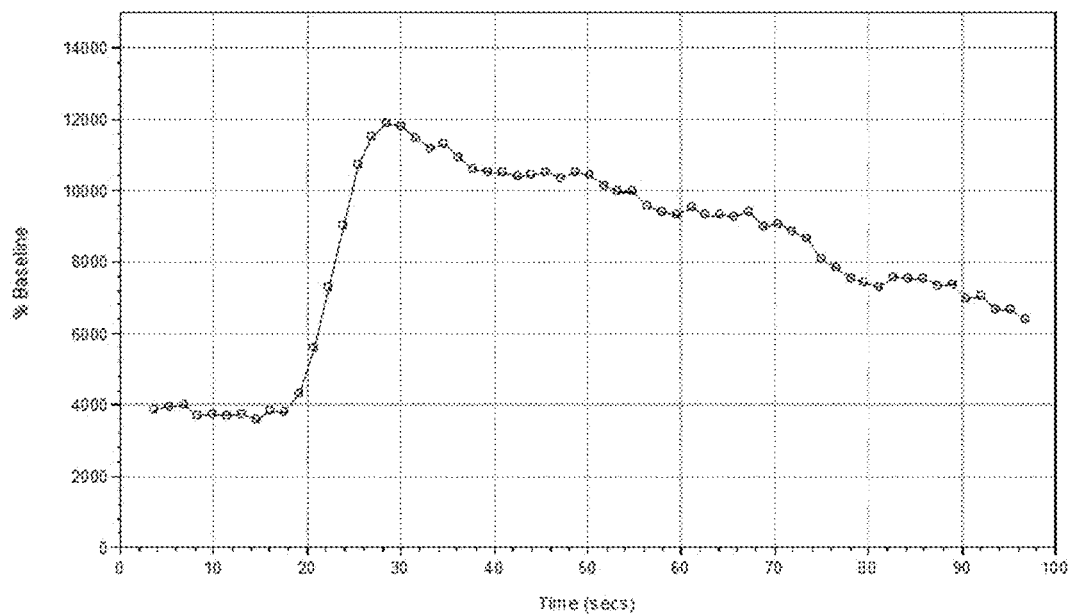
FIG. 3. Calcium responses of Compound 85 in CHO—K1 cells measured with a fluorescence microplate reader. CHO—K1 cells are seeded overnight at 50,000 cells per 100 μl per well in a 96-well black wall/clear bottom costar plate. The growth medium is removed, and the cells are incubated with 100 μl of Compound 85 at 5 μM in Hanks and Hepes buffer in the presence of 1 mM probenecid for 3 hours at 37° C., 5% $CO_2$ incubator. ATP (50 μL/well) was added by FlexStation to achieve the final desired concentrations.
Figure 4:
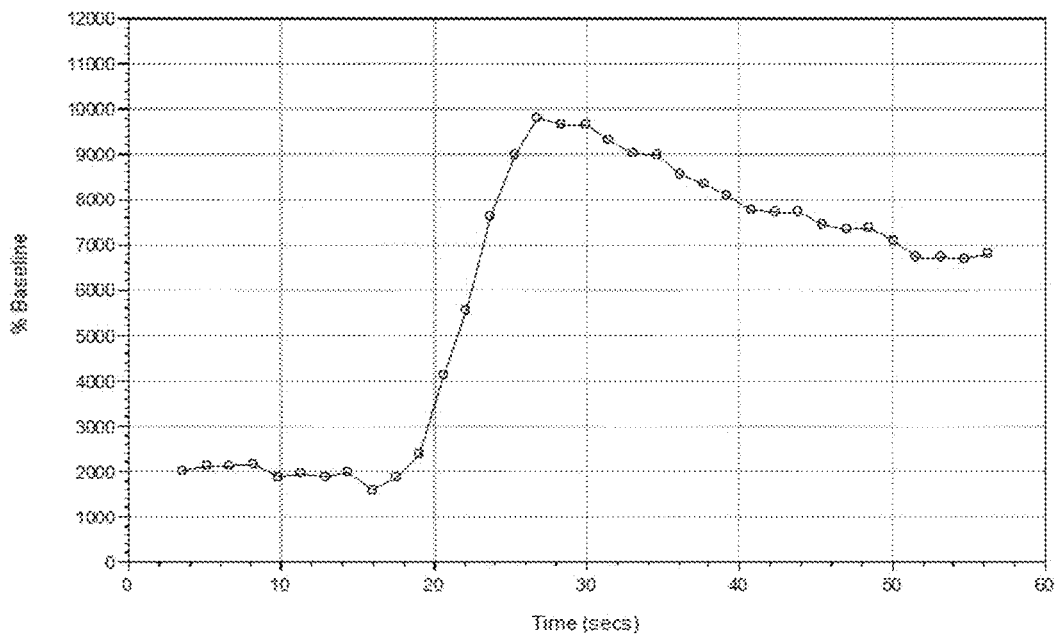
FIG. 4. Calcium responses of Compound 125 in CHO—K1 cells measured with a fluorescence microplate reader. CHO—K1 cells are seeded overnight at 50,000 cells per 100 μl per well in a 96-well black wall/clear bottom costar plate. The growth medium is removed, and the cells are incubated with 100 μl of Compound 125 at 5 μM in Hanks and Hepes buffer in the presence of 1 mM probenecid for 3 hours at 37° C., 5% $CO_2$ incubator. ATP (50 μl/well) was added by FlexStation to achieve the final desired concentrations.

Specifically, CHO cells stably transfected with muscarinic receptor 1 are plated at 60,000 cells per 100 µl per well in F12 with 5% FBS and 1% L-glutamine in a 96-well black wall/clear bottom Costar plate, incubated in 5% CO$_2$, 37° C. incubator overnight. The growth medium is removed and the cells are incubated with 100 µL/well of 1-8 µM Fluo-4 AM or Compound 85 in Hanks and HEPES buffer with 0 mM or 2.5 mM probenecid for 1 hour at room temperature. ATP (50 µl/well) is added by NOVOstar (BMG LabTech) or FLIPR (Molecular Devices) to achieve the final indicated concentration. A representative dose response is shown in FIGS. 3 and 4. In the absence of probenecid Compound 85 demonstrates the unexpected better fluorescence intensity enhancement upon calcium stimulation than that of Fluo-4 AM.

Example 35

Calcium Responses of the Fluorescent Indicators Measured Using a Fluorescence Imaging Device Calcium flux assays are preferred methods in drug discovery for screening G protein coupled receptors (GPCR). The fluorescent indicators of the invention provide a homogeneous fluorescence-based assay for detecting the intracellular calcium mobilization. Cells expressing a GPCR of interest that signals through calcium are pre-loaded with the indicator AM esters (such as Fluo-3 AM, Fluo-4 AM, Compounds 8, 16, 85, 125 or 128) which can cross cell membrane. Once inside the cell, the lipophilic blocking groups are cleaved by non-specific cell esterase, resulting in a negatively charged fluorescein dye that is well-retained in cells, and its fluorescence is greatly enhanced upon binding to calcium. When the sample cells are stimulated with screening compounds, the receptor triggers a release of intracellular calcium, which then greatly increases the fluorescence of the intracellular indicators. The combination of long wavelength fluorescence properties, high sensitivity, and often a >100 times increase in fluorescence upon binding with calcium makes the disclosed indicators well-suited for measurement of intracellular calcium.

Figure 11:
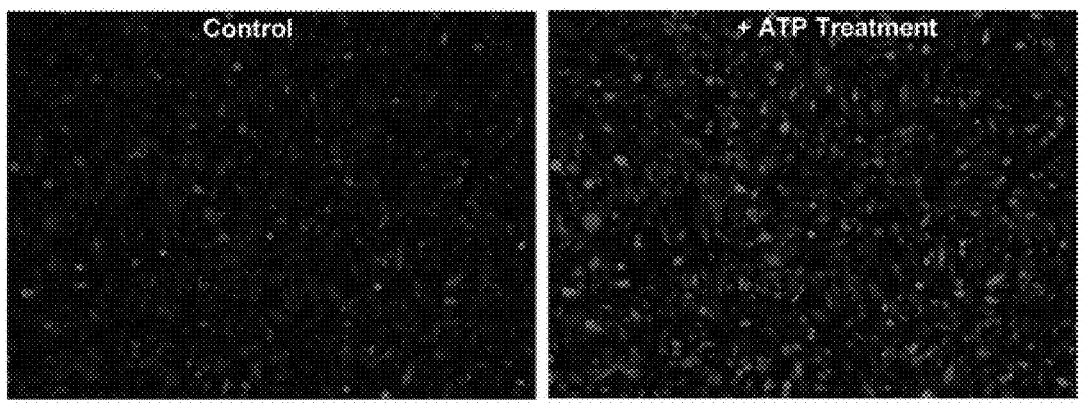
FIG. 11. Calcium responses of Compound 125 in CHO—K1 cells measured with a fluorescence microscope. CHO—K1 cells are seeded overnight at 50,000 cells per 100 µl per well in a 96-well black wall/clear bottom costar plate. The growth medium is removed, and the cells are incubated with 100 µl of Compound 125 at 5 µM in Hanks and Hepes buffer in the presence of 1 mM probenecid for 3 hours at 37° C., 5% $CO_2$ incubator. ATP (3 µM, 50 µL/well) was added, and imaged with a fluorescence microscope using TRITC channel.
Figure 12:
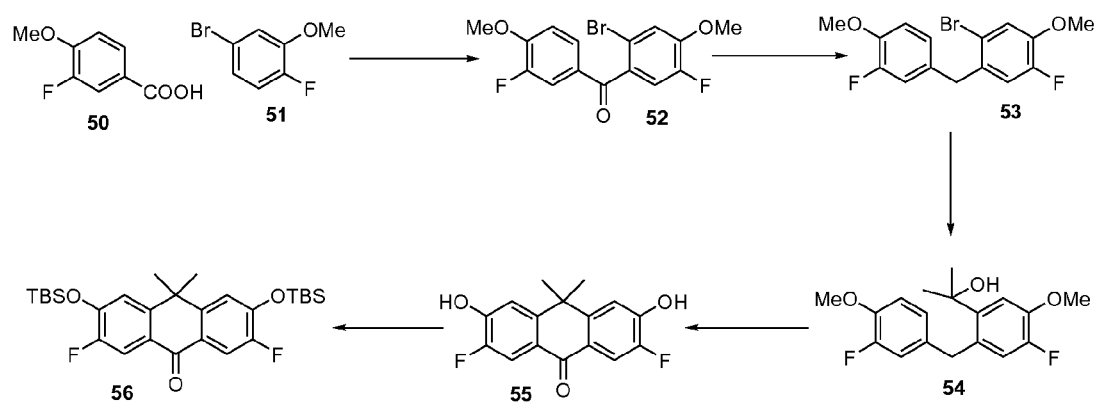
FIG. 12. Preparation of Compound 56. Compounds 50 and 51 are combined to give Compound 52 which is readily converted to Compound 56 according to the procedure of J. B. Grimm et al. (ACS Chem Biol 2013, 8, 1303-1310).

Specifically, CHO cells stably transfected with muscarinic receptor 1 are plated at 60,000 cells per 100 µl per well in F12 with 5% FBS and 1% L-glutamine in a 96-well black wall/clear bottom Costar plate, incubated in 5% CO$_2$, 37° C. incubator overnight. The growth medium is removed and the cells are incubated with 100 µL/well of 1-8 µM Fluo-4 AM or Compound 85 in Hanks and HEPES buffer with 0 mM or 2.5 mM probenecid for 1 hour at room temperature. ATP (50 µl/well) is added by NOVOstar (BMG LabTech) or FLIPR (Molecular Devices) to achieve the final indicated concentration. A representative dose response is shown in FIGS. 11 and 12. In the absence of probenecid Compound 85 demonstrates the unexpected better fluorescence intensity enhancement upon calcium stimulation than that of Fluo-4 AM.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A compound having the formula:

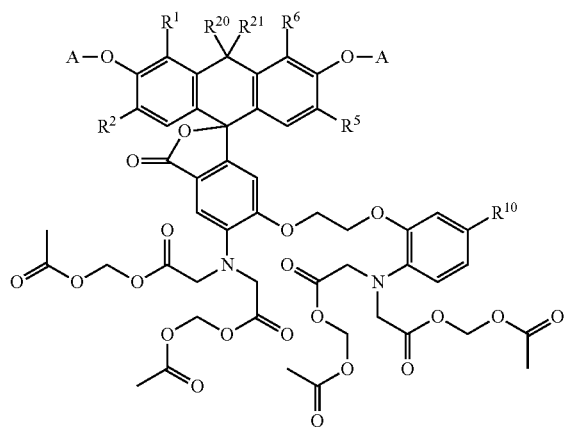

wherein:
A is acetyl or acetoxymethyl;
$R^2$ and $R^5$ are chloro;
$R^1$ and $R^6$ are chloro; and
$R^{10}$ is hydrogen or methyl.

2. A method of monitoring intracellular calcium using a compound of claim 1, comprising:

a) contacting a sample comprising a cell with the compound;
b) incubating the sample for a time sufficient for the compound to be loaded into the cell and an indicator compound to be generated intracellularly;
c) illuminating the sample at a wavelength that generates a fluorescence response from the indicator compound;
d) detecting a fluorescence response from the indicator compound.

3. The method of claim 2, further comprising:
stimulating the cell;
monitoring changes in the intensity of the fluorescence response from the indicator compound; and
correlating the changes in fluorescence intensity with changes in intracellular calcium levels.

4. The method of claim 3, further comprising adding a cell-impermeant and non-fluorescent dye to the sample.

5. A kit for performing a calcium assay, comprising a compound of claim 1.

6. The kit of claim 5, wherein the non-fluorescent and cell-impermeant quencher dye is present in a mixed powder or mixed solution with the compound, or the cell-impermeant quencher dye is provided in a separate container.

7. The compound according to claim 1, wherein A is acetyl, $R^2$ and $R^5$ are chloro, $R^1$ and $R^6$ are chloro, and $R^{10}$ is hydrogen.

* * * * *